(12) United States Patent
Buchanan et al.

(10) Patent No.: US 12,391,768 B2
(45) Date of Patent: Aug. 19, 2025

(54) ANTIBODIES TO TICAGRELOR AND METHODS OF USE

(71) Applicant: MEDIMMUNE LIMITED, Cambridge (GB)

(72) Inventors: Andrew Buchanan, Cambridge (GB); Sven Nylander, Sodertalje (SE); Mark Penney, Cambridge (GB); Philip Newton, Cambridge (GB); Feenagh Keyes, Cambridge (GB); Tord Inghardt, Sodertalje (SE)

(73) Assignee: Medimmune Limited, Cambridge (GB)

( * ) Notice: Subject to any disclaimer, the term of this patent is extended or adjusted under 35 U.S.C. 154(b) by 190 days.

(21) Appl. No.: 18/451,751

(22) Filed: Aug. 17, 2023

(65) Prior Publication Data

US 2024/0101712 A1 Mar. 28, 2024

Related U.S. Application Data

(60) Division of application No. 17/176,624, filed on Feb. 16, 2021, now Pat. No. 11,773,186, which is a division of application No. 16/035,954, filed on Jul. 16, 2018, now Pat. No. 10,954,308, which is a division of application No. 15/966,313, filed on Apr. 30, 2018, now abandoned, which is a continuation of application No. 14/871,111, filed on Sep. 30, 2015, now Pat. No. 9,982,061.

(60) Provisional application No. 62/114,931, filed on Feb. 11, 2015, provisional application No. 62/058,458, filed on Oct. 1, 2014.

(51) Int. Cl.
| | |
|---|---|
| C07H 21/04 | (2006.01) |
| C07D 487/04 | (2006.01) |
| C07K 16/44 | (2006.01) |
| A61K 39/00 | (2006.01) |

(52) U.S. Cl.
CPC ............ C07K 16/44 (2013.01); C07D 487/04 (2013.01); *A61K 2039/505* (2013.01); *C07K 2317/21* (2013.01); *C07K 2317/24* (2013.01); *C07K 2317/54* (2013.01); *C07K 2317/55* (2013.01); *C07K 2317/565* (2013.01); *C07K 2317/569* (2013.01); *C07K 2317/622* (2013.01); *C07K 2317/626* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,223,409 A | 6/1993 | Ladner | |
| 5,403,484 A | 4/1995 | Ladner | |
| 5,427,908 A | 6/1995 | Dower | |
| 5,516,637 A | 5/1996 | Huang | |
| 5,571,698 A | 11/1996 | Ladner | |
| 5,580,717 A | 12/1996 | Dower | |
| 5,658,727 A | 8/1997 | Barbas | |
| 5,698,426 A | 12/1997 | Huse | |
| 5,733,743 A | 3/1998 | Johnson | |
| 5,739,277 A | 4/1998 | Presta | |
| 5,750,753 A | 5/1998 | Kimae | |
| 5,780,225 A | 7/1998 | Wigler | |
| 5,821,047 A | 10/1998 | Garrard | |
| 5,969,108 A | 10/1999 | Mccafferty | |
| 6,525,060 B1 | 2/2003 | Hardern et al. | |
| 6,821,505 B2 | 11/2004 | Ward | |
| 7,083,784 B2 | 8/2006 | Dall | |
| 7,135,180 B2 | 11/2006 | Truong-le | |
| 7,258,873 B2 | 8/2007 | Truong-le et al. | |
| 7,326,681 B2 | 2/2008 | Gerngross | |
| 7,378,110 B2 | 5/2008 | Truong-le et al. | |
| 9,982,061 B2 * | 5/2018 | Buchanan | C07D 487/04 |
| 10,487,154 B2 * | 11/2019 | Buchanan | C07D 487/04 |
| 10,954,308 B2 * | 3/2021 | Buchanan | A61P 7/04 |
| 11,773,186 B2 * | 10/2023 | Buchanan | C07K 16/44 |
| | | | 435/375 |
| 2002/0098193 A1 | 7/2002 | Ward | |
| 2003/0190311 A1 | 10/2003 | Dall | |
| 2004/0042971 A1 | 3/2004 | Truong-le et al. | |
| 2004/0042972 A1 | 3/2004 | Truong-le et al. | |
| 2008/0066200 A1 | 3/2008 | Dickey et al. | |
| 2009/0197834 A1 | 8/2009 | Koga et al. | |

(Continued)

FOREIGN PATENT DOCUMENTS

| | | |
|---|---|---|
| CA | 2963166 A1 | 4/2016 |
| CN | 1128801 C | 11/2003 |

(Continued)

OTHER PUBLICATIONS

Almquist, J. et al. (2016) "Unraveling the Pharmacokinetic Interaction of Ticagrelor and MEDI2452 (Ticagrelor Antidote) by Mathematical Modeling," CPT: Pharmacometrics & Systems Pharmacology 5(6):313-323.

(Continued)

*Primary Examiner* — Michael Szperka

(74) *Attorney, Agent, or Firm* — Morrison & Foerster LLP

(57) ABSTRACT

The disclosure generally provides antibodies and antigen binding fragments of antibodies that bind ticagrelor and metabolites of ticagrelor. The disclosure also provides compositions comprising the antibodies, nucleic acid molecules encoding the antibodies, methods of treating a patient comprising administering the antibodies, and methods of making and using the antibodies.

17 Claims, 16 Drawing Sheets

Specification includes a Sequence Listing.

(56) References Cited

U.S. PATENT DOCUMENTS

| | | | |
|---|---|---|---|
| 2016/0130366 | A1 | 5/2016 | Buchanan et al. |
| 2016/0176912 | A1 | 6/2016 | Cosgrove et al. |
| 2018/0055940 | A1 | 3/2018 | Ma et al. |
| 2018/0319897 | A1 | 11/2018 | Buchanan et al. |
| 2019/0077882 | A1 | 3/2019 | Buchanan et al. |
| 2021/0347915 | A1 | 11/2021 | Lee et al. |
| 2021/0371546 | A1 | 12/2021 | Buchanan et al. |
| 2023/0192895 | A1 | 6/2023 | Lee |

FOREIGN PATENT DOCUMENTS

| | | |
|---|---|---|
| CN | 101646690 A | 2/2010 |
| JP | H03154867 A | 7/1991 |
| JP | 2017517307 A | 6/2017 |
| JP | 6799530 B2 | 11/2020 |
| TW | I707870 B | 10/2020 |
| WO | 199002809 A1 | 3/1990 |
| WO | 199110737 A1 | 7/1991 |
| WO | 199201047 A1 | 1/1992 |
| WO | 199218619 A1 | 10/1992 |
| WO | 199222324 A1 | 12/1992 |
| WO | 199311236 A1 | 6/1993 |
| WO | 199520401 A1 | 8/1995 |
| WO | 199515982 A3 | 12/1995 |
| WO | 199713844 A1 | 4/1997 |
| WO | 199905143 A1 | 2/1999 |
| WO | 200034283 A1 | 6/2000 |
| WO | 2008036341 A2 | 3/2008 |
| WO | 2008142124 A1 | 11/2008 |
| WO | 2009018386 A1 | 2/2009 |
| WO | 2009058492 A2 | 5/2009 |
| WO | 2013006544 A1 | 1/2013 |
| WO | 2013055984 A1 | 4/2013 |
| WO | 2016050867 A1 | 4/2016 |
| WO | 2018116267 A2 | 6/2018 |
| WO | 2018158332 A1 | 9/2018 |
| WO | 2020061465 A1 | 3/2020 |
| WO | 2022240754 A2 | 11/2022 |

OTHER PUBLICATIONS

Ames, R.S. et al. (Aug. 18, 1995). "Conversion of Murine Fabs Isolated From a Combinatorial Phage Display Library to Full Length Immunoglobulins," J. Immunol. Methods 184(2):177-186.
Amsterdam, E.A. et al. (2014). "2014 AHA/ACC Guideline for the Management of Patients With Non-ST-Elevation Acute Coronary Syndromes," A Report of the American College of Cardiology/ American Heart Association Task Force on Practice Guidelines, J Am Coll Cardiol. 64(24):e139-e228.
Aradi, D. et al. (2015). "Bleeding and Stent Thrombosis on P2Y12- Inhibitors: Collaborative Analysis on the Role of Platelet Reactivity for Risk Stratification After Percutaneous Coronary Intervention," European Heart Journal 36 (27):1762-1771.
Astrand, M. et al. (2019). "Pharmacokinetic-Pharmacodynamic Modelling of Platelet Response to Ticagrelor in Stable Coronary Artery Disease and Prior Myocardial Infarction Patients," British Journal of Clinical Pharmacology 85 (2):413-421.
Author Unknown "Thermo Scientific Pierce Epitope Tag Antibodies," located at https://www.fishersci.de/contenUdam/fishersci/en_ US/documents/programs/scientific/brochures-and- catalogs/fliers/ thermo-scientific-pierce-epitope-tag-antibodies-flyer.pdf last visited on Jan. 9, 2018, 2 pages.
Bauer, R.J. (2019). "NONMEM Tutorial Part II: Estimation Methods and Advanced Examples," CPT: Pharmacometrics & Systems Pharmacology 8(8):538-556.
Better, M. et al. (May 20, 1988). "*Escherichia coli* Secretion of an Active Chimerica Antibody Fragment," Science 240:1041-1043, 4 pages.
Bhatt, D.L. (Nov. 15, 2007). "Intensifying Platelet Inhibition- Navigating between Scylla and Charybdis," New England Journal of Medicine 357(20):2078-2081.

Bhatt, D.L. et al. (2014). "Antiplatelet and Anticoagulation Therapy for Acute Coronary Syndromes," Circulation Research 114(12):1929- 1943.
Bhatt, D.L. et al. (Apr. 20, 2006). "Clopidogrel and Aspirin versus Aspirin Alone for the Prevention of Atherothrombotic Events," New England Journal of Medicine 354(16):1706-1717.
Bhatt, D.L. et al. (May 15, 2007). "Patients With Prior Myocardial Infarction, Stroke, or Symptomatic Peripheral Arterial Disease in the CHARISMA Trial," Journal of the American College of Cardiology 49(19):1982-1988.
Bhatt, D.L. et al. (May 9, 2019). "Antibody-Based Ticagrelor Reversal Agent in Healthy Volunteers," New England Journal of Medicine 380(19):1825-1833.
BRILINTA® (ticagrelor) Tablets: 60 mg and 90 mg, Label; Highlights of Prescribing Information, Patient Information approved by the U.S. Food and Drug Administration; Revised: Sep. 2016, Initial U.S. Approval: 2011, Reference ID: 3989896, Distributed by: AstraZeneca Pharmaceuticals LP, Wilmington, DE 19850 USA, 26 pages.
Brinkmann, U. et al. (1993). "A Recombinant Immunotoxin Containing a Disulfide-Stabilized Fv Fragment," PNAS 90(16):7538- 7542.
Brinkmann, U. et al. (May 11, 1995). "Phage Display of Disulfide- Stabilized Fv Fragments," J. Immunol. Methods 182(1):41-50.
Buchanan, A. et al. (May 28, 2015). "Structuraland Functional Characterization of a Specific Antidote for Ticagrelor," Blood 125(22):3484-3490.
Burton, D.R. et al. (1994). "Human Antibodies From Combinatorial Libraries," Advances in Imniunology 57:191-280.
Cannon, C.P. et al. (Jan. 23, 2010). "Comparison Ofticagrelorwith Clopidogrel in Patients With a Planned Invasive Strategy for Acute Coronary Syndromes (PLATO): A Randomised Double-Blind Study," The Lancet 375 (9711):283-293.
Capodanno, D. et al. (2013). "Management of Antiplatelet Therapy in Patients With Coronary Artery Disease Requiring Cardiac and Noncardiac Surgery," Circulation 128(25):2785-2798.
Carter, P. et al. (Feb. 1992). "High Level *Escherichia coli* Expression and Production of a Bivalent Humanized Antibody Fragment," Bio/Technology 10:163-167.
Cattaneo, M. et al. (Jun. 2014). "Adenosine-Mediated Effects of Ticagrelor: Evidence and Potential Clinical Relevance," Journal of the American College of Cardiology 63(23):2503-2509.
Chen, Z.M. et al. (Nov. 5, 2005). "Addition of Clopidogrel to Aspirin In 45,852 Patients With Acute Myocardial Infarction: Randomised Placebo-Controlled Trial," The Lancet 366(9497):1607- 1621.
Colburn, W.A. (1980). "Specific Antibodies and Fab Fragments to Alter the Pharmacokinetics and Reverse the Pharmacologic/ Toxicologic Effects of Drugs," Drug Metabolism Reviews 11(2):223- 262.
Crowther, M.A. et al. (Mar. 3, 2009). "Oral Vitamin K Versus Placebo to Correct Excessive Anticoagulation in Patients Receiving Warfarin: A Randomized Trial," Annals of Internal Medicine 150(5):293- 300.
Dalen, M. et al. (Oct. 2013). "Ticagrelor-Associated Bleeding in a Patient Undergoing Surgery for Acute Type A Aortic Dissection," Journal of Cardiothoracic and Vascular Anesthesia 27(5):e55-e57.
Daramola, O. et al. (2014, e-pub. Sep. 19, 2013). "A High-Yielding CHO Transient System: Coexpression of Genes Encoding EBNA-1 and GS Enhances Transient Protein Expression," Biotechnology Progress 30(1):132-141.
Dolgin, E. (Mar. 2013). "Antidotes Edge Closer to Reversing Effects of New Blood Thinners," Nature Medicine 19 (3):251.
Douketis, J.D. et al. (2012). "Perioperative Management of Antithrombotic Therapy: Antithrombotic Therapy and Prevention of Thrombosis, 9th ed: American College of Chest Physicians Evidence- Based Clinical Practice Guidelines," Chest 141(2):e326S-e350S.
Ducrocq, G. et al. (2013). "A History of Stroke/Transient Ischemic Attack Indicates High Risks of Cardiovascular Event and Hemorrhagic Stroke in Patients With Coronary Artery Disease," Circulation 127(6):730-738.

(56) References Cited

OTHER PUBLICATIONS

Edwards, B.M. et al. (Nov. 14, 2003). "The Remarkable Flexibility of the Human Antibody Repertoire; Isolation of Over One Thousand Different Antibodies to a Single Protein, Blys," J. Mol. Biol. 334(1):103-118.

Effient (prasugrel) Tablets: 5 mg and 10 mg (3), Label; Highlights of Prescribing Information, Patient Information approved by the U.S. Food and Drug Administration; Revised: Jul. 2009, Initial U.S. Approval: 2009, Application No. 22-307, Manufactured by: Eli Lilly and Company, Indianapolis, IN, 46285 USA, 17 pages.

Effient (prasugrel) Tablets: 5 mg and 10 mg (3), Label; Highlights of Prescribing Information, Patient Information approved by the U.S. Food and Drug Administration; Revised: Sep. 2011, Initial U.S. Approval: 2009, Reference ID: 3020401, Manufactured by: Eli Lilly and Company, Indianapolis, IN, 46285 USA, 16 pages.

Emsley, P. et al. (Dec. 2004). "Model-Building Tools for Molecular Graphics," Acta Crystallographica Section D, Biological Crystallography 60(12):2126-2132.

Extended European Search Report, dated Jul. 21, 2022, for European Patent Application No. 19863329.9, 8 pages.

Faber, C. et al. (1998). "Three-Dimensional Structure of a Human Fab With High Affinity for Tetanus Toxoid," Immunotechnology 3(4):253-270.

Fanning, S.W. et al. (Jul. 2011). "An Anti-Hapten Camelid Antibody Reveals a Cryptic Binding Site With Significant Energetic Contributions From a Nonhypervariable Loop," Protein Science 20(7):1196-1207.

Ghahroudi, M.A et al. (Sep. 15, 1997). "Selection and Identification of Single Domain Antibody Fragments From Camel Heavy-Chain Antibodies," FEBS Lett. 414(3):521-526.

Glockshuber, R. et al. (1990). "A Comparison of Strategies to Stablize Immunoglobulin Fv-Fragments," Biochemistry 13:29(6):1362-1367.

Godier, A. et al. (Jan. 8, 2015). "Inefficacy of Platelet Transfusion to Reverse Ticagrelor," New England Journal of Medicine 372(2):196-197.

Goel, M. et al. (2004). "Plasticity within the Antigen-Combining Site May Manifest as Molecular Mimicry in the Humoral Immune Response," J. Immunol. 173(12):7358-7367.

Gurbel, P.A. et al. (2009). "Randomized Double-Blind Assessment of the ONSET and OFFSET of the Antiplatelet Effects of Ticagrelor Versus Clopidogrel in Patients With Stable Coronary Artery Disease: The ONSET/OFFSET Study," Circulation 120(25):2577-2585.

Hansson, E.C. et al. (Mar. 2014). "Effects of Ex Vivo Platelet Supplementation on Platelet Aggregability in Blood Samples From Patients Treated With Acetylsalicylic Acid, Clopidogrel, or Ticagrelor," Br J Anaesthesia 112 (3):570-575.

Held, C. et al. (2011). "Ticagrelor Versus Clopidogrel in Patients With Acute Coronary Syndromes Undergoing Coronary Artery Bypass Surgery: Results From The PLATO (Platelet Inhibition and Patient Outcomes) Trial," Journal of the American College of Cardiology 57(6):672-684.

Hillis, L.D. et al. (2011). "2011 ACCF/AHA guideline for coronary artery bypass graft surgery: executive summary: a report of the American College of Cardiology Foundation/American Heart Association Task Force on Practice Guidelines," Circulation 124(23):2610-2642.

Husted, S.E. et al. (Jun. 2012). "Pharmacokinetics and Pharmacodynamics of Ticagrelor in Patients With Stable Coronary Artery Disease: Results From the ONSET-OFFSET and RESPOND Studies," Clinical Pharmacokinetics 51 (6):397-409.

International Preliminary Report on Patentability, issued Apr. 4, 2017, mailed Jan. 18, 2016, for PCT Application No. PCT/EP2015/072606, filed Sep. 30, 2015, 7 pages.

International Preliminary Report on Patentability, issued Mar. 23, 2021, mailed Jan. 31, 2020, for PCT Application No. PCT/US2019/052173, filed Sep. 20, 2019, 11 pages.

International Search Report and the Written Opinion of the International Searching Authority mailed Jan. 18, 2016, for International Patent Application No. PCT/EP2015/072606, filed Sep. 30, 2015, 11 pages.

International Search Report and the Written Opinion of the International Searching Authority mailed Jan. 31, 2020, for International Patent Application No. PCT/US2019/052173, filed Sep. 20, 2019, 15 pages.

International Search Report and the Written Opinion of the International Searching Authority mailed Nov. 1, 2022, for International Patent Application No. PCT/US2022/28343, filed May 9, 2022, 11 pages.

Invitation to Pay Additional Fees mailed on Nov. 22, 2019, for PCT Application No. PCT/US2019/052173, filed on Sep. 20, 2019, 2 pages.

James, S.K. et al. (2011). "Ticagrelor Versus Clopidogrel in Patients With Acute Coronary Syndromes Intended for Non-Invasive Management: Substudy From Prospective Randomised PLATelet Inhibition and Patient Outcomes (PLATO) Trial," BMJ 342:1-11.

Janeway, C.A. et al. (1997). Immunobiology, 12 pages.

Jayasinghe, R. et al. (Oct. 2013). "Dual Antiplatelet Therapy: Management in General Practice," Australian Family Physician 42(10):702-705.

Jin, L. et al. (2017, e-pub. Jul. 11, 2016). "The Prognostic Value of ADP-Induced Platelet Aggregation for Bleeding Complications in Low-Intermediate Risk Patients with Acute Coronary Syndrome Taking Clopidogrel After Percutaneous Coronary Intervention," Heart, Lung and Circulation 26(1):49-57.

Kanyavuz, A. et al. (Jun. 2019). "Breaking the Law: Unconventional Strategies for Antibody Diversification," Nat. Rev. Immunol 19(6):355-368.

Kettleborough, C.A. et al. (Apr. 1994). "Isolation of Tumor Cell-Specific Single-Chain Fv From Immunized Mice Using Phage-Antibody Libraries and the Re-Construction of Whole Antibodies From These Antibody Fragments," Eur. J. Immunol. 24(4):952-958.

Kipriyanov, S.M. et al. (2004). "Generation and Production of Engineered Antibodies," Molecular Biotechnology 26 (1):39-60.

Koski, R. et al. (Jun. 2018). "Comparative Review of Oral P2Y12 Inhibitors," Pharmacy and Therapeutics 43 (6):352-357.

Kuznetsov, D.N. et al. (2011). "Clinical Effectiveness of Thrombolytic Therapy With Alteplase and Double Antiplatelet Therapy in Acute Myocardial Infarction," Cardiovascular Therapy and Prevention 10(6):59-63. [English Abstract].

Ladenson, R.C. et al. (Jul. 1, 2006, e-pub. Apr. 26, 2006). "Isolation and Characterization of a Thermally Stable Recombinant Anti-Caffeine Heavy-Chain Antibody Fragment," Analytical Chemistry 78(13):4501-4508.

Liu, F. et al. (2001). "Synthesis of 5'-Functionalized Adenosine: Suppression of Cyclonucleoside Formation," Tetrahedron Letters 42(18):3153-3154.

Lloyd, C. et al. (2009, e-pub. Oct. 29, 2008). "Modelling the Human Immune Response: Performance of a 1011 Human Antibody Repertoire Against a Broad Panel of Therapeutically Relevant Antigens," Protein Engineering, Design & Selection 22(3):159-168.

Lu, G. et al. (Apr. 2013) "A Specific Antidote for Reversal of Anticoagulation by Direct and Indirect Inhibitors of Coagulation Factor Xa," Nature Medicine 19(4):446-453.

Lunn, D.J. et al. (Jun. 2002). "Bayesian Analysis of Population PK/PD Models: General Concepts and Software," Journal of Pharmacokinetics and Pharmacodynamics 29(3):271-307.

Luo, D. et al. (Oct. 1995). "VI-linker-Vh Orientation-Dependent Expression of Single Chain Fv-Containing an Engineered Disulfide-Stabilized Bond in the Framework Regions," The Journal of Biochemistry 118(4):825-831.

Mangiacapra, F. et al. (2015). "Incremental Value of Platelet Reactivity Over a Risk Score of Clinical and Procedural Variables in Predicting Bleeding After Percutaneous Coronary Intervention via the Femoral Approach Development and Validation of a New Bleeding Risk Score," Circulation: Cardiovascular Interventions 8(5):1-8.

(56) References Cited

OTHER PUBLICATIONS

Mehta, S.R. et al. (2001). "Effects of Pretreatment With Clopidogrel and Aspirin Followed by Long-Term Therapy in Patients Undergoing Percutaneous Coronary Intervention: The PCI-CURE Study," The Lancet 358(9281):527-533.

Meyer, T. et al. (1986). "Production of Anti-(ADP-Ribose) Antibodies With the Aid of a Dinucleotide-Pyrophosphatase-Resistant Hapten and Their Application for the Detection of Mono(ADP-ribosyl)ated Polypeptides," The FEBS Journal 155(1):157-165.

Mullinax, R.L. et al. (1992). "Expression of a Heterodimeric Fab Antibody Protein in One Cloning Step," Biotechniques 12(6):864-869.

Nylander, S. et al. (Mar. 2013). "Ticagrelor-Induced Bleeding in Mice Can Be Reversed by Fviia (Novoseven®) and Fii," Journal of the American College of Cardiology 61(10S):E212.

Oprea, T.I et al. (Mar. 14, 2011). "Associating Drugs, Targets and Clinical Outcomes into an Integrated Network Affords a New Platform for Computer-Aided Drug Repurposing," Molecular Informatics 30(2-3):100-111, 16 pages.

Pehrsson, S. et al. (2017). "Hemostatic Effects of the Ticagrelor Antidote MEDI 2452 in Pigs Treated With Ticagrelor on a Background of Aspirin," Journal of Thrombosis and Haemostasis 15(6):1213-1222.

Perepech, N.B. (2016). "Acute Coronary Syndrome: Pathogenesis, Diagnosis, Treatment, Rehabilitation (Lecture 2)," CardioSomatics 7(2):70-81. [English Abstract].

Persic et al., "An integrated vector system for the eukaryotic expression of antibodies or their fragments after selection from phage display libraries," Gene (1997) 187(1):9-18.

PLAVIX (clopidogrel bisulfate) Tablets: 75 mg, 300 mg (3), Label; Highlights of Prescribing Information, Patient Information approved by the U.S. Food and Drug Administration; Revised: Aug. 2010, Initial U.S. Approval: 1997, Distributed by: Bristol-Myers Squibb/Sanofi Pharmaceuticals Partnership Bridgewater, NJ 08807 USA, 25 pages.

Pruller, F. et al. (Aug. 2011). "Low Platelet Reactivity Is Recovered by Transfusion of Stored Platelets: A Healthy Volunteer In Vivo Study," Journal of Thrombosis and Haemostasis 9(8):1670-1673.

Reed, G.W. et al. (2015). "Point-of-Care Platelet Function Testing Predicts Bleeding in Patients Exposed to Clopidogrel Undergoing Coronary Artery Bypass Grafting: Verify Pre-Op TIMI 45-A Pilot Study," Clinical Cardiology 38 (2):92-98.

Reiter, Y. et al. (1994). "Stabilization of the Fv Fragments in Recombinant Immunotoxins by Disulfide Bonds Engineered Into Conserved Framework Regions," Biochemistry 33:5451-5449.

Reiter, Y. et al. (Oct. 1996). "Engineering Antibody Fv Fragments for Cancer Detection and Therapy: Disulfide-Stabilized Fv Fragments," Nature Biotechnology 14:1239-1245.

Roe, M.T. et al. (Oct. 4, 2012). "Prasugrel Versus Clopidogrel for Acute Coronary Syndromes Without Revascularization," New England Journal of Medicine 367(14):1297-1309.

Rudikoff, S. et al. (Mar. 1982). "Single Amino Acid Substitution Altering Antigen-Binding Specificity," Proc. Natl. Acad. Sci. USA 79:1979-1983.

Sawai, H. et al. (1995). "Direct Production of the Fab Fragment Derived From the Sperm Immobilizing Antibody Using Polymerase Chain Reaction and cDNA Expression Vectors," American Journal of Reproductive Immunology 34 (1):26-34.

Schiele, F. et al. (2013). "A Specific Antidote for Dabigatran: Functional and Structural Characterization," Blood 121 (18):3554-3562.

Sillen, H. et al. (2010, e-pub. Jun. 25, 2010). "Determination of Ticagrelor and Two Metabolites in Plasma Samples by Liquid Chromatography and Mass Spectrometry," Journal of Chromatography B 878(25):2299-2306.

Sillen, H. et al. (2011, e-pub. Jun. 21, 2011). "Determination of Unbound Ticagrelor and Its Active Metabolite (AR-C124910XX) in Human Plasma by Equilibrium Dialysis and LC-MS/MS," Journal of Chromatography B 879 (23):2315-2322.

Springthorpe, B. et al. (Nov. 1, 2007). "From ATP to AZD6140: The Discovery of an Orally Active Reversible P2Y12 Receptor Antagonist for the Prevention of Thrombosis," Bioorganic & Medicinal Chemistry Letters 17(21):6013-6018.

Storey, R.F. et al. (Nov. 6, 2007). "Inhibition of Platelet Aggregation by AZD6140, A Reversible Oral P2Y12 Receptor Antagonist, Compared With Clopidogrel in Patients With Acute Coronary Syndromes," Journal of the American College of Cardiology 50(19)1852-1856.

Storey, R.F. et al. (Oct. 26, 2010). "Inhibitory Effects of Ticagrelor Compared With Clopidogrel on Platelet Function in Patients With Acute Coronary Syndromes: The PLATO (PLATelet Inhibition and Patient Outcomes) PLATELET Substudy," Journal of the American College of Cardiology 56(18):1456-1462.

Tantry, U.S. et al. (2013). "Consensus and Update on the Definition of On-Treatment Platelet Reactivity to Adenosine Diphosphate Associated With Ischemia and Bleeding," Journal of the American College of Cardiology 62 (24):2261-2273.

Taylor, G. et al. (May 2013). "Is Platelet Transfusion Efficient to Restore Platelet Reactivity in Patients Who Are Responders to Aspirin and/or Clopidogrel Before Emergency Surgery?" The Journal of Trauma and Acute Care Surgery 74(5):1367-1369.

Teng, R. et al. (2016). "Effects of Autologous Platelet Transfusion on Platelet Inhibition in Ticagrelor-Treated and Clopidogrel-Treated Subjects," Journal of Thrombosis and Haemostasis 14(12):2342-2352.

Teng, R. et al. (Dec. 2013, e-pub. Dec. 18, 2012). "Evaluation of the Pharmacokinetics and Pharmacodynamics of Ticagrelor Co-Administered With Aspirin in Healthy Volunteers," Platelets 24(8):615-624.

Teng, R. et al. (Sep. 2010). "Absorption, Distribution, Metabolism, and Excretion of Ticagrelor in Healthy Subjects," Drug Metabolism & Disposition 38(9):1514-1521.

Thiele, T. et al. (May 2012). "Platelet Transfusion for Reversal of Dual Antiplatelet Therapy in Patients Requiring Urgent Surgery: A Pilot Study," Journal of Thrombosis and Haemostasis 10(5):968-971.

Thompson, J. et al. (Feb. 16, 1996). "Affinity Maturation of a High-affinity Human Monoclonal Antibody Against the Third Hypervariable Loop of Human Immunodeficiency Virus: Use of Phage Display to Improve Affinity and Broaden Strain Reactivity," Journal of Molecular Biology 256(1):77-88.

Valgimigli, M. et al. (2018). "2017 ESC Focused Update on Dual Antiplatelet Therapy in Coronary Artery Disease Developed in Collaboration With EACTS: The Task Force for Dual Antiplatelet Therapy in Coronary Artery Disease if the European Society of Cardiology (ESC) and of the European Association for Cardio-Thoracic Surgery (EACTS)," European Heart Journal 39(3):213-254.

Van Giezen, J.J.J. et al. (Sep. 2009). "Ticagrelor Binds to Human P2Y (12) Independently From ADP But Antagonizes ADP-induced Receptor Signaling and Platelet Aggregation," Journal of Thrombosis and Haemostasis (7) 9:1556-1565.

Vonrhein, C. et al. (Apr. 2011). "Data Processing and Analysis With The AutoPROC Toolbox," Acta Crystallographica Section D 67(4):293-302.

Wallentin, L. et al. (Sep. 10, 2009). "Ticagrelor Versus Clopidogrel in Patients With Acute Coronary Syndromes," The New England Journal of Medicine 361(11):1045-1057.

Wiviott, S.D. et al. (Aug. 17, 2013). "Prasugrel Versus Clopidogrel for Patients With Unstable Angina or Non-ST-segment Elevation Myocardial Infarction With or Without Angiography: A Secondary, Prespecified Analysis of the Trilogy ACA Trial," The Lancet 382(9892):605-613.

Wiviott, S.D. et al. (Nov. 15, 2007). "Prasugrel versus Clopidogrel in Patients with Acute Coronary Syndromes," New England Journal of Medicine 357(20):2001-2015.

Young, N.M. et al. (Dec. 18, 1995). "Thermal Stabilization of a Single-Chain Fv Antibody Fragment by Introduction of a Disulphide Bond," FEBS Letters 377(2):135-139.

Yusuf, S. et al. (Aug. 16, 2001). "Effects of Clopidogrel in Addition to Aspirin in Patients with Acute Coronary Syndromes without ST-Segment Elevation," N Engl J Med. 345(7):494-502.

(56) References Cited

OTHER PUBLICATIONS

Zhang, K. et al. (May 1, 2014). "Structure of the Human P2Y12 Receptor in Complex With an Antithrombotic Drug," Nature 509(7498):115-118, 22 pages.

Zhu, Z. et al. (1997). "Remodeling Domain Interfaces to Enhance Heterodimer Formation," Protein Science 6:781-788.

* cited by examiner

Ticagrelor

Ticagrelor Active Metabolite (TAM)

Ticagrelor Inactive Metabolite (TIM)

Adenosine

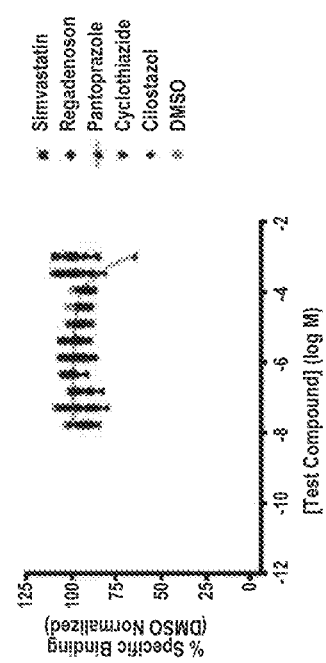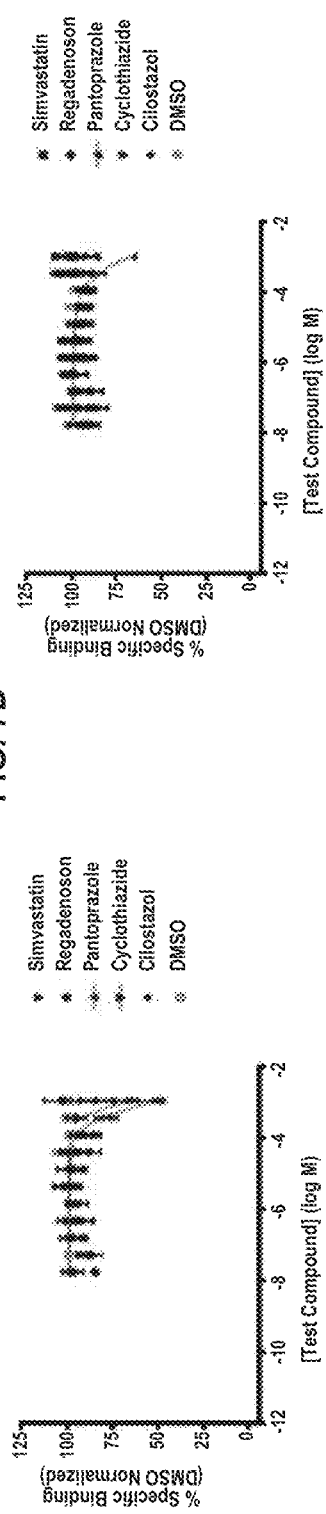
FIG. 7A
FIG. 7B
FIG. 7C
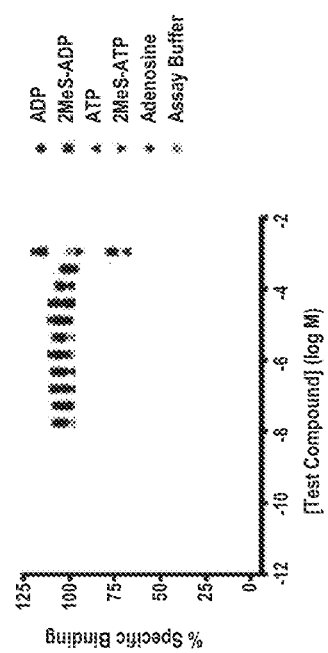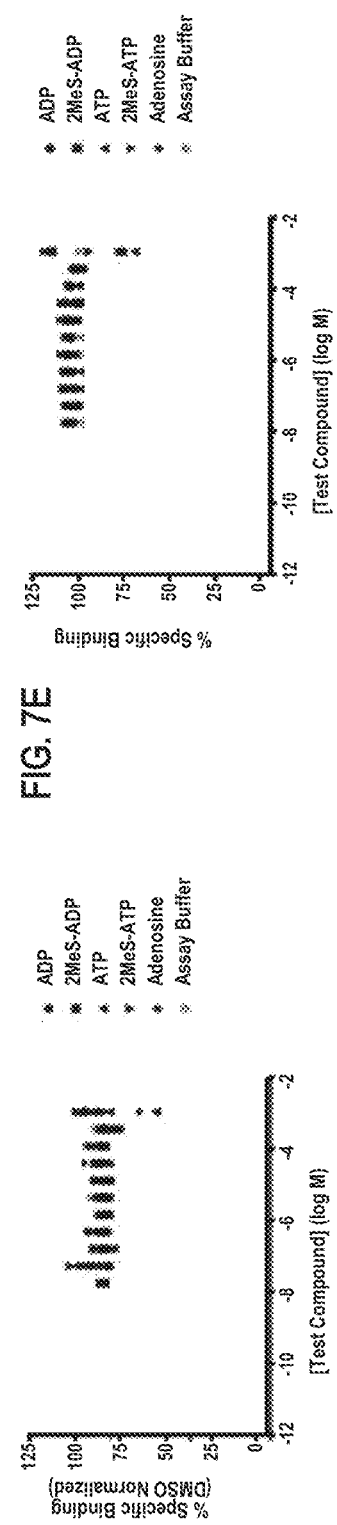
FIG. 7D
FIG. 7E
FIG. 7F
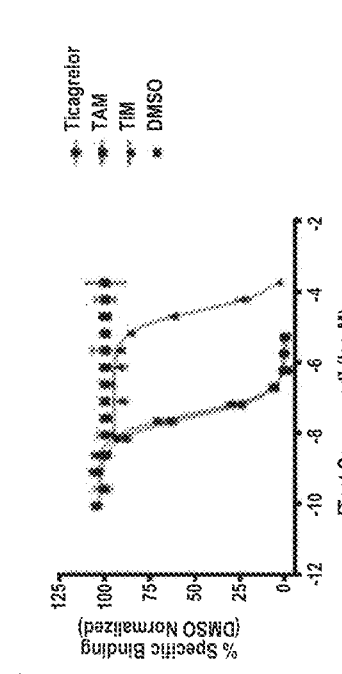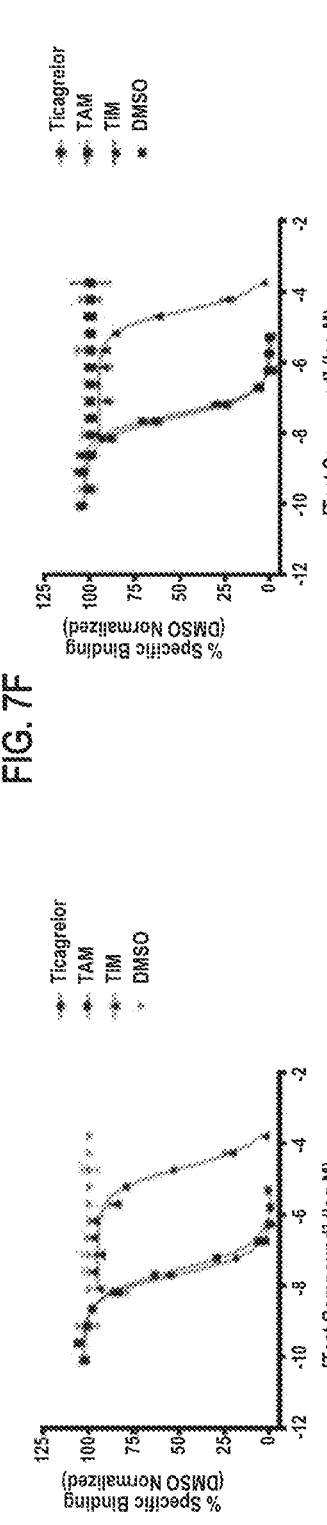

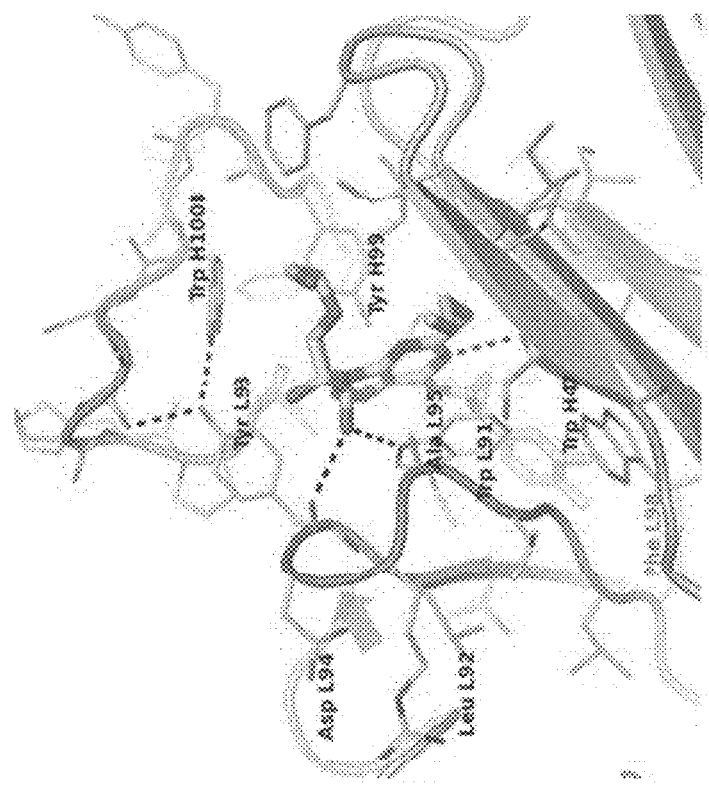
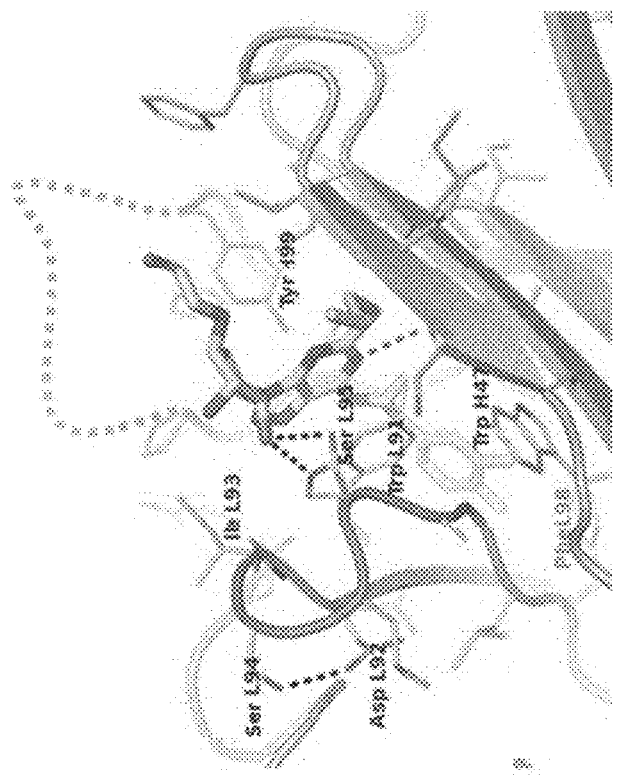
FIG. 10B
FIG. 10A

ANTIBODIES TO TICAGRELOR AND METHODS OF USE

CROSS REFERENCE TO RELATED APPLICATIONS

This application is a divisional of U.S. application Ser. No. 17/176,624, filed Feb. 16, 2021, now U.S. Pat. No. 11,773,186, issued Oct. 3, 2023, which is a divisional of U.S. application Ser. No. 16/035,954, filed Jul. 16, 2018; now U.S. Pat. No. 10,954,308, issued Mar. 23, 2021, which is a divisional of U.S. application Ser. No. 15/966,313, filed Apr. 30, 2018; now abandoned, which is a continuation of U.S. application Ser. No. 14/871,111, filed Sep. 30, 2015, now U.S. Pat. No. 9,982,061, issued May 29, 2018; which claims the benefit of priority to U.S. Provisional Application No. 62/114,931, filed Feb. 11, 2015; and U.S. Provisional Application No. 62/058,458, filed Oct. 1, 2014, the contents of each of which are incorporated by reference in their entireties.

REFERENCE TO AN ELECTRONIC SEQUENCE LISTING

The contents of the electronic sequence listing (691242000111SEQLIST.xml; Size: 77,201 bytes; and Date of Creation: Aug. 15, 2023) is herein incorporated by reference in its entirety.

BACKGROUND

Ticagrelor (BRILINTA™, BRILIQUE™) is an orally active cyclopentyltriazolopyrimidine, a selective and reversibly binding adenosine diphosphate (ADP) receptor antagonist. In patients with acute coronary syndromes (ACS), ticagrelor 90 mg twice daily in combination with low-dose aspirin is approved to reduce major cardiovascular (CV) events. Ticagrelor acts via a dual pathway which mediates both antiplatelet effects ($P2Y_{12}$) and an enhanced adenosine response (ENT-1) (Cattaneo M et al 2014. J Am Coll Cardiol. 63(23): 2503-9). While not yet approved indications, ongoing and planned studies are evaluating ticagrelor for reduction of major CV events in patients with prior myocardial infarction, established peripheral arterial disease, and acute stroke, as well as patients with diabetes and confirmed coronary atherosclerosis.

Ticagrelor has two primary metabolites, ticagrelor active metabolite (TAM) and ticagrelor inactive metabolite (TIM) (Teng et al 2010 Drug Metab. and Dispos. 38: 1514-1521). TAM, also known as AR-C124910XX, is the main circulating metabolite of ticagrelor and is equally effective in $P2Y_{12}$ antagonist activity. TAM typically present at about 30-40% of the parent ticagrelor concentration in patients on BRILINTA/BRILIQUE. Ticagrelor and TAM have circulating half-lives of 8 and 12 hours respectively. TIM, also known as AR-C133913XX, is inactive against $P2Y_{12}$, constitutes <10% of the parent ticagrelor, is undetectable after 8 hours, and is the main metabolite excreted via the urine.

The PLATelet inhibition and patient Outcomes (PLATO) trial has demonstrated greater efficacy of ticagrelor without an increase in total major bleeding when compared with clopidogrel in a broad ACS patient population (UA, NSTEMI, STEMI) regardless of management strategy (medically or invasively managed) (Wallentin et al 2009 NEJM 361 (11): 1045-1057). As with all antiplatelet agents, however, there exists the potential for bleeding in patients using ticagrelor. There are limited treatment options if severe bleeding occurs in patients on dual antiplatelet therapy (DAPT). If a bleeding event occurs in a patient on DAPT, platelet transfusions or administration of coagulation factors may be use in an attempt to augment haemostasis. However, currently no clinical data exist that evaluates the haemostatic benefit of platelet transfusions or use of recombinant Factor VIIa after or during a major bleeding event in subjects on ticagrelor (Dalen M et al 2013 J Cardiothorac Vasc Anesth. 27(5): e55-7).

Accordingly, the availability of an antidote, such as a ticagrelor-specific neutralizing antibody, would allow better clinical management of the balance between the desired antithrombotic effect versus control of bleeding. Since ticagrelor is the only marketed reversibly binding platelet inhibitor an antibody may provide reversal of platelet inhibition without the need for fresh platelet transfusions, thus avoiding hazards associated with platelet transfusions. The availability of an agent that overcomes the inhibition of ADP-induced platelet aggregation associated with ticagrelor and TAM would fulfill an important unmet clinical need, for example in patients who experience major bleeding or who require urgent surgery.

SUMMARY OF THE DISCLOSURE

In an aspect the disclosure relates to an antibody that specifically binds a cyclopentyltriazolopyrimidine compound of the Formula (Ia):

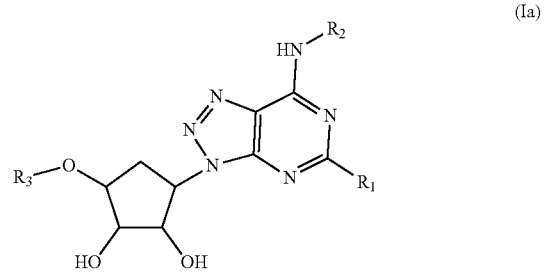

(Ia)

wherein
$R_1$ is selected from the group consisting of $C_1$-$C_6$ alkoxy and $C_1$-$C_6$ alkylthio;
$R_2$ is selected from the group consisting of H, $C_1$-$C_6$ alkyl, substituted $C_1$-$C_6$ alkyl, $C_1$-$C_6$ cycloalkyl, and substituted $C_3$-$C_6$ cycloalkyl; and
$R_3$ is selected from the group consisting of H. $C_1$-$C_6$ alkyl, $C_1$-$C_6$ alkoxy, and $C_1$-$C_6$ alkanol.

In some embodiments, the antibody binds to an epitope within the portion of the compounds identified by brackets as Formula (IIa)

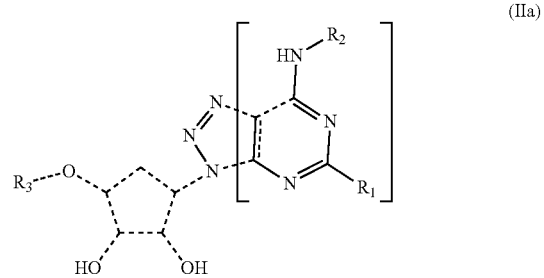

(IIa)

wherein $R_1$, $R_2$, and $R_3$ are defined as above.

In further embodiments, the antibody binds to an epitope within the portion of the compounds identified by brackets as Formula (IIIa)

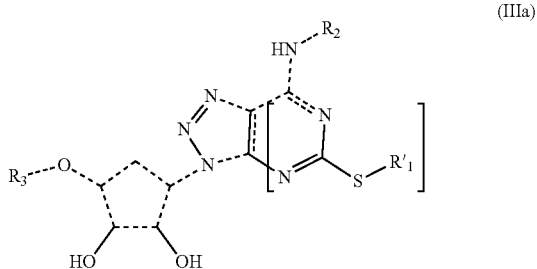

wherein $R_2$, and $R_3$ are defined as above and $R'_1$ is selected from the group consisting of $C_1$-$C_4$ alkyl.

In further embodiments, the antibody binds to a compound selected from the group consisting of:

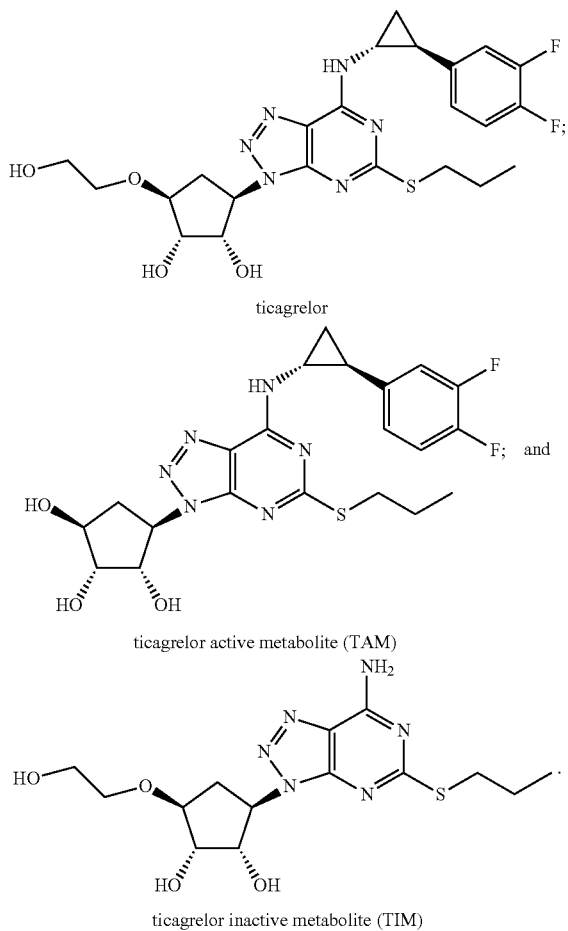

ticagrelor ticagrelor active metabolite (TAM)

ticagrelor inactive metabolite (TIM)

In further embodiments of the above aspects and embodiments, the antibody or a fragment thereof comprises a heavy chain variable region (VH) sequence selected from the group consisting of SEQ ID NO:2, SEQ ID NO:12, SEQ ID NO:22, SEQ ID NO:32, SEQ ID NO:42, SEQ ID NO:52, SEQ ID NO:62, and SEQ ID NO:72; and a light chain variable region (VL) sequence selected from the group consisting of SEQ ID NO:7, SEQ ID NO:17, SEQ ID NO:27, SEQ ID NO:37, SEQ ID NO:47, SEQ ID NO:57, SEQ ID NO:67, and SEQ ID NO:77. In some embodiments, the antibody comprises a combination of VH and VL sequences selected from the group consisting of SEQ ID NO:2 and SEQ ID NO:7; SEQ ID NO: 12 and SEQ ID NO:17; SEQ ID NO:22 and SEQ ID NO:27; SEQ ID NO:32 and SEQ ID NO:37: SEQ ID NO:42 and SEQ ID NO:47; SEQ ID NO:52 and SEQ ID NO:57; SEQ ID NO:62 and SEQ ID NO:67; and SEQ ID NO:72 and SEQ ID NO:77. In further embodiments, the antibody comprises a combination of VH and VL selected from the group consisting of SEQ ID NO:52 and SEQ ID NO:57; SEQ ID NO:62 and SEQ ID NO:67; and SEQ ID NO:72 and SEQ ID NO:77.

In further embodiments of the above aspects and embodiments, the antibody or a fragment thereof comprises framework regions (FR) and complementarity-determining regions (CDRs) 1, 2, and 3 of a heavy chain variable region and a light chain variable region, wherein the CDR1, CDR2, and CDR3 sequences of the heavy chain variable region comprise, SEQ ID NO:3 (CDR1), SEQ ID NO:4 (CDR2), and SEQ ID NO:5 (CDR3); SEQ ID NO:13 (CDR1), SEQ ID NO:14 (CDR2), and SEQ ID NO:15 (CDR3); SEQ ID NO:23 (CDR1), SEQ ID NO:24 (CDR2), and SEQ ID NO:25 (CDR3); SEQ ID NO:33 (CDR1), SEQ ID NO:34 (CDR2), and
SEQ ID NO:35 (CDR3); SEQ ID NO:43 (CDR1), SEQ ID NO:44 (CDR2), and SEQ ID NO:45 (CDR3); SEQ ID NO:53 (CDR1), SEQ ID NO:54 (CDR2), and SEQ ID NO:55 (CDR3); SEQ ID NO:63 (CDR1), SEQ ID NO:64 (CDR2), and SEQ ID NO:65 (CDR3); or SEQ ID NO:73 (CDR1), SEQ ID NO:74 (CDR2), and SEQ ID NO:75 (CDR3); and wherein the CDR1, CDR2. and CDR3 sequences of the light chain variable region comprise, SEQ ID NO:8 (CDR1). SEQ ID NO:9 (CDR2), and SEQ ID NO:10 (CDR3); SEQ ID NO:18 (CDR1), SEQ ID NO:19 (CDR2), and SEQ ID NO:20 (CDR3); SEQ ID NO:28 (CDR1), SEQ ID NO:29 (CDR2), and SEQ ID NO:30 (CDR3); SEQ ID NO:38 (CDR1), SEQ ID NO:39 (CDR2), and SEQ ID NO:40 (CDR3); SEQ ID NO:48 (CDR1), SEQ ID NO:49 (CDR2), and SEQ ID NO:50 (CDR3); SEQ ID NO:58 (CDR1), SEQ ID NO:59 (CDR2), and SEQ ID NO:60 (CDR3); SEQ ID NO:68 (CDR1), SEQ ID NO:69 (CDR2), and SEQ ID NO:70 (CDR3); or SEQ ID NO:78 (CDR1), SEQ ID NO:79 (CDR2), and SEQ ID NO:80 (CDR3). In further embodiments, the antibody comprises a combination of CDR regions selected from the group consisting of: SEQ ID NO:53 (VH CDR1). SEQ ID NO:54 (VH CDR2), SEQ ID NO:55 (VH CDR3). SEQ ID NO:58 (VL CDR1), SEQ ID NO:59 (VL CDR2), and SEQ ID NO:60 (VL CDR3); SEQ ID NO:63 (VH CDR1), SEQ ID NO:64 (VH CDR2). SEQ ID NO:65 (VH CDR3), SEQ ID NO:68 (VL CDR1), SEQ ID NO:69 (VL CDR2), and SEQ ID NO:70 (VL CDR3); and SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3).

In the above aspect and embodiments, the antibody is selected from a polyclonal antibody, a monoclonal antibody, a humanized antibody, a human antibody, a single chain Fv (scFv), a single domain antibody, a Fab, a F(ab')$_2$, a single chain diabody, an antibody mimetic. and an antibody variable domain. In some embodiments, the antibody comprises a scFv. In some embodiments, the antibody comprises a Fab.

In some embodiments, the antibody described above binds to ticagrelor or ticagrelor active metabolite (TAM).

In further embodiments, the antibody binds ticagrelor or a metabolite or derivative thereof with an $IC_{50}$ of about 200 nM or lower. In yet further embodiments, the antibody binds ticagrelor or a metabolite or derivative thereof with an $IC_{50}$ of about 100 nM to about 1 nM, or with an $IC_{50}$ of about 10 nM to about 1 nM.

In further embodiments the antibody binds ticagrelor or a metabolite or derivative thereof with a KD of about 50 nM or lower. In yet further embodiments, the antibody binds ticagrelor or a metabolite or derivative thereof with a KD in a range of about 250 pM to about 1 pM. or in a range of about 100 pM to about 1 pM.

In further embodiments the antibody binds ticagrelor or a metabolite or derivative thereof and does not bind to a compound selected from the group consisting of fenofibrate, nilvadipine, cilostazol, bucladesine, regadenoson, cyclothiazide, cyfluthrin, lovastatin, linezolid, simvastatin, cangrelor, pantoprazole, adenosine, adenosine diphosphate, adenosine triphosphate, 2-MeS adenosine diphosphate, and 2-MeS adenosine triphosphate. In embodiments, the antibody does not inhibit the activity of a compound selected from the group consisting of fenofibrate, nilvadipine, cilostazol, bucladesine, regadenoson, cyclothiazide, cyfluthrin, lovastatin, linezolid, simvastatin, cangrelor, pantoprazole, adenosine, adenosine diphosphate, adenosine triphosphate, 2-MeS adenosine diphosphate, and 2-MeS adenosine triphosphate. In further embodiments, the antibody exhibits an $IC_{50}$ of at least about 1000 UM for a compound selected from the group consisting of fenofibrate, nilvadipine, cilostazol, bucladesine, regadenoson, cyclothiazide, cyfluthrin, lovastatin, linezolid, simvastatin, cangrelor, pantoprazole, adenosine, adenosine diphosphate, adenosine triphosphate, 2-MeS adenosine diphosphate, and 2-MeS adenosine triphosphate.

In some embodiments, the antibody has an in vivo half-life of about 4-12 hours. In specific embodiments the antibody has an in vivo half-life if about 12 hours.

In some embodiments, the antibody neutralizes the antiplatelet effect of ticagrelor or the active metabolite of ticagrelor. In further embodiments, the antibody neutralizes the antiplatelet effect of ticagrelor or the active metabolite of ticagrelor within about 60 minutes of administration.

In some embodiments, the antibody has an off-rate for ticagrelor or the active metabolite of ticagrelor that allows for continuation of commencement of a therapy comprising ticagrelor.

In other aspects, the disclosure provides a method of treating acute bleeding in a patient who is in need of treatment, comprising administering to the patient an effective amount of the antibody disclosed herein. In some embodiments of the method the patient has undergone or is undergoing a surgical procedure and who has been administered ticagrelor. In some embodiments of the method the patient is in need of urgent care and/or emergency trauma management.

Other aspects of the disclosure provide for a composition comprising the antibody of any of the preceding aspects and embodiments in combination with a pharmaceutically acceptable carrier.

Some additional aspects provide a nucleic acid molecule comprising a nucleotide sequence encoding an antibody according to of any of the preceding claims. In some embodiments the nucleic acid molecule comprises SEQ ID NO: 1, SEQ ID NO:6, SEQ ID NO:11, SEQ ID NO:16, SEQ ID NO:21, SEQ ID NO:26, SEQ ID NO:31, SEQ ID NO:36, SEQ ID NO:41, SEQ ID NO:46, SEQ ID NO:51, SEQ ID NO:56, SEQ ID NO:61, SEQ ID NO:66, SEQ ID NO:71, and SEQ ID NO:76.

Further aspects of the disclosure provide for compositions, vectors, and host cells that may comprise at least one nucleic acid molecule disclosed herein. In some embodiments the compositions, vectors, and host cells comprise a first nucleic acid molecule and a second nucleic acid molecule that encode one or more of the proteins disclosed herein.

Other aspects will be apparent to one of skill in the art upon review of the description and exemplary depictions that follow.

BRIEF DESCRIPTION OF THE DRAWINGS

For the purpose of illustrating the disclosure, there are depicted in the drawings certain aspects of the disclosure. However, the disclosure is not limited to the precise arrangements and instrumentalities of the aspects depicted in the drawings.

(FIG. 2A) Provides the chemical structure of ticagrelor, ticagrelor active metabolite (TAM), ticagrelor inactive metabolite (TIM) and adenosine. The unique R groups, di-fluorophenyl-cyclopropyl and thiopropyl substituents, are highlighted with a dotted line. (FIG. 2B) Specificity profile for TICA0072. (FIG. 2C) Specificity profile for TICA0212 (MEDI 2452). Specificity profiles include ticagrelor, TAM, TIM, adenosine, ADP, ATP and three of the twelve related compounds of FIG. 4 (for clarity; no binding was detected to any of the twelve compounds at concentrations up to 0.1 mM). Data is mean and SEM for three triplicates.

FIG. 5A-C: Competition of TICA0049 Fab binding to biotinylated ticagrelor by compounds listed. FIG. 5D-F: Competition of TICA0072 Fab binding to biotinylated ticagrelor by compounds listed. Data DMSO normalised.

FIG. 7A-F shows the results of Selectivity studies for TICA0162 and TICA0212 Fab. FIG. 7A-C: Competition of TICA0162 Fab binding to biotinylated ticagrelor by compounds listed. FIG. 7D-F: Competition of TICA0212 Fab binding to biotinylated ticagrelor by compounds listed. Data DMSO normalised.

(FIG. 8A) TICA0212/MEDI2452 1uM ticagrelor (▲) or 1 uM TAM (●) mediated inhibition of 20 μM ADP-induced aggregation. (FIG. 8B) TICA0212/MEDI2452 shows reduction of free ticagrelor concentration in plasma in the presence of 1 uM ticagrelor. Mean (n=5)±standard error of the mean. (FIG. 8C) TICA0072 reversal of ticagrelor and TAM inhibition of $P2Y_{12}$ signalling.

FIG. 10A-B shows partial views of the crystal structures of TICA0072 (FIG. 10A) and TICA0212/MEDI2452 (FIG. 10B) in complex with ticagrelor. The Fabs are shown in ribbon representation with amino acid residues within 7 Å from ticagrelor shown as sticks. Some main chain atoms were omitted for clarity. Light chains are shown in beige and heavy chain in light blue. CDR3s from both chains are coloured green. VH CDR3 could not be modelled in the TICA0072 structure and a tentative location is drawn as a dashed line. The orange arrow indicates the shift in Vl. CDR3 observed in TICA0212/MEDI2452 compared to TICA0072. Residues are number following kabat and are prefixed with L or H to indicate light or heavy chain.

(FIG. 11A) Individual data for each treatment group post stop of ticagrelor infusion. Vehicle control (■), ticagrelor alone (●), ticagrelor+TICA0212/MEDI2452 (o) and ticagrelor+isotype control (Δ). Bar represents mean data (n=4). AU=aggregation units. At 15 minutes data was only collected for the ticagrelor+TICA0212/MEDI2452 group. (FIG. 11B) Percentage reversal induced by TICA0212/MEDI2452, mean data (n=4) ±SEM (FIG. 12A)

Figure 1:
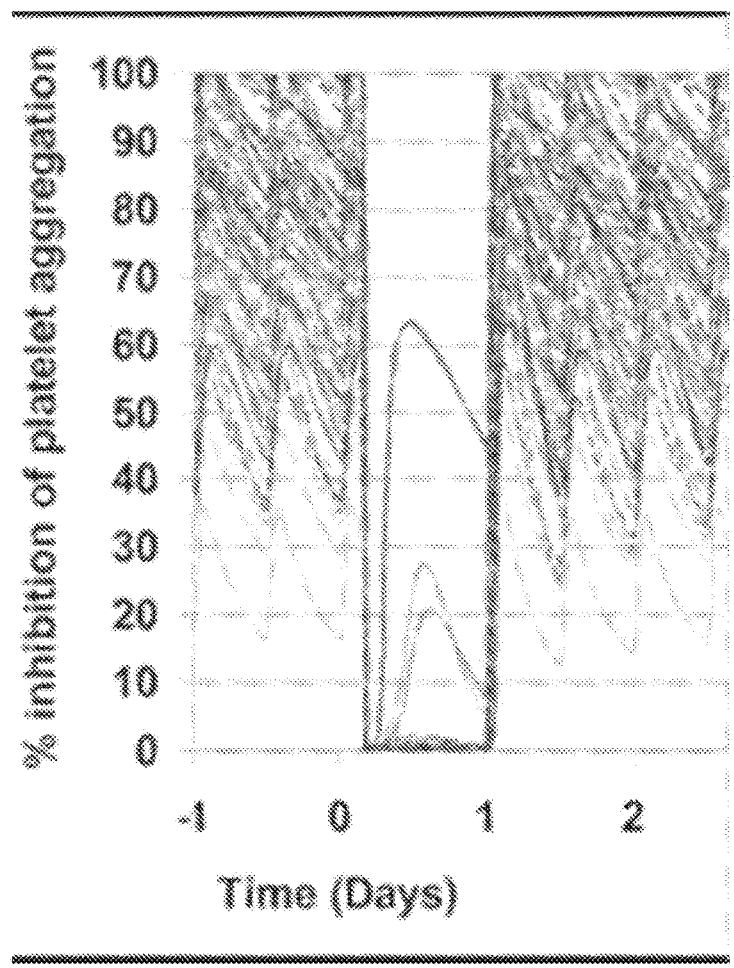
FIG. 1 depicts PK/PD modelling of ticagrelor-neutralizing Fab based on Phase III PLATO data. Following a ticagrelor 180-mg loading dose and 90 mg twice daily, neutralizing Fab is added at time zero. Patients are restarted on ticagrelor on day 1. The Fab is predicted to rapidly neutralize ticagrelor and the TAM, thus restoring platelet aggregation in 99% of patients. The 'hill' between days 0 and 1 represents the redistribution of ticagrelor from other tissues in the 1% of patients in whom ticagrelor is cleared more slowly.

Individual data for total blood loss and (FIG. 12B) for total bleeding time. Vehicle control (■), ticagrelor alone (●) and ticagrelor+TICA0212/MEDI2452 (o). Bar represents mean data (n=12).

DETAILED DESCRIPTION

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The numbering of amino acids in the variable domain, complementarity determining region (CDRs) and framework regions (FR), of an antibody follow, unless otherwise indicated, the Kabat definition as set forth in Kabat et al. Sequences of Proteins of Immunological Interest, 5th Ed. Public Health Service, National Institutes of Health, Bethesda, MD. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

As used herein, the terms "antibody" and "antibodies", also known as immunoglobulins, encompass monoclonal antibodies (including full-length monoclonal antibodies), polyclonal antibodies, multispecific antibodies formed from at least two different epitope binding fragments (e.g., multispecifc antibodies, e.g., PCT publication WO2009018386, PCT Application No. PCT/US2012/045229, incorporated herein by reference in its entirety), biMabs, human antibodies, humanized antibodies, camelised antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. In particular embodiments provided herein, antibodies relate to active binding fragments of an antibody, i.e., molecules that contain at least one antigen-binding site such as, for example scFv and Fab. Antibodies also include peptide fusions with antibodies or portions thereof such as a protein fused to an Fe domain. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, etc., or other animals such as birds (e.g. chickens).

As used herein, $C_1$-$C_6$ alkyl refers to straight chain and branded alkyls having one to six carbon atoms, and includes, methyl, ethyl, propyl, n-butyl, iso-butyl, pentyl, isopentyl, neopentyl, and hexyl.

As used herein, $C_1$-$C_6$ alkoxy refers to an alkyl, as noted above, having an oxygen in the group. In some embodiments, the oxygen atom is located at the position that attaches the substituent group to the core structure (i.e., ring structure).

As used herein, $C_1$-$C_6$ alkylthio refers to an alkyl, as noted above, having a sulfur in the group. In some embodiments, the sulfur atom is located at the position that attaches the substituent group to the core structure (i.e., ring structure).

As used herein, $C_1$-$C_6$ alkanol refers to an alkyl, as noted above, having a hydroxyl group at the terminal end of the substituent structure.

As used herein, $C_3$-$C_6$ cycloalkyl refers to cyclopropyl, cyclobutyl, cyclopentyl, and cyclohexyl.

As used herein, "substituted" $C_3$-$C_6$ cycloalkyl and $C_1$-$C_6$ alkyl refer to the alkyl and cycloalkyl groups discussed above which are substituted on at least one carbon atom with an aryl group that is also substituted with 1-3 halogen atoms.

As used herein, "ticagrelor" refers to the reversible $P2Y_{12}$ inhibitor ((1S,2S,3R,5S)-3-[7-{[(1R,2S)-2-(3,4-difluorophenyl)cyclopropyl]amino}-5-(propylthio)-3H-[1,2,3]triazolo[4,5-d]pyrimidin-3-yl]-5-(2-hydroxyethoxy)cyclopentane-1,2-diol) and having the chemical structure:

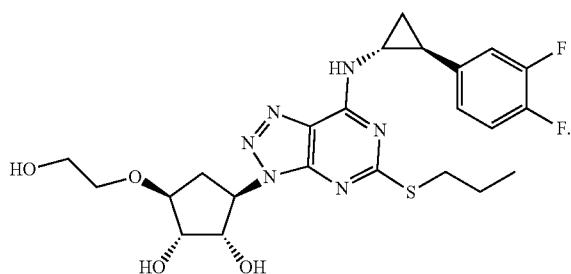 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

As used herein, "ticagrelor active metabolite" or "TAM" refers to the major active metabolite of ticagrelor, also referred to as AR-C124910XX, a reversible $P2Y_{12}$ inhibitor and having the chemical structure:

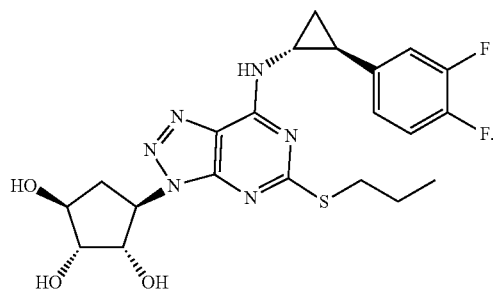 [SMILES: CCCSc1nc(N[C@@H]2C[C@H]2c2ccc(F)c(F)c2)c2nnn([C@@H]3C[C@H](O)[C@@H](O)[C@H]3O)c2n1]

As used herein, "ticagrelor inactive metabolite" or "TIM" refers to an inactive metabolite of ticagrelor, also referred to as AR-C133913XX, and having the chemical structure:

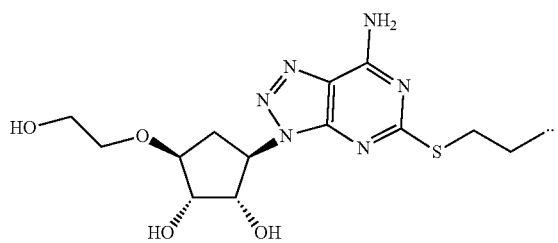

Antibodies

In a general sense, the disclosure provides novel antibodies that bind a cyclopentyltriazolopyrimidine compound of the Formula (Ia):

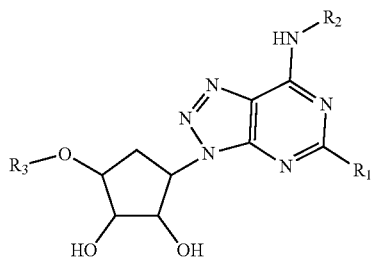

wherein
$R_1$ is selected from the group consisting of $C_1$-$C_6$ alkoxy and $C_1$-$C_6$ alkylthio;
$R_2$ is selected from the group consisting of H, $C_1$-$C_6$ alkyl, substituted $C_1$-$C_6$ alkyl, $C_3$-$C_6$ cycloalkyl, and substituted $C_3$-$C_6$ cycloalkyl; and
$R_3$ is selected from the group consisting of H, $C_1$-$C_6$ alkyl, $C_1$-$C_6$ alkoxy, and $C_1$-$C_6$ alkanol.

In particular embodiments, the antibodies specifically bind a compound selected from the from the group consisting of:

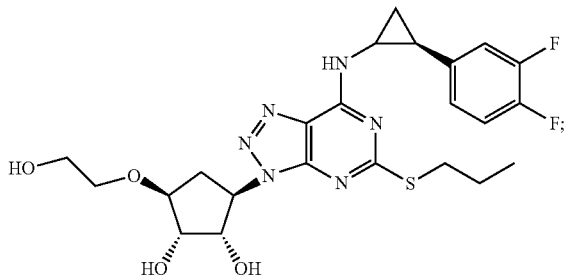

ticagrelor

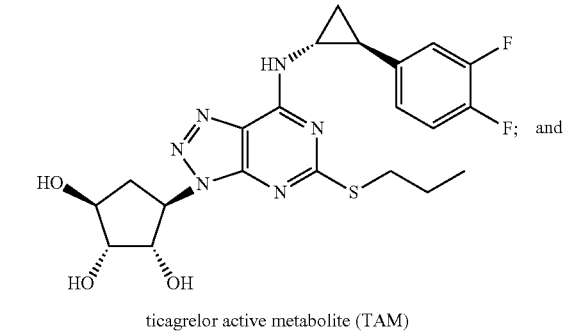

ticagrelor active metabolite (TAM)

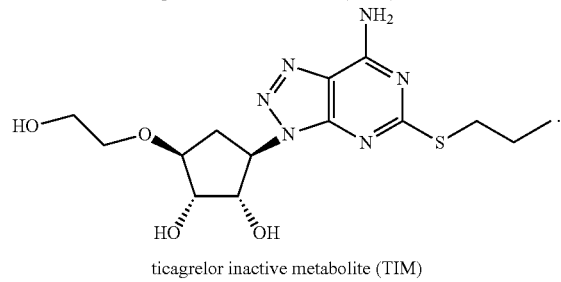

ticagrelor inactive metabolite (TIM)

In particular aspects, the disclosure provides an antibody that binds to ticagrelor and TAM with any one or more of the following features including high binding specificity, high binding affinity, rapid time to onset, and rapid time to offset (e.g., allowing for the optional continuation of or co-administration of therapy comprising ticagrelor).

In some embodiments, the antibody binds to ticagrelor and neutralizes the anti-platelet aggregation activity of ticagrelor and TAM, thus restoring ADP-induced platelet aggregation in the presence of ticagrelor and TAM.

In some embodiments, the antibody half-life in a subject is about the same as the half-life of ticagrelor and TAM. In some embodiments the antibody half-life is from about 4-24 hours (e.g., 4, 5, 6, 7, 8, 9, 10, 11, 12, 13, 14, 15, 16, 17, 18, 19, 20, 21, 22, 23, or 24 hours). In some embodiments the antibody half-life is from about 4-12 hours (e.g., 4, 5, 6, 7, 8, 9, 10, 11, or 12 hours).

In some embodiments, the antibody provides for a rapid onset of activity. For example, in embodiments the antibody time to onset or the time to neutralize ticagrelor and TAM mediated platelet inhibition, is from about 15-120 minutes, or from about 15-60 minutes. In some embodiments, the time to onset is less than 60 minutes.

In some embodiments the antibody has a PK/PD profile that provides for a rapid offset of activity, such that, for example, a subject who has been administered the antibody may recommence with the prescribed ticagrelor therapy. In some embodiments, a subject who has received an antibody disclosed herein (e.g., by i.v. infusion) may receive or restart ticagrelor therapy within twenty-four hours following the administration of the antibody.

As discussed and exemplified in certain embodiments herein, the antibody binds ticagrelor or a metabolite thereof and does not bind to other structurally related compounds, or compounds that may be administered with ticagrelor as a cotherapy. For example, suitably, the antibody does not inhibit the activity of a compound selected from the group consisting of fenofibrate, nilvadipine, cilostazol, bucladesine, regadenoson, cyclothiazide, cyfluthrin, lovastatin, linezolid, simvastatin, cangrelor, pantoprazole, adenosine, adenosine diphosphate, adenosine triphosphate, 2-MeS adenosine diphosphate, and 2-MeS adenosine triphosphate.

The antibodies described herein can comprise antigen binding fragments containing only select portions of an antibody molecule, such as Fab, F(ab')2, Fab', scFv, di-scFv, sdAb fragments, and may be used as diagnostic or therapeutic agents. In addition, specific residues in the variable domains may be altered to improve binding specificity and/or stability of antibodies and antibody fragments. Other residues not directly involved in antigen binding have been replaced in order to "humanize" regions of non-human antibodies and reduce immunogenicity of the antibody.

In certain aspects, the antibody is a Fab fragment, for example, a Fab fragment of an antibody or a recombinantly produced antigen binding fragment comprising a variable light chain (VL), a constant light chain (CL), a variable heavy chain (VH), and a constant heavy chain portion (CH1). Optionally, the light and heavy chains of the Fab may be interconnected via one or more disulfide linkages such as, for example, via a suitable antibody hinge region. As described herein, the Fab binds to an epitope of a compound of the cyclopentyltriazolopyrimidine class of oral active agents. In some embodiments the Fab binds to ticagrelor or a metabolite thereof.

In certain aspects, the Fab may be derived from or based on the sequence of an antibody, such as a conventional murine, humanized or human antibody. In certain aspects, the Fab may be derived from or based on one or more scFvs, such as scFvs screened and derived from a library. In such embodiments, the Fab derived from or based on the sequence of a conventional antibody or scFv retains one or more functional activities of the conventional antibody (e.g., retains at least 80% or more (80%, 85%, 90%, 95%, 97%, 98%, 99% or 100%) of a functional activity). For example, in certain aspects, the Fab retains one or more of the affinity for antigen (e.g., ticagrelor), inhibitory activity, and/or selectivity of the antibody or scFv.

While the Fab fragment may comprise a sequence that binds to an epitope of a cyclopentyltriazolopyrimidine, in certain embodiments, the Fab binds to ticagrelor. In some aspects, the Fab binds to the active metabolite of ticagrelor. In certain aspects, the Fab may bind to both ticagrelor and the active metabolite of ticagrelor.

In some embodiments the Fab may comprise a combination of CDR regions from different antibodies that bind to ticagrelor or the active metabolite thereof.

In certain aspects, the Fab comprises a light chain portion (VL) comprising the amino acid sequence set forth in any of SEQ ID NO:7. SEQ ID NO:17, SEQ ID NO:27, SEQ ID NO:37. SEQ ID NO:47, SEQ ID NO:57, SEQ ID NO:67, and SEQ ID NO:77. In further embodiments the Fab comprises a light chain portion comprising the amino acid sequence set forth in any of SEQ ID NO:57, SEQ ID NO:67, and SEQ ID NO:77. In certain aspects, the Fab comprises a heavy chain portion (VH) comprising the amino acid as set forth in any of SEQ ID NO:2, SEQ ID NO: 12, SEQ ID NO:22, SEQ ID NO:32. SEQ ID NO:42, SEQ ID NO:52, SEQ ID NO:62, and SEQ ID NO:72. In further embodiments, the Fab comprises a heavy chain portion comprising the amino acid sequence set forth in any SEQ ID NO:52, SEQ ID NO:62, and SEQ ID NO:72. In certain aspects, the Fab is encoded by a nucleotide sequence encoding the light chain portion (VL) and a nucleotide sequence encoding the heavy chain portion (VH), for example, a nucleotide sequence comprising the nucleic acid sequence set forth in SEQ ID NO:1, SEQ ID NO:11, SEQ ID NO:21, SEQ ID NO:31, SEQ ID NO:41, SEQ ID NO:51, SEQ ID NO:61, or SEQ ID NO:71; and a nucleotide sequence comprising the nucleic acid sequence as set forth in SEQ ID NO:6, SEQ ID NO:16, SEQ ID NO:16, SEQ ID NO:16, SEQ ID NO:16, SEQ ID NO:16, SEQ ID NO:16, or SEQ ID NO:76.

In certain aspects, the antibody may be an scFv. It is understood that an scFv encompasses a polypeptide chain comprising a variable heavy chain domain (VH) linked to a variable light chain domain (VL) via a flexible polypeptide linker. In some aspects the polypeptide linker between VH and VL comprises a protease cleavage site. The VH and VL domains of the scFv may be derived from the same or from different antibodies. In some aspects, a VH or VL of the scFv may comprise one or more CDRs which bind to a target of interest, while the remainder of the VH or VL domain is derived from a different antibody or is synthetic. In some aspects, the scFv comprises at least one CDR of an antibody, e.g., an antibody with binding activity to ticagrelor or a metabolite thereof. In some aspects, the scFv comprises at least two CDRs of a given antibody. In some aspects, the scFv comprises at least three CDRs of a given antibody. In some aspects, the scFv comprises at least four CDRs of a given antibody. In some aspects, the scFv comprises at least five CDRs of a given antibody. In some aspects, the scFv comprises at least six CDRs of a given antibody.

Several methodologies can be used alone or in combination to improve the stability of a scFv molecule. One methodology that can be used, alone or in combination with one or more of the other methodologies, is engineering the length and/or composition of the linker connecting the scFv domains to stabilize the scFv portion.

Another potential methodology that can be used, alone or in combination with one or more of the other methodologies described herein, is by introducing at least two amino acid substitutions (also referred to as modifications or mutations) into the VH and/or VL domains of the scFv so as to promote disulfide bond formation (see for example Brinkmann et al., 1993, PNAS. 90: 7538-42; Zhu et al., 1997, Prot. Sci. 6: 781-8; Reiter et al., 1994, Biochem. 33: 5451-9; Reiter et al., 1996, Nature 14: 1239-45; Luo et al., 1995, J. Biochem. 118: 825-31; Young et al., 1995, FEBS Let. 377: 135-9; Glockshuber et al., 1990, Biochem. 29: 1362-7).

In certain aspects, one mutation is introduced into each of the VH and VL domains of the scFv to promote interchain disulfide bond formation between the VH and VL domains upon expression of a scFv. In another aspect, the two mutations are introduced in the same domain of the chain. In certain aspect, the two mutations are introduced in different chains. In certain aspects, multiple pairs of two mutations are introduced to promote formation of multiple disulphide bonds. In certain aspects, a cysteine is introduced to promote the disulphide bond formation. Exemplary amino acids that may be mutated to cysteine include amino acids 43, 44, 45, 46, 47, 103, 104, 105, and 106 of VH2 and amino acids 42, 43, 44, 45, 46, 98, 99, 100, and 101 of VL2. The foregoing numbering is based on Kabat numbering identifying the position relative only to the VH2 and VL2 of the scFv (and not relative to the position of the amino acid in a full length sequence of an antibody). Exemplary combinations of amino acid positions which may be mutated to cysteine residues include: VH44-VL100, VH105-VL43, VH105-VL42, VH44-VL101, VH106-VL43, VH104-VL43, VH44-VL99, VH45-VL98, VH46-VL98, VH103-VL43, VH103-VL44, and VH103-VL45. In some aspects, amino acid 44 of VH and amino acid 100 of VL are mutated to cysteines.

A further potential methodology that can be used, alone or in combination with one or more of the other methodologies described herein, is selecting the order of the domains of the scFv. In certain aspects, the orientation of the VH domain relative to the VL domain is optimized for stability. In certain aspects, the scFv is in the VH-linker-VL orientation. In certain aspects, the scFv is in the VL-linker-VH orientation.

An additional methodology that can be used, alone or in combination with one or more of the methodologies described herein, is by introducing one or more stabilizing mutations by mutating one or more surface residues of the scFv. In some aspects, one, two, three, four, five, six, or more than six residues are mutated in one or both of the VH and/or VL domain of the scFv. In certain aspects, changes are made in only the VH domain of the scFv. In certain aspects, changes are made in only the VL domain of the scFv. In certain aspects, changes are made in both the VH and VL domains of the scFv. The same number of changes may be made in each domain or a different number of changes may be made in each domain. In certain aspects, one or more of the changes is a conservative amino acid substitution from the residue present in the unmodified, parent scFv. In other aspects, one or more of the changes is a non-conservative amino acid substitution from the residue present in the unmodified, parent scFv. When multiple substitutions are made, either in one or both of the VH or VL domains of the scFv, each substitution is independently a conservative or a non-conservative substitution. In certain aspects, all of the substitutions are conservative substitutions. In certain aspects, all of the substitutions are non-conservative. In certain aspects, at least one of the substitutions is conservative. In certain aspects, at least one or the substitutions is non-conservative.

Yet a further methodology that can be used, alone or in combination with one or more of the additional methodologies described herein, is by introducing one or more substitutions by mutating one or more residues present in the VH and/or VL domain of the scFv to match the most frequent residue at said particular position of a consensus sequence of VH and/or VL domain of known, screened, and/or identified antibodies. In certain aspects, substitutions are introduced at one, two, three, four, five, six, or more than six positions in one or both of the VH domain and/or the VL domain of the scFv. The same number of changes may be made in each domain or a different number of changes may be made in each domain. In certain aspects, one or more of the changes in sequence match that of a given consensus is a conservative amino acid substitution from the residue present in the unmodified VH and/or VL sequence. In other aspects, one or more of the changes represent a non-conservative amino acid substitution from the residue present in the unmodified VH and/or VL sequence. When multiple substitutions are made, either in one or both of the VH or VL domain of the scFv, each substitution is independently a conservative or a non-conservative substitution. In certain aspects, all of the substitutions are conservative substitutions. In certain aspects, all of the substitutions are non-conservative substitutions. In certain aspects, at least one of the substitutions is conservative. In certain aspects, at least one or the substitutions is non-conservative.

It should be noted that any of the modifications described as useful for modifying or stabilizing the scFv portion can be applied to modify a Fab portion. For example, the variable domains of a Fab can be modified to improve stability, antigen binding and the like. Moreover, either the Fab or scFv portion can be modified to reduce immunogenicity.

In certain aspects, the antibody may be a scFv that comprises a variable light chain portion (VL) comprising the amino acid sequence set forth in any of SEQ ID NO:7, SEQ ID NO:17, SEQ ID NO:27, SEQ ID NO:37, SEQ ID NO:47, SEQ ID NO:57, SEQ ID NO:67, and SEQ ID NO:77. In further embodiments the scFv comprises a light chain portion comprising the amino acid sequence set forth in any of SEQ ID NO:57, SEQ ID NO:67, and SEQ ID NO:77. In certain aspects, the scFv comprises a heavy chain portion (VH) comprising the amino acid as set forth in any of SEQ ID NO:2. SEQ ID NO:12, SEQ ID NO:22, SEQ ID NO:32, SEQ ID NO:42, SEQ ID NO:52, SEQ ID NO:62, and SEQ ID NO:72. In further embodiments, the scFv comprises a heavy chain portion comprising the amino acid sequence set forth in any SEQ ID NO:52, SEQ ID NO:62, and SEQ ID NO:72.

The antibodies disclosed herein may further comprise one or more linker polypeptides. The linker may interconnect a heavy chain domain and a light chain domain (scFv) or connect an antibody or antigen binding fragment thereof to another agent, such as a label, Fc domain, or the like. Linkers can vary in length and sequence and are generally known in the art.

The serum half-life of an antibody comprising an Fc region may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The increase in half-life may allow for the reduction in amount of agent given to a patient as well as reducing the frequency of administration. To increase the serum half-life of an antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Alternatively, antibodies of the disclosure with increased half-lives may be generated by modifying amino acid residues identified as involved in the interaction between the Fc and the FcRn receptor (see, for examples, U.S. Pat. Nos. 6,821,505 and 7,083,784; and WO 09/058492). In addition, the half-life of antibodies of the disclosure may be increased by conjugation to PEG or albumin by techniques widely utilized in the art.

Antibodies falling within the scope of the disclosure may be identified by any of the structural and/or functional characteristics identified herein. For example, antibodies may be screened for particular binding features (e.g., $K_{off}$, KD, $IC_{50}$, specificity to/selectivity for ticagrelor and ticagrelor metabolites) using any of the techniques illustrated herein or that are otherwise known in the art.

Labels, Conjugates and Moieties

Antibodies of the disclosure may be conjugated to labels for the purposes of diagnostics and other assays wherein the antibodies and/or its target(s) may be detected. Labels include, without limitation, a chromophore, a fluorophore, a fluorescent protein, a phosphorescent dye, a tandem dye, a particle, a hapten, an enzyme and a radioisotope.

In certain aspects, the antibodies are conjugated to a fluorophore. The choice of the fluorophore attached to the antibody will determine the absorption and fluorescence emission properties of the conjugated antibody. Physical properties of a fluorophore label that can be used for an antibody and antibody-bound ligands include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. Other desirable properties of the fluorescent label may include cell permeability and low toxicity, for example if labeling of the antibody is to be performed in a cell or a model organism (e.g., a living animal).

In certain aspects, an enzyme is a label and is conjugated to an antibody. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the preferred measurable product, e.g. colorimetric, fluorescent or chemiluminescence. Such substrates are extensively used in the art and are well known by one skilled in the art and include for example, oxidoreductases such as horseradish peroxidase and a substrate such as 3,3'-diaminobenzidine (DAB); phosphatase enzymes such as an acid phosphatase, alkaline and a substrate such as 5-bromo-6-chloro-3-indolyl phosphate (BCIP); glycosidases, such as beta-galactosidase, beta-glucuronidase or beta-glucosidase and a substrate such as 5-bromo-4-chloro-3-indolyl beta-D-galactopyranoside (X-gal); additional enzymes include hydrolases such as cholinesterases and peptidases, oxidases such as glucose oxidase and cytochrome oxidases, and reductases for which suitable substrates are known.

Enzymes and their appropriate substrates that produce chemiluminescence are suitable for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In another aspect, haptens such as biotin, are also utilized as labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

In certain aspects, fluorescent proteins may be conjugated to the antibody as a label. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra.

In certain aspects, the label is a radioactive isotope. Examples of suitable radioactive materials include, but are not limited to, iodine ($^{121}I$, $^{123}I$, $^{125}I$, $^{131}I$), carbon ($_{14}C$), sulfur ($^{35}S$), tritium ($^{3}H$), indium ($^{111}In$, $^{112}In$, $^{113m}In$, $^{115m}In$,), technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{135}Xe$), fluorine ($^{18}F$), $^{153}SM$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$ and $^{97}Ru$.

In some aspects, drugs may be conjugated to the antibody. For example, an antibody comprising an scFv may be conjugated to a drug for the treatment of a cardiovascular disease and/or acute coronary syndromes.

In certain features, drugs and other molecules may be targeted to an antibody via site-specific conjugation. For example, the antibody may comprise cysteine engineered domains (including cysteine(s) engineered into a binding unit and/or Fc domain), which result in free thiol groups for conjugation reactions. In certain aspects, an antibody is engineered to incorporate specific conjugation sites.

Nucleic Acid Molecules Encoding Antibodies

The present disclosure provides nucleic acid molecules that encode antibodies or antigen-binding fragments thereof.

One aspect of the disclosure provides nucleic acid molecules encoding any of the antibodies specifically described herein. A nucleic acid molecule may encode a variable region of a heavy chain and/or light chain of the antibody.

In some aspects, the antibody is a Fab or scFv, wherein the nucleic acid portion encoding the Fab or scFv comprises a nucleotide sequence encoding a VL domain and a nucleotide sequence encoding a VH, and wherein the nucleotide sequence encoding the VL domain is optionally linked to the nucleotide sequence encoding the VH domain via a nucleotide sequence encoding a flexible polypeptide linker.

A further aspect provides a host cell transformed with any of the nucleic acid molecules as described herein. In another aspect of the disclosure there is provided a host cell comprising a vector comprising nucleic acid molecules as described herein. In one aspect the host cell may comprise more than one vector.

The disclosure contemplates nucleic acid molecules encoding any antibody of the disclosure, as well as either the light or heavy chain of an antibody. For example, the disclosure contemplates a nucleic acid molecule comprising a nucleotide sequence encoding one or more of SEQ ID NO:2, SEQ ID NO:12, SEQ ID NO:22, SEQ ID NO:32. SEQ ID NO:42, SEQ ID NO:52, SEQ ID NO:62, SEQ ID NO:72, SEQ ID NO:7, SEQ ID NO:17, SEQ ID NO:27, SEQ ID NO:37. SEQ ID NO:47, SEQ ID NO:57, SEQ ID NO:67, and SEQ ID NO:77. The disclosure further contemplates nucleic acid molecules encoding any antibody of the disclosure further comprising additional regions (e.g., Fc or modified Fc). In some embodiments the nucleic acid molecules may be selected from one or more of SEQ ID NO:1. SEQ ID NO:6, SEQ ID NO:11. SEQ ID NO:16, SEQ ID NO:21, SEQ ID NO:26, SEQ ID NO:31, SEQ ID NO:36, SEQ ID NO:41, , SEQ ID NO:46, SEQ ID NO:51. . SEQ ID NO:56, SEQ ID NO:61, SEQ ID NO:66, SEQ ID NO:71, or SEQ ID NO:76. In further embodiments, the disclosure provides a vector comprising a nucleic acid molecule selected from one or more of SEQ ID NO:1. SEQ ID NO:6, SEQ ID NO:11, SEQ ID NO:16, SEQ ID NO:21, SEQ ID NO:26, SEQ ID NO:31, SEQ ID NO:36. SEQ ID NO:41, , SEQ ID NO:46, SEQ ID NO:51, , SEQ ID NO:56, SEQ ID NO:61, SEQ ID NO:66, SEQ ID NO:71, or SEQ ID NO:76.

Methods for Producing Antibodies, Fabs, and scFvs

The disclosure provides methods for producing the antibodies and fragments thereof that are described herein. In some aspects, antigen-binding fragments of antibodies which recognize ticagrelor and the specific epitopes of ticagrelor and/or TAM disclosed herein may be generated by any technique known to those of skill in the art. For example, Fab and F(ab')$_2$ fragments may be produced from antibodies by proteolytic cleavage of immunoglobulin molecules, using enzymes such as papain (to produce Fab fragments) or pepsin (to produce F(ab')$_2$ fragments). Further, the antibodies including scFvs and Fabs, as described herein, can be generated using various phage display methods known in the art.

Generally, in phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector. The vector is electroporated in E. coli and the E. coli is infected with helper phage. Phage used in these methods are may be filamentous phage including fd and M13 and the VH and VL domains may be recombinantly fused to either the phage gene III or gene VIII. Phage expressing an antigen binding domain that binds to ticagrelor and/or TAM can be selected or identified with antigen, e.g., using labeled antigen or antigen bound or captured to a solid surface or bead. Similarly, binding domains that bind to antigens/haptens in addition to or other than to ticagrelor and/or TAM can be identified for deselection. Examples of phage display methods that can be used to make the antibodies of the present invention include those disclosed in Brinkman et al., 1995, J. Immunol. Methods 182: 41-50; Ames et al., 1995, J. Immunol. Methods 184: 177-186; Kettleborough et al., 1994, Eur. J. Immunol. 24: 952-958; Persic et al., 1997, Gene 187: 9-18; Burton et al., 1994, Advances in Immunology 57: 191-280; PCT application No. PCT/GB91/01 134; PCT publication Nos. WO 90/02809. WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment (scFvs and Fabs), and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6): 864-869; Sawai et al., 1995, AJRI 34: 26-34; and Better et al., 1988, Science 240: 1041-1043 (said references incorporated by reference in their entireties).

In certain aspects, the nucleic acids disclosed herein may be operably linked to one or more regulatory nucleotide sequences in an expression construct. The nucleic acid sequences encoding the antibody light and heavy chains can be cloned in the same expression vector in any orientation (e.g., light chain in front of the heavy chain or vice versa) or can be cloned in two different vectors. If expression is carried out using one vector, the two coding genes can have their own genetic elements (e.g., promoter, RBS, leader, stop, polyA, ect) or they can be cloned with one single set of genetic elements, but connected with a cistron element. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome.

In certain aspects, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a polypeptide and operably linked to at least one regulatory sequence, Regulatory sequences are art-recognized and are selected to direct expression of the encoded polypeptide. Accordingly, the term regulatory sequence includes promoters, enhancers, and other expression control elements. Exemplary, non-limiting regulatory sequences are described in Goeddel; *Gene Expression Technology: Methods in Enzymology*, Academic Press, San Diego, CA (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

The methods for producing an antibody of the disclosure may include, for example, a host cell transfected with one or more than one expression vectors encoding an antibody (e.g., a single vector encoding the heavy and the light chain or variable regions thereof, or two vectors, one encoding the heavy chain and one encoding the light chain or variable regions thereof) can be cultured under appropriate conditions to allow expression of the antibody to occur. The antibody may be secreted and isolated from a mixture of cells and medium containing the antibody. Alternatively, the antibody may be retained in the cytoplasm or in a membrane fraction and the cells harvested, lysed and the protein isolated. A cell culture includes host cells, media and other byproducts. Suitable media for cell culture are well known in the art. The antibody can be isolated from cell culture medium, host cells, or both using techniques known in the art for purifying proteins, antibodies, and antigen binding antibody fragments thereof, including ion-exchange chromatography, gel filtration chromatography, ultrafiltration, electrophoresis, and immunoaffinity purification. In certain aspects, the antibody is made as an antigen binding fragment of an antibody that comprises the heavy and light chain variable regions, which may increase solubility and facilitate purification.

A recombinant nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. In certain aspects, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV. pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various nucleic acid fragments coding for different polypeptide/antibody sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another aspect, the fusion gene can be synthesized by conventional techniques including automated DNA synthesizers. Alternatively, PCR amplification of gene fragments can be carried out using anchor primers which give rise to complementary overhangs between two consecutive nucleic acid fragments which can subsequently be annealed to generate a chimeric gene sequence (see, for example, *Current Protocols in Molecular Biology*, eds. Ausubel et al., John Wiley & Sons: 1992).

In some aspects, an expression vector expressing any of the nucleic acids described herein may be used to express the antibody in a host cell. For example, an antibody may be expressed in bacterial cells such as *E. coli*, insect cells (e.g., using a baculovirus expression system), yeast, or mammalian cells. Other suitable host cells are known to those skilled in the art.

Once the expression vector is transferred to a host cell by conventional techniques, the transfected cells are then cultured by conventional techniques to produce an antibody. Thus, the disclosure includes host cells containing a polynucleotide encoding an antibody or fragments thereof, operably linked to a heterologous promoter. In certain aspects, both the heavy chain and the light chain and/or heavy and light chain variable regions may be co-expressed (from the same or different vectors) in the host cell for expression of the entire antibody. In certain aspects, both the heavy and light chains of the antibody are expressed from a single promoter. In certain aspects, the heavy and light chains of the antibody are expressed from multiple promoters. In certain aspects, the heavy and light chains of the antibody are encoded on a single vector. In certain aspects, the heavy and light chains of the antibody are encoded on multiple vectors.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT20 and T47D, NSO (a murine myeloma cell line that does not endogenously produce any functional immunoglobulin chains), SP20, CRL7030 and HsS78Bst cells. In one aspect, human cell lines developed by immortalizing human lymphocytes can be used to recombinantly produce monoclonal antibodies. In one aspect, the human cell line PER.C6. (Crucell, Netherlands) can be used to recombinantly produce monoclonal antibodies.

Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681; etc), plants cells (US20080066200); and chicken cells (WO2008142124).

In certain aspects, an antibody of the disclosure is stably expressed in a cell line. Stable expression can be used for long-term, high-yield production of recombinant proteins. antibodies and antigen-binding fragments thereof. For example, cell lines which stably express the antibody molecule may be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Methods for producing stable cell lines with a high yield are well known in the art and reagents are generally available commercially.

In certain aspects, an antibody of the disclosure is transiently expressed in a cell line. Transient transfection is a process in which the nucleic acid introduced into a cell does not integrate into the genome or chromosomal DNA of that cell. It is in fact maintained as an extrachromosomal element. e.g. as an episome, in the cell. Transcription processes of the nucleic acid of the episome are not affected and a protein encoded by the nucleic acid of the episome is produced.

The cell line, either stable or transiently transfected, is maintained in cell culture medium and conditions well known in the art resulting in the expression and production of monoclonal antibodies. In certain aspects, the mammalian cell culture media is based on commercially available media formulations, including, for example, DMEM or Ham's F12. In other aspects, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

Once a molecule has been produced, it may be purified by any method known in the art for purification of an immunoglobulin molecule or fragments thereof, for example, by chromatography (e.g., ion exchange, affinity, particularly by affinity for the specific antigens Protein A or Protein G, and sizing column chromatography), centrifugation, differential solubility, or by any other standard technique for the purification of proteins, antibodies, and/or antibody fragments. Further, the molecules of the present disclosure or fragments thereof may be fused to heterologous polypeptide sequences (referred to herein as "tags" such as a histidine tag) described herein or otherwise known in the art to facilitate purification.

When using recombinant techniques, the molecule can be produced intracellularly, in the periplasmic space, or directly secreted into the medium. If the molecule is produced intracellularly, as a first step, the particulate debris, either host cells or lysed fragments. is removed, for example, by centrifugation or ultrafiltration. Carter et al., *Bio/Technology*, 10: 163-167 (1992) describe a procedure for isolating antibodies which are secreted into the periplasmic space of E. coli. Where the molecule is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The composition prepared from the cells can be purified using, for example. hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc domain, if present, in the molecule and will be understood by one of skill in the art. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing. SDS-PAGE, and ammonium sulfate precipitation are also available depending on the molecule to be recovered.

Following any preliminary purification step(s), the mixture comprising the molecule of interest and contaminants may be subjected to low pH hydrophobic interaction chromatography using an elution buffer at a pH between about 2.5-4.5, and performed at low salt concentrations (e.g., from about 0-0.25 M salt).

An antibody may be made and purified using, for example, any one or combination of techniques set forth above and/or in the Examples. Regardless of how an antibody is purified, to confirm functional binding of the antibody of the disclosure, binding assays may be performed (before and/or after purification). For example, dual ELISA assays may be used. In some aspects, a first antigen (e.g., ticagrelor or a competitor thereof) is coated on a well, and binding to this antigen immobilizes the antibody preparing it for detection.

Pharmaceutical Formulations

In certain aspects, the disclosure provides pharmaceutical compositions. Such pharmaceutical compositions may be compositions comprising a nucleic acid molecule that encodes an antibody. Such pharmaceutical compositions may also be compositions comprising an antibody, or a combination of antibodies, and a pharmaceutically acceptable excipient. In certain aspects, the pharmaceutical compositions of the disclosure are used as a medicament.

In certain aspects, an antibody or a combination of antibodies (or nucleic acid molecules encoding an antibody or a combination of antibodies) may be formulated with a pharmaceutically acceptable carrier, excipient or stabilizer, as pharmaceutical compositions. In certain aspects, such pharmaceutical compositions are suitable for administration to a human or non-human animal via any one or more route of administration using methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also contain compatible solid or liquid fillers, diluents or encapsulating substances which are suitable for administration into a human. Other contemplated carriers, excipients, and/or additives, which may be utilized in the formulations described herein include, for example, flavoring agents, antimicrobial agents, sweeteners, antioxidants, antistatic agents, lipids, protein excipients such as serum albumin, gelatin, casein, salt-forming counterions such as sodium and the like. These and additional known pharmaceutical carriers, excipients and/or additives suitable for use in the formulations described herein are known in the art, e.g., as listed in "Remington: The Science & Practice of Pharmacy", 21$^{st}$ ed., Lippincott Williams & Wilkins, (2005), and in the "Physician's Desk Reference", 60$^{th}$ ed., Medical Economics, Montvale, N.J. (2005). Pharmaceutically acceptable carriers can be selected that are suitable for the mode of administration, solubility and/or stability desired or required.

The formulations described herein comprise active agents (e.g., antibodies or antibody fragments such as Fab or scFv) in a concentration resulting in a w/v appropriate for a desired dose. In certain aspects, the active agent is present in a formulation at a concentration of about 1 mg/ml to about 200 mg/ml, about 1 mg/ml to about 100 mg/ml, about 1 mg/ml to about 50 mg/ml, or about 1 mg/ml to about 25 mg/ml. In certain aspects, the active agent is present at a concentration of about 25 mg/ml. In certain aspects, the concentration of the active agent in a formulation may vary from about 0.1 to about 100 weight %. In certain aspects, the concentration of the active agent is in the range of 0.003 to 1.0 molar.

In one aspect, the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)). In certain specific aspects, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

When used for in vivo administration, the formulations of the disclosure should be sterile. The formulations of the disclosure may be sterilized by various sterilization methods, including sterile filtration, radiation, etc. In one aspect, the formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins. (2005).

Therapeutic compositions of the present disclosure can be formulated for particular routes of administration, such as oral, nasal, pulmonary, topical (including buccal and sublingual), rectal, vaginal and/or parenteral administration. The phrases "parenteral administration" and "administered parenterally" as used herein refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Formulations of the present disclosure which are suitable for topical or transdermal administration include powders, sprays, ointments, pastes, creams, lotions, gels, solutions, patches and inhalants. The antibodies may be mixed under sterile conditions with a pharmaceutically acceptable carrier, and with any preservatives, buffers, or propellants which may be required (U.S. Pat. Nos. 7,378, 110; 7,258,873; 7,135, 180; US Publication No. 2004-0042972: and 2004-0042971).

The formulations may conveniently be presented in unit dosage form and may be prepared by any method known in the art of pharmacy. Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient (e.g., "a therapeutically effective amount"). The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. Suitable dosages may range from about 0.0001 to about 100 mg/kg of body weight or greater, for example about 0.1, 1, 10, or 50 mg/kg of body weight, with about 1 to about 10 mg/kg of body weight being suitable.

Note that the disclosure similarly contemplates that formulations suitable for diagnostic and research use may also be made. The concentration of active agent in such formulations, as well as the presence or absence of excipients and/or pyrogens can be selected based on the particular application and intended use.

Uses

The antibodies disclosed herein are useful in therapeutic methods, including combination therapy, for neutralizing the activity of inhibitors of platelet activation, aggregation and degranulation, promoters of platelet disaggregation, and anti-thrombotic agents. Thus, the antibodies described herein, find use in a number of applications that relate to the administration of ticagrelor (including companion methods) and are suitably useful for neutralizing the effect of ticagrelor and/or one or more metabolites of ticagrelor. In such methods, the antibody can reduce, neutralize, eliminate, or otherwise inhibit the activity of ticagrelor, optionally reversibly, and treat or prevent any number of effects, disorders and/or symptoms associated with ticagrelor administration and/or arising from therapy comprising ticagrelor.

The antibodies may be administered to patients who are being treated, or who are in need of treatment or prophylaxis for indications that are treatable and/or indicated for ticagrelor (BRILINTA), including for example, unstable angina, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, including coronary angioplasty (PTCA), endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine.

In some embodiments the antibodies disclosed herein may be administered to a patient who is receiving or who has received treatment comprising ticagrelor, and who is in need of treatment, or will be in need of treatment, for bleeding or potential bleeding associated with coronary artery bypass grafting (CABG), cardiothoracic surgery, mediastinal re-exploration. post-operative stroke, mechanical ventilation, prolonged stay in an intensive care unit, urgent non-cardiac surgery (for example, neurological or ophthalmological surgery, spinal surgery, intracranial surgery, orbital surgery, orthopedic surgery, nephrectomy, hemicolectomy, and the like. As such, the methods provided herein may encompass administration of the antibody as a co-therapeutic with ticagrelor (simultaneously), or within a period of time following ticagrelor administration (e.g., minutes, hours, or days). For example, in some embodiments, the method may include administration of the antibody to a patient who has been administered ticagrelor within 10 - 120 minutes of ticagrelor administration. In some embodiments, the method may include administration of the antibody to a patient who has been administered ticagrelor within 1-48 hours of ticagrelor administration. In some embodiments, the antibody is administered to a subject who has been administered ticagrelor within an amount of time that would not allow for the metabolism and elimination of ticagrelor and/or its metabolites from the subject.

In some embodiments, the disclosure provides a method of inhibiting the effect of ticagrelor, or an active metabolite thereof, on the ($P2Y_2$) receptor in a patient.

In some embodiments, the disclosure provides a method of inhibiting the binding of ticagrelor, or an active metabolite thereof, to a $P2Y_{12}$ receptor in a patient.

In some embodiments, the disclosure provides a method of activating ADP-induced platelet aggregation in a patient who has been administered ticagrelor.

The antibodies of the disclosure, such as those exemplified in the Examples, may also be used for diagnostic purposes. For example, one or more target agents (ticagrelor or metabolites thereof) may be detected in tissues or cells of a subject in order to determine or screen for circulating amounts of ticagrelor in a subject. A diagnostic kit may comprise one or more antibody, and a detection system for indicating the reaction of the antibody with ticagrelor or metabolites thereof, if any are present.

Thus, the disclosure contemplates numerous uses for the antibodies, including therapeutic, diagnostic, and research uses. Diagnostic and research uses may be in vivo or ex vivo.

Kits

Another aspect of the present disclosure is a kit. In one aspect, a kit comprises any of the compositions or pharmaceutical compositions of a nucleic acid, antibody, expression vector, or host cell described above, and instructions or a label directing appropriate use or administration. Optionally, a kit may also include one or more containers and/or a syringe or other device to facilitate delivery or use. The disclosure contemplates that all or any subset of the components for conducting research assays, diagnostic assays and/or for administering therapeutically effective amounts may be enclosed in the kit. Similarly, the kit may include instructions for making an antibody by. for example culturing a host cell that expresses a nucleic acid that encodes an antibody of the disclosure under suitable conditions. By way of additional example, a kit for therapeutic administration of an antibody of the disclosure may comprise a solution containing a pharmaceutical formulation of the antibody, or a lyophilized preparation of the antibody, and instructions for administering the composition to a patient in need thereof and/or for reconstituting the lyophilized product. In certain embodiments the kit will further comprise ticagrelor in a formulation appropriate for administration to a subject (e.g., BRILINTA™, BRILIQUE™). In such embodiments, the kit may further comprise instructions for the administration of both the antibody and ticagrelor formulation to a patient in need of treatment with the antibody, with ticagrelor, or with both the antibody and ticagrelor.

The present disclosure also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient. e.g., an above-described antibody, and/or a ticagrelor formulation, is sterile and suitable for administration as a particulate free solution. In certain aspects, the formulation is suitable for an injectable route of administration. In some embodiments the administration is subcutaneous. In some embodiments the administration is intravenous administration. Thus, routes of administration including injection or infusion to a human or animal are contemplated.

In a specific aspect, the formulations of the disclosure are formulated in single dose vials as a sterile liquid. Exemplary containers include, but are not limited to, vials, bottles. pre-filled syringes, IV bags, blister packs (comprising one or more pills). Optionally associated with such container(s) can be a notice in the form prescribed by a governmental agency regulating the manufacture, use or sale of pharmaceuticals or biological products, which notice reflects approval by the agency of manufacture, use or sale for human diagnosis and/or administration.

As with any pharmaceutical product, the packaging material and container are designed to protect the stability of the product during storage and shipment. Further, the products of the disclosure include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, etc., and other monitoring information.

A kit for diagnostic assays may comprise a solution containing an antibody or a lyophilized preparation of an antibody of the disclosure, wherein the antibody binds specifically to ticagrelor and/or a metabolite thereof, as well as reagents for detecting such an antibody. The antibody may be labeled according to methods known in the art and described herein, including but not limited to labels such as small molecule fluorescent tags, proteins such as biotin, GFP or other fluorescent proteins, or epitope sequences such as his or myc. Similarly, primary antibodies used for detecting an antibody may be included in the kit. Primary antibodies may be directed to sequences on the antibody or to labels, tags, or epitopes with which the antibody is labeled. Primary antibodies may, in turn, be labeled for detection, or, if further amplification of the signal is desired, the primary antibodies may be detected by secondary antibodies, which may also be included in the kit.

Kits for research use are also contemplated. Such kits may, for example. resemble kits intended for diagnostic or therapeutic uses but further include a label specifying that the kit and its use is restricted to research purposes only.

EXAMPLES

List of Abbreviations

| Abbreviation | Explanation |
| --- | --- |
| ACN | acetonitrile |
| br | broad |
| BSA | Bovine serum albumin |
| CV | column volume |
| d | doublet |

-continued

| Abbreviation | Explanation |
| --- | --- |
| dd | double doublet |
| DCM | dichloromethane |
| DMF | N,N-dimethylformamide |
| DMSO | dimethylsulphoxide |
| DPBS | Dulbecco's phosphate buffered saline |
| EDC | 1-ethyl-3-(3-dimethylaminopropyl)carbodiimide) |
| EtOAc | ethylacetate |
| FA | formic acid |
| HOAc | acetic acid |
| HPLC | high-performance liquid chromatography |
| HRMS | high resolution mass spectrometry |
| HTS | high throughput screen |
| HTRF ® | homogeneous time resolved fluorescence |
| HYFLO ® | filter aid, flux calcined, treated with sodium carbonate |
| Hz | Hertz |
| J | coupling constant |
| LC | liquid chromatography |
| m | multiplet |
| MS | mass spectra |
| NMR | nuclear magnetic resonance |
| OAc | acetate |
| Pd/C | Palladium on charcoal |
| pM | picomolar |
| PK/PD | Pharmacokinetic/Pharmacodynamic |
| KF | Potassium fluoride |
| q | quartet |
| r.t. | room temperature |
| s | singlet |
| sat. | saturated |
| scFv | single chain fragment variable |
| t | triplet |
| TFA | trifluoroacetic acid |
| TEA | triethylamine |
| TBME | tert-butyl methyl ether |
| THF | tetrahydrofuran |
| TIM | ticagrelor inactive metabolite |
| TLC | thin layer chomatography |
| TR-FRET | Time resolved fluorescence resonance energy transfer |

Example 1: Preparation and Characterization of Haptens

This example describes methods of synthesis, optimization, isolation, and characterization of several haptens that were used to generate exemplary antibodies as described herein. The haptens include ticagrelor, ticagrelor metabolites (TAM and TIM), biotinylated ticagrelor, and biotinylated adenosine (see, e.g., FIG. 2A for chemical hapten structures in non-biotinylated forms). Ticagrelor was synthesized as described in international patent publication WO 2000/034283 (Guile, et al., 2000) and TAM was synthesized as described in international patent publication WO 1999/005143 (Guile, et al., 1999), each incorporated by reference in their entirety.

Straight phase chromatography was performed using Biotage silica gel 40S, 40M, 12i or Merck silica gel 60 (0.063-0.200 mm). Flash-chromatography was performed using either standard glass- or plastic-columns or on a Biotage Horizon system. Chemical shifts are given in ppm with the solvent as internal standard. Protones on heteroatoms such as NH and OH protons are only reported when detected in NMR and can therefore be missing.

Example 1.1: Biotinylated Ticagrelor

N-(2-((((1S,2S,3S,4R)-4-(7-(((1R,2S)-2-(3,4-difluorophenyl)cyclopropyl)amino)-5-(propylthio)-3H-[1,2,3]triazolo[4,5-d]pyrimidin-3-yl)-2,3-dihydroxycyclopentyl)oxy)ethyl)-6-(6-(5-((3aS,4S,6aR)-2-oxohexahydro-1H-thieno[3,4-d]imidazol-4-yl)pentanamido)hexanamido)hexanamide (1.1)

pound (1.a) (714 mg, 111%) as a yellow thick oil, which was used as crude without further purification.

$^1$H NMR (400 MHZ, CDCl$_3$) δ1.02 (dd, 3H), 1.3-1.47 (m, 5H), 1.55 (s, 3H), 1.72 (d, 2H), 2.20 (d, 1H), 2.6-2.71 (m, 2H), 2.97 (s, 3H), 3-3.19 (m, 3H), 3.57-3.68 (m, 1H), 3.69-3.79 (m, 1H), 4.02 (td, 1H), 4.13-4.24 (m, 2H), 4.78 (dd, 1H), 5.13 (td, 1H), 5.57 (s, 1H), 6.50 (s, 1H), 7.03 (s, 1H), 7.07-7.16 (m, 2H).

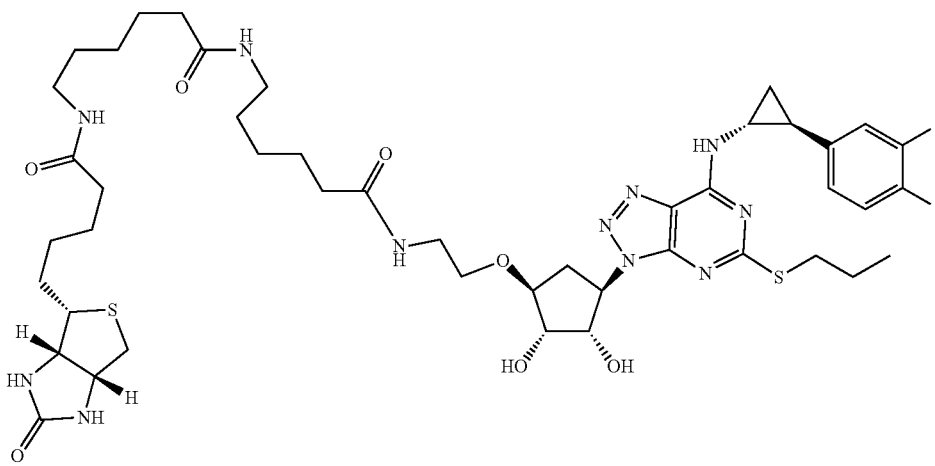

(1.1)

(i) Preparation of 2-(((3aR,4S,6R,6aS)-6-(7-(((1R,2S)-2-(3,4-difluorophenyl)cyclopropyl)amino)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethyl methanesulfonate (1.a)

$^{19}$F NMR (376 MHz, CDCl$_3$) δ-141.37 (J=21.3). −138.10 (J=21.3).

(ii) Preparation of 3-((3aS,4R,6S,6aR)-6-(2-azidoethoxy)-2,2-dimethyltetrahydro-3aH-cyclopenta[d][1,3]dioxol-4-yl)-N-((1R,2S)-2-(3,4-difluorophenyl)cyclopropyl)-5-(propylthio)-3H-[1,2,3]triazolo[4,5-d]pyrimidin-7-amine (1.b)

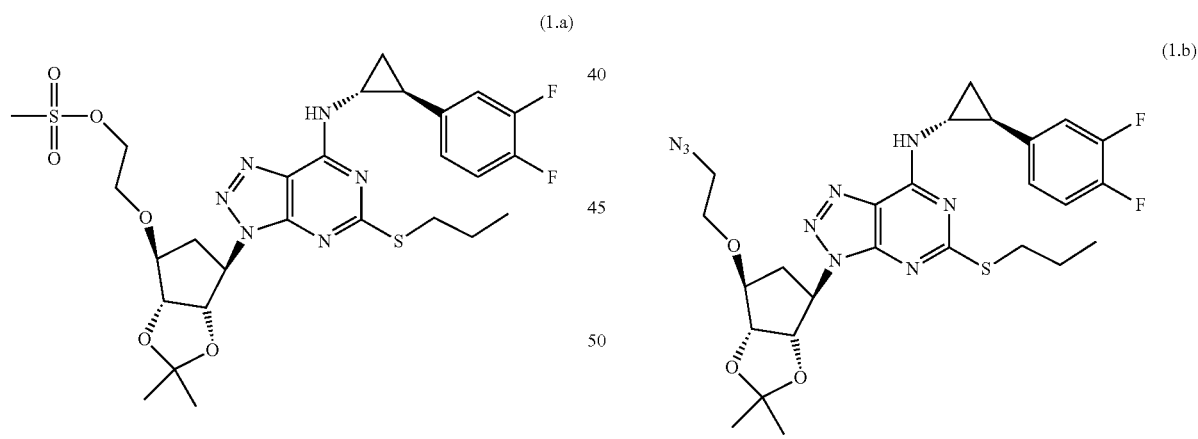

Methanesulfonyl chloride (0.086 mL, 1.10 mmol) was added dropwise to a solution of 2-(((3aR,4S,6R,6aS)-6-(7-(((1R,2S)-2-(3,4-difluorophenyl)cyclopropyl)amino)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol (See Springthorpe, B. et. al. Bioorg. Med. Chem. Lett., 2007, 17, 6013-6018) (0.563 g, 1.0 mmol) and TEA (0.209 mL, 1.50 mmol) in DCM (5 mL) at 0° C. The mixture was stirred from 0° C. to about 5° C. over 3 h. The reaction mixture was diluted with DCM (30 mL) and washed with water (5 mL). The mixture was dried by passing through a phase separator. Evaporation of the solvent and co-evaporation from toluene gave the title com- A mixture of 2-(((3aR,4S,6R,6aS)-6-(7-(((1R,2S)-2-(3,4-difluorophenyl)cyclopropyl)amino)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethyl methanesulfonate (1.a) (0.641 g, 1 mmol) and sodium azide (0.070 mL, 2.00 mmol) in DMF (7 mL) was heated to 60° C. for 15.5 h under nitrogen atmosphere. A white precipitate formed. Water was added (20 mL) and the product was extracted twice with TBME (100+40 mL). The organic phase was dried over Na$_2$SO$_4$. The organic phase was filtrated and the solvent was removed under reduced pressure. The residue was purified by flash chromatography on a 2×8 cm silica column using heptane/EtOAc 1/1 as eluent, (TLC using heptane/EtOAc 1/1 (Rf product=0.5). Collection of the relevant fractions and evaporation of the solvents gave the title compound (1.b) (514 mg, 87%) as a clear, thick oil.

¹H NMR (400 MHZ, CDCl₃) δ1.00 (s, 3H), 1.33-1.42 (m, 5H), 1.59 (s, 3H), 1.73 (d, 2H), 2.17 (s, 1H), 2.68 (t, 2H), 2.96-3.17 (m, 3H), 3.19-3.33 (m, 2H), 3.52-3.63 (m, 1H), 3.72 (ddd, 1H), 4.03 (td, 1H), 4.79 (dd, 1H), 5.13 (td, 1H), 5.54 (dd, 1H), 6.43 (s, 1H), 6.96-7.23 (m, 3H).

(iii) Preparation of the intermediate 3-((3aS,4R,6S,6aR)-6-(2-aminoethoxy)-2,2-dimethyltetrahydro-3aH-cyclopenta[d][1,3]dioxol-4-yl)-N-((1R,2S)-2-(3,4-difluorophenyl)cyclopropyl)-5-(propylthio)-3H-[1,2,3]triazolo[4,5-d]pyrimidin-7-amine (1.c)

(1.c)

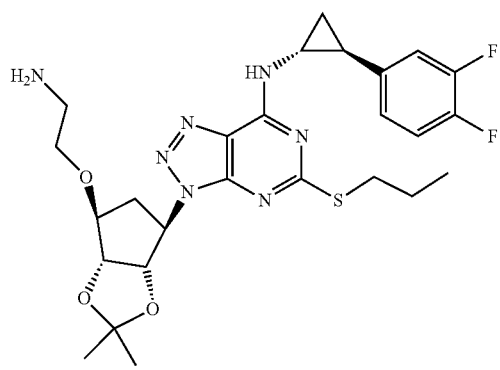

3-((3aS,4R,6S,6aR)-6-(2-azidoethoxy)-2,2-dimethyltetrahydro-3aH-cyclopenta[d][1,3]dioxol-4-yl)-N-((1R,2S)-2-(3,4-difluorophenyl)cyclopropyl)-5-(propylthio)-3H-[1,2,3]triazolo[4,5-d]pyrimidin-7-amine (1.b) (62.0 mg, 0.11 mmol) in EtOH (99.5%) (2 mL) was added to Pd/C (5% Pd, 50 wt% Pd/C, 22.46 mg, 5.28 μmol) and the mixture was hydrogenated at atmospheric pressure for 2h. The reaction mixture was filtered through HYFLO® and the plug was further rinsed with EtOH (99.5%). The solvent was removed under reduced pressure, the residue was re-dissolved in DCM (2×2 mL) and the solvent was removed under reduced pressure. The residue was purified by flash chromatography on a 2×8 cm silica column using DCM/ NH₃ (sat.) in MeOH 95/5 as eluent. Collection of the relevant fractions gave the title compound (1.c) (41 mg, 69%).

¹H NMR (400 MHZ, CDCl₃) δ0.98 (m, 3H), 1.28-1.46 (m, 7H), 1.54 (s, 3H), 1.62-1.81 (m, 2H), 2.15 (s, 1H), 2.48-2.81 (m, 4H), 3.07 (tt, 3H), 3.34-3.47 (m, 1H), 3.53 (ddd, 1H), 3.99 (td, 1H), 4.79 (dd, 1H), 5.12 (td, 1H), 5.52 (dd, 1H), 7.02 (s, 1H), 7.09 (dt, 2H), 7.23 (s. 1H).

¹⁹F NMR (376 MHz, CDCl₃) δ-141.43 (J=21.3), -138.13 (J=21.3).

(iv) Preparation of the intermediate (1S,2S,3S,5R)-3-(2-aminoethoxy)-5-(7-(((1R,2S)-2-(3,4-difluorophenyl)cyclopropyl)amino)-5-(propylthio)-3H-[1,2,3]triazolo[4,5-d]pyrimidin-3-yl)cyclopentane-1,2-diol (1.d)

(1.d)

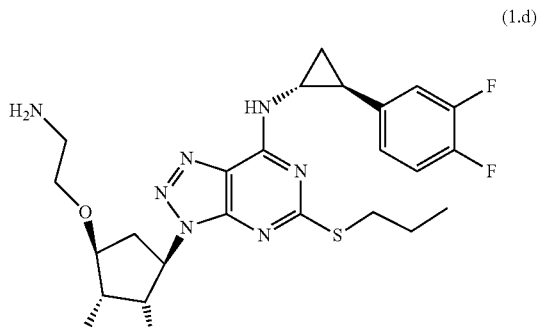

A pre-cooled, ice/water bath temperature, mixture of TFA (8 mL, 103.84 mmol) and water (0.88 mL, 48.85 mmol) was added to a pre-cooled flask with 3-((3aS,4R,6S,6aR)-6-(2-aminoethoxy)-2,2-dimethyltetrahydro-3aH-cyclopenta[d][1,3]dioxol-4-yl)-N-((1R,2S)-2-(3,4-difluorophenyl)cyclopropyl)-5-(propylthio)-3H-[1,2,3]triazolo[4,5-d]pyrimidin-7-amine (1.c) (340 mg, 0.61 mmol). The reaction mixture was stirred at 0-5° C. for 1 h. The solvent was removed under reduced pressure and the residue was dissolved in DCM (100 mL) and washed with NaHCO₃ (sat. 10 mL). Brine (5 mL) was added to the aqueous phase and this was extracted with EtOAc (30 mL). The combined organic phases were dried over Na₂SO₄. Filtration followed by evaporation of the solvents gave the crude product as an off-white solid. The compound was purified by preparative HPLC on a XBridge C18 column (10 μm 250×50 ID mm) using a gradient of 35-75% ACN in H₂O/ACN/NH, 95/5/0.2 buffer over 20 minutes with a flow of 100 mL/min. The compounds were detected by UV at 298 nm. The peak fractions were evaporated to dryness under reduced pressure. The residue was dissolved in DCM and filtered through a phase separator. Removal of the solvent under reduced pressure gave the title compound (1.d) (213 mg, 67.5%). LC-MS m/z 522.3 (M+H)+.

(v) Preparation of compound N-(2-(((1S,2S,3S,4R)-4-(7-(((1R,2S)-2-(3,4-difluorophenyl)cyclopropyl)amino)-5-(propylthio)-3H-[1,2,3]triazolo[4,5-d]pyrimidin-3-yl)-2,3-dihydroxycyclopentyl)oxy)ethyl)-6-(6-(5-((3aS,4S,6aR)-2-oxohexahydro-1H-thieno[3,4-d]imidazol-4-yl)pentanamido)hexanamido)hexanamide. (1.1)

2,5-dioxopyrrolidin-1-yl 6-(6-(5-((3aS,4S,6aR)-2-oxohexahydro-1H-thieno[3,4-d]imidazol-4-yl)pentanamido) hexanamido)hexanoate (21.77 mg, 0.04 mmol) was added to a solution of (1S,2S,3S.5R)-3-(2-aminoethoxy)-5-(7-(((1R,2S)-2-(3,4-difluorophenyl)cyclopropyl)amino)-5-(propylthio)-3H-[1,2,3]triazolo[4,5-d]pyrimidin-3-yl)cyclopentane-1,2-diol (20 mg. 0.04 mmol) in dry DMF (1.0 mL) and the mixture was placed under an nitrogen atmosphere and stirred at r.t. for 6 h. The solvent was removed under reduced pressure at 40° C. The compound was purified by preparative HPLC on a Kromasil C18 column (10 μm 250×20 ID mm) using a gradient of 20-60% ACN in H₂O/ACN/FA 95/5/0.2 buffer, over 20 minutes with a flow of 19 mL/min. The compounds were detected by UV at 298 nm. The peak fractions were collected, concentrated, and freeze dried to give the title compound (1.1) (21.4 mg, 57.3%).

¹H NMR (600 MHz, DMSO): Two rotamers present (ratio 5:1), signals from major rotamer at δ0.81 (t, 3H), 1.15-1.64 (m, 20H), 2.03 (ddd, 7H), 2.12 (ddd, 1H), 2.57 (d, 1H), 2.59-2.67 (m, 1H), 2.77-2.89 (m, 2H), 2.93 (dd, 1H), 2.96-3.01 (m, 4H), 3.05-3.12 (m, 1H), 3.15 (td, 1H), 3.18-3.25 (m. 2H), 3.39-3.46 (m, 1H), 3.48 (tt, 1H), 3.7-3.76 (m, 1H), 3.92 (8, 1H), 4.08-4.14 (m, 1H), 4.30 (dd, 1H), 4.54 (dd, 1H), 4.95 (q, 1H), 5.06 (s, 1H), 5.13 (d, 1H), 6.35 (s, 1H), 6.42 (s, 1H), 7.07 (d, 1H), 7.31 (ddt, 2H), 7.71 (dt, 2H), 7.82 (t, 1H), 9.36 (d. 1H). Selected signals from minor rotamer at δ0.98 (CH3), 8.95 (ArNH).

HRMS Calcd for [C45H65F2N11O7S2]⁺: 974.4556; found: 974.4585 (M+H)⁺

Example 1.2: Biotinylated Adenosine

N-(((2R,3S,4R,5R)-5-(6-amino-9H-purin-9-yl)-3,4-dihydroxytetrahydrofuran-2-yl)methyl)-6-(6-(5-((3aS,4S,6aR)-2-oxohexahydro-1H-thieno[3,4-d]imidazol-4-yl)pentanamido)hexanamido)hexanamide (1.2)

(1.2)

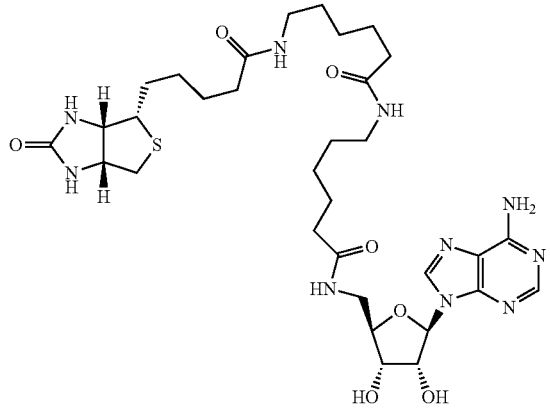

(i) Preparation of N-(((3aR,4R,6R,6aR)-6-(6-amino-9H-purin-9-yl)-2,2-dimethyltetrahydrofuro[3,4-d][1,3]dioxol-4-yl)methyl)-6-(6-(5-((3aS,4S,6aR)-2-oxohexahydro-1H-thieno[3,4-d]imidazol-4-yl)pentanamido)hexanamido)hexanamide (1.e)

(1.e)

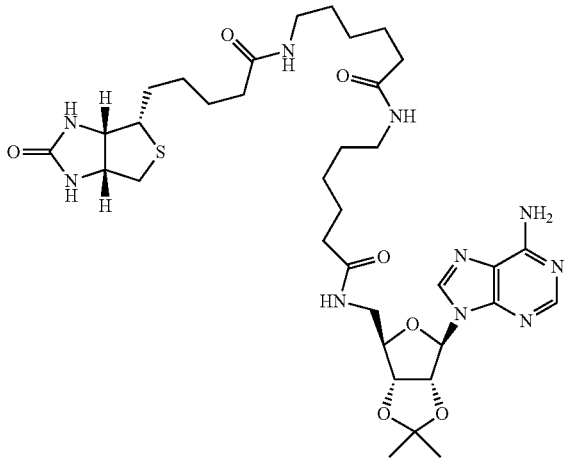

DMF (2 mL) was added to 2,5-dioxopyrrolidin-1-yl 6-(6-(5-((3aS,4S,6aR)-2-oxohexahydro-1H-thieno[3,4-d]imidazol-4-yl)pentanamido)hexanamido)hexanoate (55.6 mg. 0.10 mmol) and 9-((3aR,4R,6R,6aR)-6-(aminomethyl)-2,2-dimethyltetrahydrofuro[3,4-d][1,3]dioxol-4-yl)-9H-purin-6-amine (30 mg, 0.10 mmol) (See Austin, D. J. and Liu, F., Tetrahedr. Lett., 2001, 3153-3154) at r.t. and the reaction mixture was placed under nitrogen atmosphere and stirred for 1 h and 45 min to provide (1.e). The solvent was subsequently removed under reduced pressure. Used as crude product without further purification. LC-MS m/z 759 (M+H)⁺, 757 (M–H)⁻.

(ii) Preparation of the final compound N-(((2R,3S,4R,5R)-5-(6-amino-9H-purin-9-yl)-3,4-dihydroxytetrahydrofuran-2-yl)methyl)-6-(6-(5-((3aS,4S,6aR)-2-oxohexahydro-1H-thieno[3,4-d]imidazol-4-yl)pentanamido)hexanamido) hexanamide (1.2)

A mixture of TFA (1.8 ml, 23.36 mmol) and water (0.2 mL. 11.10 mmol) was added to the crude N-(((3aR,4R,6R, 6aR)-6-(6-amino-9H-purin-9-yl)-2,2-dimethyltetrahydrofuro[3,4-d][1,3]dioxol-4-yl)methyl)-6-(6-(5-((3aS,4S,6aR)-2-oxohexahydro-1H-thieno[3,4-d]imidazol-4-yl) pentanamido)hexanamido)hexanamide (1.e) (76 mg, 0.1 mmol) and the reaction mixture was stirred at 0° C. for 1 h 25 minutes. The solvents were removed under reduced pressure and the residue was dissolved in DMSO. The compound was purified by preparative HPLC on a XBridge C18 column (10 µm 250×19 ID mm) using a gradient of 5-45% ACN in H₂O/ACN/NH, 95/5/0.2 buffer over 20 minutes with a flow of 19 mL/min. The compounds were detected by UV at 259 nm. The peak fractions were concentrated and freeze dried to give the title compound (1.2) (50 mg, 69.6%) as a white fluffy solid.

¹H NMR (600 MHZ, DMSO, 40° C.) δ1.17-1.26 (m, 4H), 1.27-1.4 (m. 6H), 1.43-1.54 (m. 7H), 1.62 (ddt, 1H), 1.99-2.06 (m, 4H), 2.12 (t, 2H), 2.58 (d, 1H), 2.82 (dt, 1H), 2.96-3.05 (m, 4H), 3.05-3.14 (m, 1H), 3.36 (dt, 1H), 3.44 (dt, 1H), 3.96 (dd, 1H), 4.04 (dd, 1H), 4.11-4.15 (m, 1H), 4.29-4.33 (m, 1H), 4.67 (dd, 1H), 5.16 (d, 1H), 5.38 (d, 1H), 5.84 (d, 1H), 6.29 (s, 1H), 6.33 (d, 1H), 7.25 (s, 2H), 7.64 (dt, 2H), 8.11 (t, 1H). 8.16 (s, 1H), 8.31 (s, 1H). HRMS Calcd for [C32H50N10O7S]⁺: 719.3657; found: 719.3667 (M+H)⁺

Example 2: Isolation and Identification of Anti-Ticagrelor/TAM Antibodies

Figure 2A:
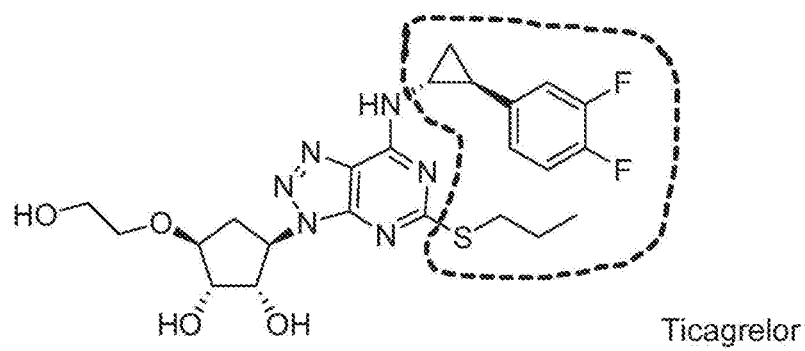
FIG. 2A-C—haptans and Fab specificity.
Figure 2A:
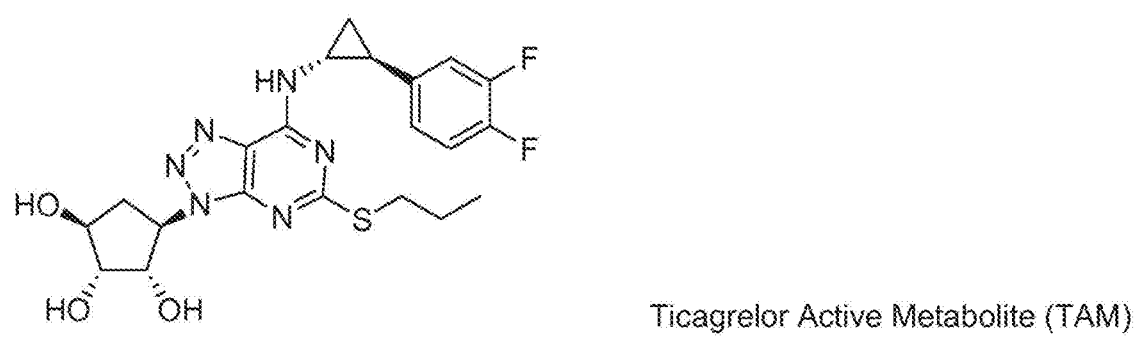
Figure 2A:
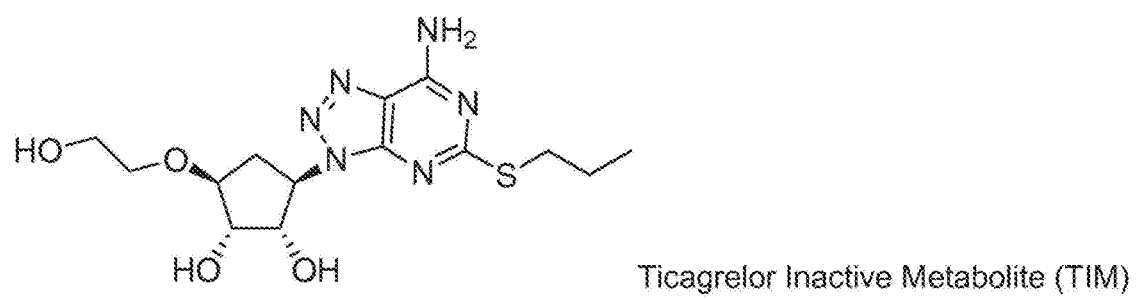
Figure 2A:
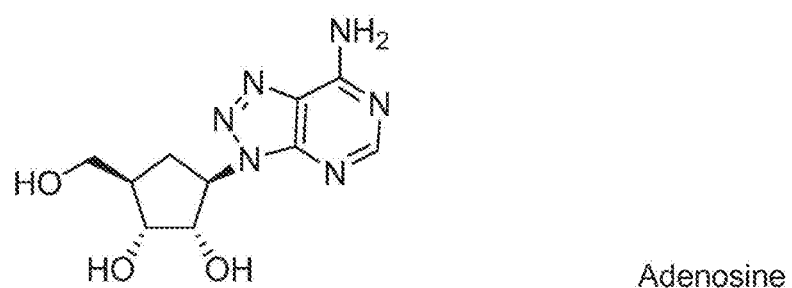
Figure 2B:
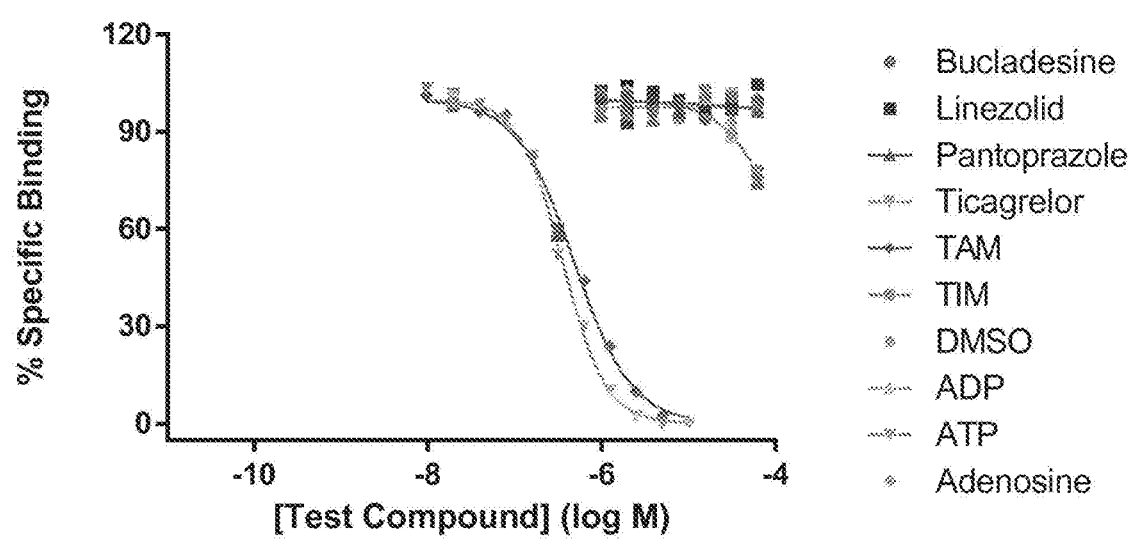
Figure 2C:
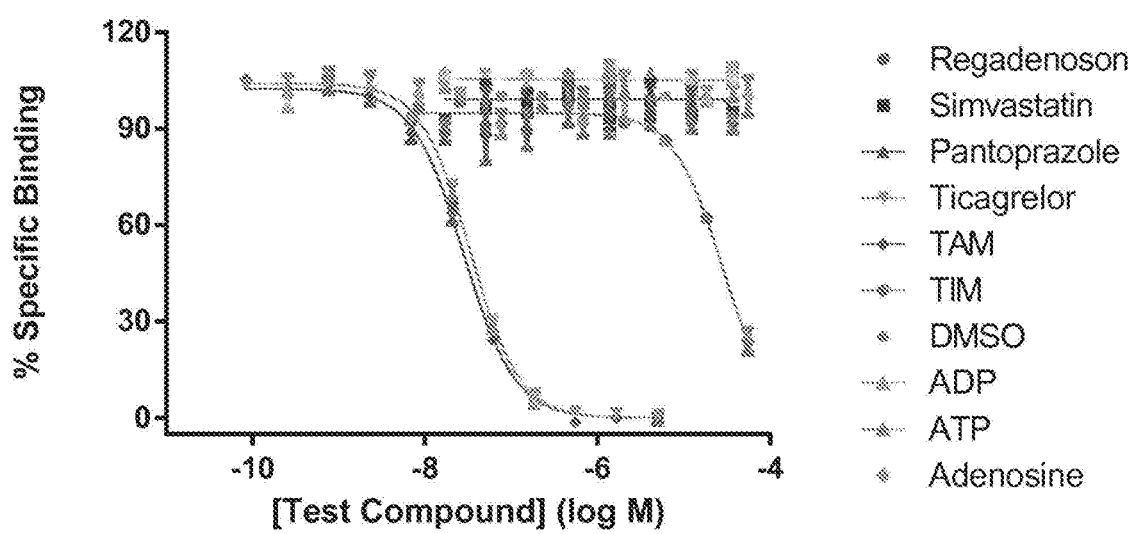

This example illustrates strategies and techniques that may be used in the production of antibodies to ticagrelor and its metabolites, compounds that have structural similarity to ATP and contains an adenosine-like core (Springthorpe et al 2007 Bioorg Med Chem Lett. 17: 6013-6018). The chemical structures of ticagrelor, ticagrelor active metabolite (TAM) and ticagrelor inactive metabolite (TIM) are shown in FIG. 2A. As discussed above, the antibodies disclosed and generated herein can bind and neutralise ticagrelor and TAM and may bind to TIM, but do not bind or significantly inhibit other structurally related compounds such as adenosine. While binding activity to TIM is an optional feature of the antibodies disclosed herein, antibodies that exhibit binding activity to TIM are not expected to affect the dose of the antibody/antidote required, because TIM typically represents a small or insignificant fraction of ticagrelor metabolites.

The common epitopes, i.e., unique R groups of ticagrelor and TAM (di-fluorophenyl-cyclopropyl and thiopropyl substituents) were targeted in order to confer antibody binding specificity and selectivity for those compounds. The epitope of interest is encircled by the dashed line in FIG. 2A. The haptens described in Example 1 were used to direct the antibody epitope towards the di-fluorophenyl-cyclopropyl and thiopropyl substituent groups. As described in Example 1, the linkers for the biotinylated haptens (biotinylated ticagrelor and biotinylated adenosine) were located on the glycol group. This strategy allowed for production of antibodies having binding specificity for the unmodified di-fluorophenyl-cyclopropyl and thiopropyl groups, for biotinylated ticagrelor/TAM, and also enabled for the screening and deselection of antibody libraries that bind adenosine.

Using known techniques, a human scFv phage display library was used to generate scFv antibodies, and specific scFvs were isolated from the library in a series of repeated selection cycles on biotinylated ticagrelor with deselection on biotinylated adenosine, essentially as described in Lloyd et al 2009 PEDS 22: 159-168, incorporated herein by reference. A number of individual clones from the round 2 and round 3 selection outputs were selected, seFvs were expressed in the bacterial periplasm and screened for specificity in three parallel biochemical assays. The assays screened for i) binding to biotinylated ticagrelor (Assay 1), ii) binding to biotinylated adenosine (Assay 2) and iii) binding to biotinylated ticagrelor in the presence of a 50-fold excess of unmodified ticagrelor (Assay 3) to confirm specificity for ticagrelor and not the biotinylated linker.

Assays 1, 2, and 3 were performed using the same general techniques and strategy. Briefly, HTS of crude periplasmic scFv samples for binding to biotinylated ticagrelor or to biotinylated adenosine was performed using HTRF® assay technology. HTRF® (homogeneous time resolved fluorescence) is based upon the principle of TR-FRET (time resolved fluorescence resonance energy transfer). Briefly TR-FRET utilizes the transfer of energy from a donor fluorophore (in this case Europium cryptate) to an acceptor fluorophore (in this case $XL^{665}$). Provided the donor and acceptor fluorophores are in sufficiently close proximity (approx. <10 nm), the excitation of the Europium cryptate donor (337 nm) results in a transfer of energy to the $XL^{665}$ acceptor which in turn emits a fluorescence signal at 665 nm. This technology can be used to sensitively measure biomolecular interactions by attaching the donor and acceptor fluorophores (either directly or indirectly) to each binding partner in the particular interaction. The HTS format for scFv binding to biotinylated ticagrelor (Assay 1) is represented below and relies on the presence of chemical tags on both the biotinylated ticagrelor and his-tagged periplasmic scFv:

Europium crypate streptavidin : biotinylated ticagrelor : scFv-His : anti-His-$XL^{665}$ The assay was performed in a buffer comprising DPBS pH7.4 (Gibco 14190-086), KF (VWR 103444T) (0.4M) and Tween 20 (Sigma P9416) (0.05%) in an assay volume of 10 ul using black shallow well 384 well assay plates (Corning/Costar 3676). The assay was set up by addition of 5 ul of biotinylated ticagrelor (60 nM to give 30 nM final concentration), 2 ul of periplasmic scFv sample (20% final concentration) and 3 ul of a solution containing both Europium cryptate labelled streptavidin (CisBio 610SAKLB) (4.2 nM to give 1.26 nM final concentration) and $XL^{665}$ labelled anti-His antibody (CisBio 61HISXLB) (40 nM to give 12 nM final concentration). Negative binding control wells were set up which contained all of the assay components above except that 2 ul assay buffer was added in place of the periplasmic scFv. Assay plates were incubated for 4 hrs at RT before being read on an Envision plate reader using a standard HTRF read protocol in which samples are excited at 337 nm and time resolved fluorescence emission is measured at both 620 nm and 665 nM.

Raw 665 nm and 620 nm counts were first converted into 665 nm/620 nm ratio values and subsequently results were expressed as Delta F (%) values. Delta F was calculated according to the following equation:

Delta F (%)={((sample 665/620 ratio)−(negative 665/620) ratio))/(negative 665/620 ratio)}×100

(Negative ratio was taken from the negative binding control wells). scFv providing Delta F values of greater than 100% were defined as hits in this assay.

The same protocol as described above was used to perform HTS of crude periplasmic scFv samples for binding to biotinylated adenosine (final assay concentration 30 nM). The format of Assay 2 can be depicted as set out below:

Europium crypate streptavidin:biotinylated adenosine: scFv-His:anti-His-$XL^{665}$ Assay 3 utilized the same protocol as described above to perform HTS that identified crude periplasmic scFv samples showing reduced binding to biotinylated ticagrelor in the presence of excess free unmodified ticagrelor. This protocol was modified from Assay 1 in that Assay 3 was performed in the presence of a 50-fold molar excess of free, unmodified ticagrelor (1500 nM).

Figure 3:
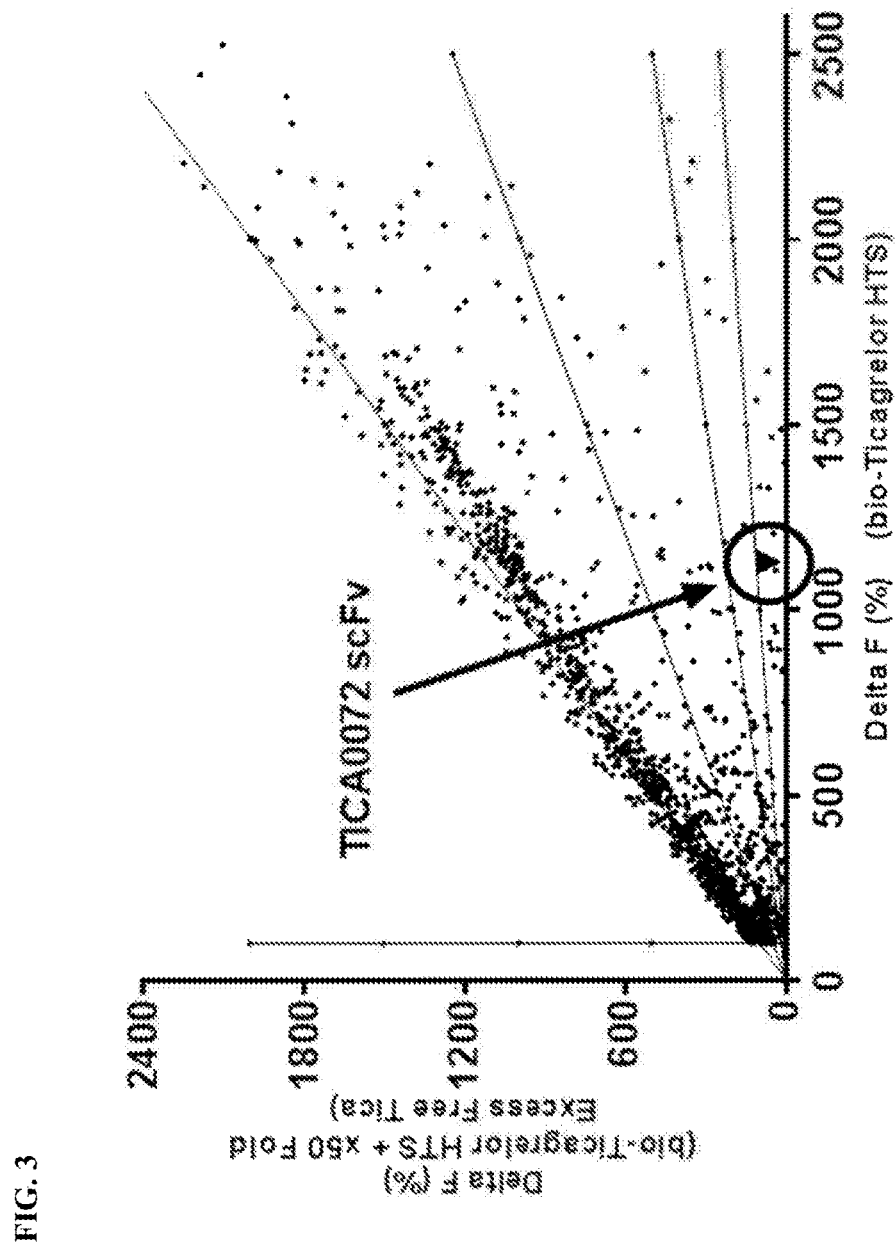
FIG. 3 illustrates correlation of scFv binding to biotinylated linker ticagrelor (x-axis) and binding to biotinylated linker ticagrelor in a 50-fold excess of unmodified ticagrelor (y-axis). The inhibition of scFv binding in the presence of excess unmodified ticagrelor is shown with lines for 0%, 50%, 80% and 90% inhibition.

A hit was defined as binding to biotinylated ticagrelor (Delta F>100% in Assay 1), no binding to biotinylated adenosine (Delta F<25% in Assay 2) and >50% reduced binding to biotinylated ticagrelor in the presence of excess free unmodified ticagrelor. An example correlation of data from Assays 1 and 3 is shown in FIG. 3. A number of scFvs showed limited inhibition in the presence of excess free unmodified ticagrelor, implying they had binding interaction with some component of ticagrelor and the linker. A subset of scFvs were identified in which binding to biotinylated ticagrelor was inhibited (>50%) in the presence of excess free unmodified ticagrelor. scFvs were ranked based on the % inhibition of binding observed in Assay 3 versus Assay 1 (50-80%, 80-90%, >90%) with scFv giving >90% inhibition (including TICA0072) prioritised for further characterisation. Sequence unique scFv hits were converted to Fabs and expressed in CHO cells using standard techniques.

Fab Expression and Purification

Separate HC and LC expression plasmids were used for transient transfection, based on the expression vectors described by Persic et al. 1997. The vectors were modified to contain the EBV origin of replication (OriP). The Fab (HC) vector contained only constant region 1 (CH1) and Hinge regions, CH2 and CH3 were removed. HC and LC DNA was added to 150 mM NaCl and 25-kDa linear PEI (Polysciences Europe, Germany 23966), according to manufacturer's recommendations. The DNA-PEI complex was then added to Chinese Hamster Ovary wild type (CHO wt) cells derived from a CHOKI cell line (ECACC No: 85051005) adapted for suspension culture (Daramola O, et al 2014). After 7 days the cells were harvested by centrifugation and the supernatants filtered. The cell culture supernatant containing the Fab protein was loaded directly onto a chromatography column packed with 5 ml CaptureSelect IgG-CH1 (Life Technologies, Carlsbad, USA) at a flow rate of 5 mL/min using an Akta Purifier (GE Healthcare). The columns were equilibrated and washed with Phosphate Buffered Saline (PBS) pH 7.2 and eluted with 20 mM sodium citrate, 150 mM sodium chloride, pH 3.5 (Capture- Select IgG-CH1) according to the resin manufacturer's instructions. Eluted Fab was adjusted to pH 5.5 and filtered (0.22 µm Steriflip, Millipore EMD, Bethdesa, USA) prior to analysis. Protein concentration was determined by absorbance at 280 nm using a DUS20 UV/vis spectrophotometer (Beckman Coulter, Brea, USA). Sample purity was determined using a TSKgel G3000SWxl column (Tosoh Bioscience, Tokyo, Japan) and a 1100 HPLC system (Agilent Technologies, Santa Clara, USA) running at 1.0 ml/min.

Example 3: Anti-Ticagrelor/TAM Fabs

Figure 4:
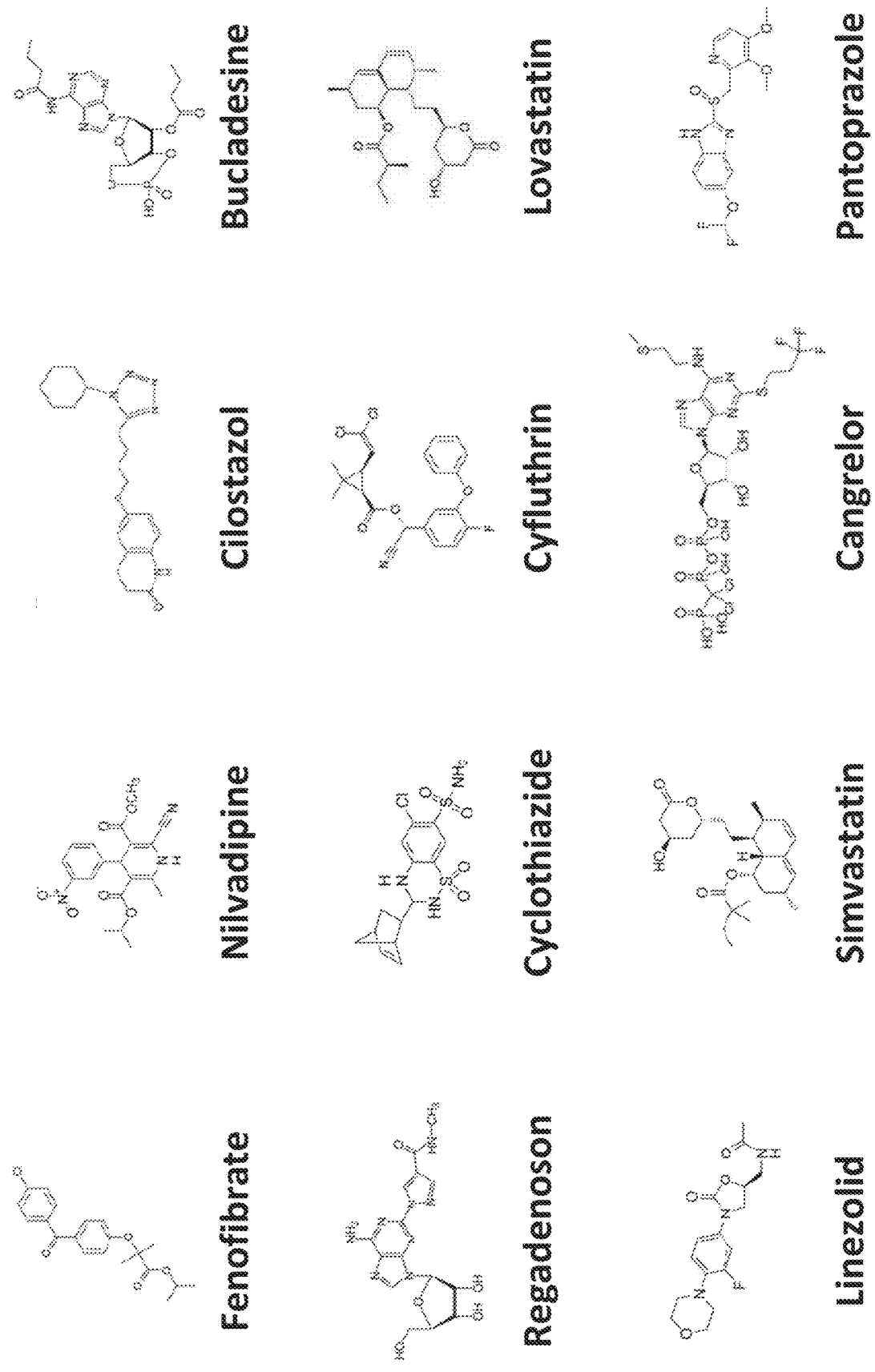
FIG. 4 shows compounds identified with some degree of 2D, 3D or electrostatic similarity to ticagrelor.
Figure 5A:
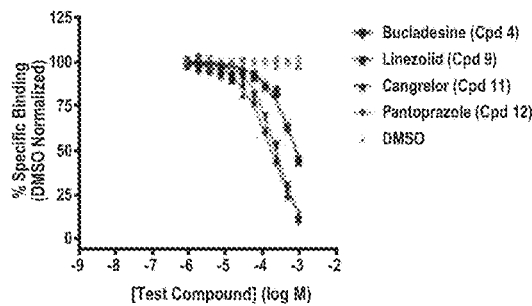
FIG. 5A-F provides Selectivity studies for TICA0049 and TICA0072 Fab.
Figure 5D:
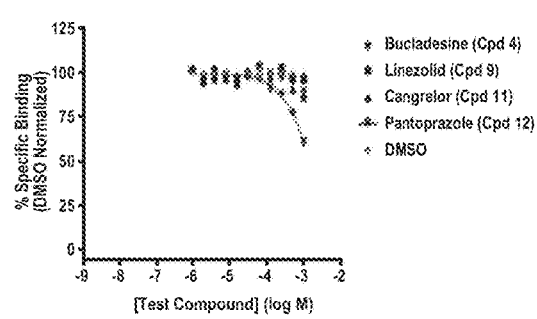
Figure 5B:
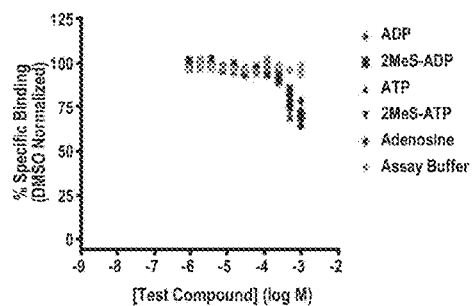
Figure 5E:
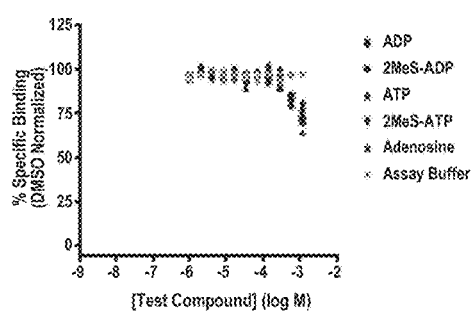
Figure 5C:
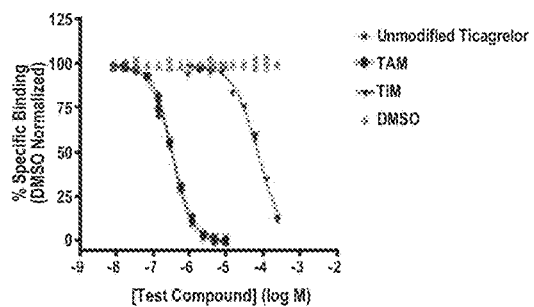
Figure 5F:
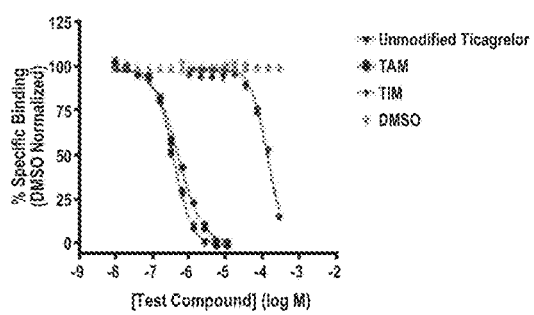

A structural database ("DrugsDB", Oprea T. I et al 2011 Mol. Inform. 30(2-3), 100-111, incorporated herein by reference) containing marketed drugs was interrogated in order to identify molecules that have some structural similarity to ticagrelor. Once identified, these structurally similar molecules were used to test the the binding specificity of Fabs beyond adenosine and its phosphorylated forms (e.g., ADP and ATP). The database was interrogated for molecules having 2D fingerprint similarity, 3D shape, and electrostatic similarity to ticagrelor, based on ticagrelor x-ray and NMR structures. From this in silico analysis a panel of 12 compounds were selected that included six potential co-medications. The structures of these compounds are shown in FIG. 4.

Specificity was investigated in a competition binding assay format in which the ability or otherwise of each test compound to competitively inhibit the interaction of biotinylated ticagrelor with the relevant Fab was tested. A HTRF® competition assay format was used as set out below in which the aim was to measure the competition of biotinylated ticagrelor binding to each His-Fab by a panel of test compounds:

Europium crypate anti-His antibody: test His-Fab: biotinylated ticagrelor: XL$^{665}$ labelled streptavidin.

This basic assay format was used to assess the selectivity profile of lead Fabs from the end of both the lead isolation and lead optimization phases and for the purposes of these studies Fabs were generated using a His-Fab expression vector.

The assay was performed in a buffer comprising DPBS pH7.4 (Gibco 14190-086), KF (VWR 103444T) (0.4M) and BSA (PAA K05-013) (0.1%) in an assay volume of 20 ul in black shallow well 384 well assay plates (Corning/Costar 3676). The assay set up involved the addition of 5 ul of biotinylated ticagrelor, 5 ul of a titration of each test selectivity compound, 5 ul of the relevant His-Fab and 5 ul of a combined solution containing both Europium cryptate labelled anti-His antibody (CisBio 61HISKLB) (5.33 nM to give 1.33 nM final concentration) and XL$^{665}$ labelled streptavidin (CisBio 611SAXLB) (40 nM to give 10 nM final concentration). Total Binding control wells were set up which contained all of the assay components above except that 5 ul assay buffer was added in place of the test selectivity compound addition. Negative Binding control wells were set up which contained all of the assay components included in the Total Binding control wells except that 5ul assay buffer was added in place of the His-Fab addition. Test compound serial titrations were either ½ or ⅓ depending on the particular experiment and top final assay compound concentrations were optimized on a compound specific basis. The concentration of biotinylated ticagrelor and His-Fab was optimized on a Fab specific basis in separate experiments. For the four Fabs investigated at the end of the lead isolation phase (TICA0010, TICA0049, TICA0053 and TICA0072) the final assay reagent concentrations used are set out in Table 1 below:

TABLE 1

| Antibody ID | [Antibody] (nM) | [biotinylated ticagrelor] (nM) |
|---|---|---|
| TICA0039 | 16.0 | 139.9 |
| TICA0049 | 16.0 | 37.9 |
| TICA0053 | 16.0 | 70.7 |
| TICA0072 | 8.0 | 17.6 |

For the two Fabs investigated at the end of the lead optimization phase (TICA0162 and TICA0212) the final assay reagent concentrations used were 5nM biotinylated ticagrelor and 1 nM His Fab in both cases. Several of the test selectivity compounds used in these experiments were dissolved in 100% DMSO and a vehicle related reduction in assay signal can begin to occur at concentrations above approximately 1% DMSO. In order to enable subsequent normalization of data to correct for any such vehicle related effects parallel titrations of DMSO alone were included in most experiments in which the final assay DMSO concentrations mirrored those of the test compound serial dilutions. At the end of the set up procedure that assay was incubated for 3hrs at RT before being read on an Envision plate reader using a standard read protocol.

For subsequent data analysis raw 665 nm and 620 nM counts were first converted into 665 nm/620 nm ratio values which were then used to calculate % Delta F values according to the equation set out in Assay 1. The negative ratio value used in the calculation of % Delta F was derived from the Negative Binding control wells. % Delta F values were then used to calculate % Specific Binding values according to the equation below:

Specific Binding (%)={(Sample Delta F−Negative Binding Delta F)/(Total Binding Delta F−Negative Binding Delta F)}×100

For standard calculations of % Specific Binding Total Binding Delta F was taken from Total Binding control wells which contained all of the aforementioned components of the assay but without inclusion of any competing test compound.

In those experiments where DMSO normalization was applied DMSO normalised % Specific Binding was calculated essentially according to the equation above except that in this case Total Binding Delta F was taken from wells containing all of the components in the Total Binding control wells as well as DMSO at a concentration equivalent to that in the relevant sample well.

The results from initial experiments of this type are summarized in Table 2. In three of the four initial Fabs that were investigated (TICA0010. TICA0049 and TICA0053) the compound Cangrelor showed competitive inhibition of Fab binding to biotinylated ticagrelor. In the case of TICA0049 both Pantoprazole and Linezolid exhibited partial competitive inhibition. As shown in Table 2, TICA0072 Fab exhibited no inhibition with eleven of the twelve compounds, with pantoprazole showing weak, partial inhibition.

Inhibition with unmodified ticagrelor and TAM was observed for all four Fabs tested in this first series of experiments with IC$_{50}$ values falling in a range of 0.1 µM to 0.5 µM. Competitive inhibition was also detected with TIM for two of the four Fabs (TICA0049 and TICA0072) however, with IC$_{50}$ values of >50 µM, suggesting a greatly reduced affinity for TIM relative to unmodified ticagrelor and TAM. Based on the results in Table 2 TICA0072 was identified as having the most favorable selectivity profile. TICA0049 was identified as a potential back up based on the criteria that this Fab showed the least binding to Cangrelor within the remaining three Fabs.

TABLE 2

Relative $IC_{50}$ values for each of 12 tested compounds (FIG. 4) and unmodified ticagrelor, TAM, and TIM for inhibition of biotinylated ticagrelor binding to each test Fab.

| Compound | IC50 (uM) for Various Compounds for lead his-Fabs | | | |
|---|---|---|---|---|
| | TICA00l0 | TICA0049 | TICA0053 | TICA0072 |
| Fenofibrate | NI | NI | NI | NI |
| Nilvadipine | NI | NI | NI | NI |
| Cilostazol | NI | NI | NI | NI |
| Bucladesine | NI | NI | NI | NI |
| Regadenoson | NI | NI | NI | NI |
| Cyclothiazide | NI | NI | NI | NI |
| Cyfluthrin | NI | NI | NI | NI |
| Lovastatin | NI | NI | NI | NI |
| Linezolid | NI | 467.1 | NI | NI |
| Simvastatin | NI | NI | NI | NI |
| Cangrelor | 102.4 | 207.9 | 17.5 | NI |
| Pantoprazole | NI | 263.7 | NI | 498.0 |
| Ticagrelor | 0.122 | 0.257 | 0.109 | 0.113 |
| TAM | 0.124 | 0.412 | 0.134 | 0.299 |
| TIM | NI | 53.4 | NI | 54.4 |

NI is no inhibition.

In a second series of experiments further selectivity data was generated for TICA0049 and TICA0072 Fabs in which a subset of four of the twelve compounds listed in FIG. 4 were retested along with ticagrelor, TAM and TIM and several adenosine related compounds. Here, in a refinement to the earlier investigations in Table 2, experiments were designed in order to enable normalisation of percent specific binding values to correct for any non-specific vehicle related effects due to DMSO. Example plotted data from this second series of experiments is shown in FIG. 5A-F along with tabulated $IC_{50}$ values in Table 3.

TABLE 3

Example $IC_{50}$ results for a subset of four of the twelve compounds listed in FIG. 4, ticagrelor, TAM, TIM and several adenosine family compounds in competition binding selectivity studies (DMSO normalised)

| Compound | TICA0049 | TICA0072 |
|---|---|---|
| Adenosine | NI | NI |
| ADP | NI | NI |
| 2MeS ADP | NI | NI |
| ATP | NI | NI |
| 2MeSATP | NI | NI |
| Bucladesine | 864.9 | NI |
| Linezolid | 902.0 | NI |
| Cangrelor | 188.4 | NI |
| Pantoprazole | 243.5 | 1546.0 |
| Ticagrelor | 0.368 | 0.356 |
| TAM | 0.366 | 0.483 |
| TIM | 74.8 | 119.5 |

As with the earlier experiments TICA0072 showed the most favourable selectivity profile with only pantoprazole showing weak, partial inhibition ($IC_{50}$>1500 μM) from within the four compounds tested. In the case of TICA0049 significant inhibition was observed with Cangrelor and Pantoprazole with weak inhibition observed for Linezolid and Bucladesine. It should be noted that subtle differences in absolute $IC_{50}$ values between the first and second series of experiments for certain test compounds do not fundamentally change the overall conclusions. Such differences may stem from the fact that DMSO normalisation was incorporated into the second series of experiments in combination with the fact that in several cases we were attempting to measure very weak inhibition.

For both TICA0049 and TICA0072 measured $IC_{50}$ values for ticagrelor and TAM were in the range 0.3 μM to 0.5 μM with $IC_{50}$ values for TIM at greater than 2 log values higher at 74.8 μM and 119.5 μM, respectively. A trace of inhibition was observed with adenosine, ADP. ATP and the methyl-thio derivatives of the latter two compounds for both TICA0049 and TICA0072 Fabs however this was only detected at the highest compound concentrations tested and was not considered significant.

It is concluded that TICA0072 was the only Fab considered specific for ticagrelor and TAM.

Example 4: Affinity Measurement of Anti-Ticagrelor/TAM Fabs

The affinity of the anti-ticagrelor Fabs generated above was determined using Biolayer Interferometry on the Octet Red384. For the affinity measurement anti-ticagrelor Fab antibodies were diluted to a concentration of 2× the final assay concentration in assay buffer (PBS, Tween20 0.05%, BSA 0.02%) e.g. 200 nM. A 10-point 2-fold serial dilution of ticagrelor was prepared in a Greiner polypropylene 96-well plate. Equal volumes, (e.g. 70 μL plus 70 μL) of diluted antibody and free ticagrelor were then transferred to a second Greiner polypropylene plate. The samples were mixed by pipetting, covered with a plate seal and allowed to equilibrate for 3-5 days at room temperature. Following equilibration 60 μL of the antibody/ticagrelor titrations was transferred, in duplicate, to a 384 well black tilted bottom polypropylene plate. Biotinylated ticagrelor was diluted to 250 nM in assay buffer and added to alternate wells of the first 2 columns of the 384 well assay plate, the remaining wells contained assay buffer only. Streptavidin biosensors were pre-soaked in assay buffer for at least 10 minutes. Sample plates and biosensors were then loaded onto the stage of the OctetRed384.

All assays were performed at room temperature. Following baseline equilibration for 60 sec in assay buffer, biotinylated ticagrelor was loaded on the streptavidin biosensors for 300 sec, followed by assay buffer for 600 sec to establish a new baseline. The antibody/ticagrelor mixtures were then allowed to associate with the biotinylated ticagrelor sensor surface for 30-600 sec, depending on the concentration of antibody used. The resulting association phase data were analyzed using the OctetRed Data Analysis software. The signals were aligned to baseline and the reference sensor signal (no antibody control) was subtracted for each sample, then the data were exported for analysis using the KinExA n-Curve Analysis software. Using the Constant Partner analysis the equilibrium KD for the anti-ticagrelor Fab antibodies was determined. The data showed that Fabs TICA0072 and TICA0049 had affinities for ticagrelor of 7.4 nM and 11.6 nM respectively (Table 4).

TABLE 4

Equilibrium affinity analysis for anti-ticagrelor Fabs

| Antibody ID | Hapten | Equilibrium KD | 95% Confidence Interval |
|---|---|---|---|
| TICA0072 | Ticagrelor | 7.43 nM | 1.75-21.46 nM |
| TICA0049 | Ticagrelor | 11.6 nM | 1.7-66.5 nM |

Example 5: Optimization of Anti-Ticagrelor/TAM Antibody TICA0072

The antibody TICA0072 was optimized using affinity-based phage selections. Large scFv libraries derived from the lead scFv sequence were created by oligonucleotide-directed mutagenesis of the variable heavy (VH) complementarity determining regions (CDR) 1. 2 or 3 or variable light (VL) chain CDRs 1, 2 or 3 using standard molecular biology techniques as described (Clackson and Lowman 2004 Practical Approach Series 266). The libraries were subjected to affinity-based phage display selections in order to select variants with a higher affinity to ticagrelor and TAM. In brief, the scFv-phage particles were incubated in solution with reducing concentrations of biotinylated ticagrelor (a typical example would be 20 nM to 20 pM over four rounds of selection), essentially as described previously (Thompson et al 1996 J Mol Biol. 256 (1): 77-88). Crude scFv-containing periplasmic extracts were prepared for a representative number of individual scFv from the CDR-targeted selection outputs and screened in a HTRFS epitope competition assay format designed to screen for improvements in affinity relative to TICA072.

Briefly, in order to screen for scFv and Fab variants of improved affinity a HTRFRepitope competition assay was implemented based on competition, by test scFv variants, of the interaction between the parent TICA0072 IgG and biotinylated ticagrelor. This assay was used both as a primary single point HTS to screen crude periplasmic extract scFv samples as well as a multi-point secondary profiling assay in order to measure improvements in $IC_{50}$ values for both purified scFv and Fab variants versus parent TICA0072. Although epitope competition assays, such as the one described here, are not generally used to determine absolute affinity values such assays can be used as the basis of an affinity based HTS. Furthermore, fold improvements in $IC_{50}$ for purified scFv/Fab variants (relative to the parent scFv/Fab) can provide a good indicator of overall fold gains in affinity and can represent an effective way to affinity rank scFv/Fab variants in lead optimization campaigns. The format for the TICA0072 parent IgG based epitope competition assay described here is set out below:

Europium labelled streptavidin: biotinylated ticagrelor: TICA0072 IgG: $XL^{665}$ labelled anti-human-Fc antibody The assay was performed in a buffer comprising DPBS pH7.4 (Gibco 14190-086), KF (VWR 103444T) (0.4M) and Tween 20 (Sigma P9416) (0.05%) in black shallow well 384 well assay plates (Corning/Costar 3676). For single point testing of crude periplasmic scFv variants an assay volume of 10 ul was used however a 20 ul assay volume was used when testing purified scFv and Fab in multipoint secondary $IC_{50}$ profiling assays.

For single point HTS the assay was set up by adding 3 ul of TICA0072 IgG (53.3 nM to give 16 nM final concentration), 2 ul of crude periplasmic extract scFv sample, 2.5 ul of biotinylated ticagrelor (8 nM to give 2 nM final concentration) and 2.5 ul of a combined solution containing Europium labelled streptavidin (CisBio 610SAKLB) (3 nM for 0.75 nM final assay concentration) and $XL^{665}$ labelled anti-human-Fc antibody (CisBio 61HFCXLB) (30 nM to give 7.5 nM final assay concentration). Parent TICA0072 crude periplasmic scFv was used as benchmark and the HTS was configured to identify variants giving improved inhibition relative to parent. Total Binding Control Wells contained all assay components except that 2 ul assay buffer was added in place of the scFv sample. Negative Binding control wells contained all of the components of the Total Binding control wells except that 3 ul of assay buffer was added in place of the TICA0072 IgG.

For multipoint $IC_{50}$ testing of purified scFv/Fab variants the assay was set up by adding 5 ul of TICA0072 IgG (53.3 nM to give 16 nM final concentration), 5 ul of a ⅓ titration of purified test scFv or Fab variant, 5 ul of biotinylated ticagrelor (8 nM to give 2 nM final concentration (scFv profiling), 4 nM to give 1 nM final assay concentration (Fab profiling)) and 5 ul of a combined solution containing Europium labelled streptavidin (CisBio 610SAKLB) (3 nM for 0.75 nM final assay concentration) and $XL^{665}$ labelled anti-human-Fc antibody (CisBio 61HFCXLB) (30 nM to give 7.5 nM final assay concentration). Purified parent TICA0072 (scFv or Fab) was used as a benchmark in all experiments such that improvements in $IC_{50}$ measured with optimized variants (scFv or Fab) could be expressed as fold improvements over parent TICA0072. Total Binding Control Wells contained all assay components except that 5 ul assay buffer was added in place of the purified scFv or Fab sample. Negative Binding control wells contained all of the components of the Total Binding control wells except that 5 ul of assay buffer was added in place of the TICA0072 IgG.

In both single point HTS and multipoint $IC_{50}$ profiling versions of the assay. plates were incubated for 3 hrs at RT before being read on an Envision plate reader using a standard HTRF read protocol in which samples are excited at 337 nm and time resolved fluorescence emission is measured at both 620 nm and 665 nM.

Raw 665 nm and 620 nm counts were used to calculate Delta F (%) and % Specific Binding according to the equations described earlier in Assays 1 and 4, respectively. For multipoint secondary profiling experiments $IC_{50}$ values were determined using Graphpad Prism software using sigmoidal dose response (variable slope) curve fitting (4 parameter logistic equation).

Hits identified in the screen, i.e. scFv variants which showed a significantly improved inhibitory effect when compared to parent TICA0072 scFv, were subjected to DNA sequencing, and unique variants from variable heavy CDR1, CDR2 or CDR3 and variable light library CDR1, CDR2 or CDR3 outputs were then produced as purified scFv and retested in the same assay to determine concentration response $IC_{50}$ curves. The scFv variants showing the most improved $IC_{50}$ values were then produced as Fabs and tested in a second generation epitope competition assay, described below.

Second Generation Epitope Competition Assay for Screening/Ranking of Highest Affinity Fab In order to discriminate effectively between very high affinity purified Fab at the end of the lead optimization campaign a further HTRF® epitope competition assay was implemented however in this case the assay was based upon competitive inhibition of an intermediate affinity optimized TICA0072 lineage IgG (TICA0159) binding to biotinylated ticagrelor as opposed the parent TICA0072 IgG. This assay was used only in multipoint $IC_{50}$ profiling format (as opposed to HTS format) and was performed essentially identically to the method given in Assay 5 (above) for multipoint $IC_{50}$ profiling of purified Fab variants in the parent TICA0072 IgG based epitope competition assay. The only difference being that TICA0159 IgG was used in place of TICA0072 IgG at the appropriate point in the assay set up but at the same 16nM final assay concentration. In all other respects this assay was performed exactly as described above in the multipoint secondary profiling version for purified Fab.

The second generation assay replaced TICA0072 with a partially optimized antibody TICA0159 to enable more effective discrimination and ranking of the highest affinity Fabs than was possible in the TICA0072 based epitope competition assay.

Figure 6:
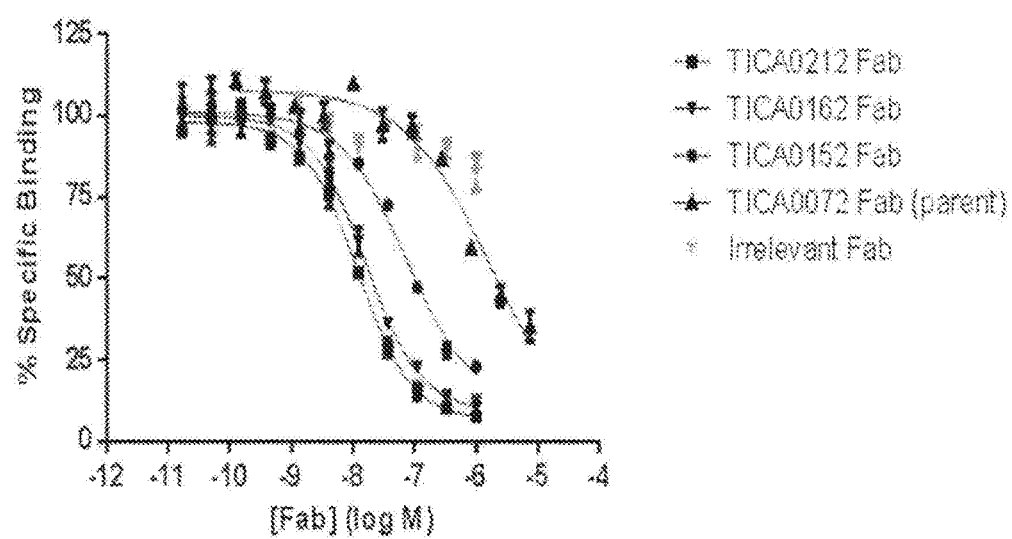
FIG. 6 provides competition curves for parent TICA0072 and optimized variants TICA0152, TICA0162 and TICA0212 Fabs in the second generation epitope competition assay.

The most improved VH was identified as CDR3 variant TICA0162. The most improved VL was identified as CDR3 variant TICA0152. To generate further affinity improvement the different CDRs from improved antibodies were combined into new Fabs using standard molecular biology techniques. From this recombination work the combination of TICA0162 and TICA0152 generated a new Fab TICA0212 with a further improved epitope competition profile. Plotted competition curves for TICA0072, TICA0152, TICA0162 and TICA0212 Fab in the second generation epitope competition assay are shown in FIG. 6 with measured $IC_{50}$ values in Table 5. TICA0212 shows approximately 2 log improvement in $IC_{50}$ relative to the parent TICA0072 Fab.

TABLE 5

$IC_{50}$ data for listed optimized anti-ticagrelor Fabs in the second generation epitope competition assay.

| Fab | $IC_{50}$ (nM) | Fold Improved |
|---|---|---|
| TICA0072 | 1714.0 | 0 |
| TICA0152 | 73.5 | 23.3 |
| TICA0162 | 16.3 | 105.2 |
| TICA0212 | 12.0 | 142.8 |

Example 6: Affinity Measurement of Optimized Anti-Ticagrelor/TAM Fabs

The affinity of anti-ticagrelor/TAM Fabs generated in Example 5 was determined using the KinExA3200. For the KinExA affinity measurement, beads (600 mg Azlactone beads) were first prepared by reacting them overnight with 1 mg streptavidin in 50 mM $NaHCO_3$. Following blocking with 2 changes of Tris buffer (1M Tris pH 8.7, 10 mg/mL BSA) the streptavidin coated beads were resuspended in a total volume of 8 mL. Beads (1.33 mL, equivalent to 100 mg original dry Azlactone beads) were washed completely with PBS, then allowed to bind to approximately 2.5 µg biotin-ticagrelor in 1 mL PBS for 10 minutes with occasional agitation. The resulting biotin-ticagrelor coated beads were washed with PBS, then resuspended in 50 mL PBS containing 0.1% BSA and 0.02% $NaN_3$ and stored at room temperature until transfer to the KinExA bead vial.

Antibody/ticagrelor sample preparation was carried out essentially as described in the previous method. Anti-ticagrelor Fab antibodies were diluted to a concentration of 2 times the final assay concentration in assay buffer (PBS. Tween20 0.05%, BSA 0.02%, 0.02% $NaN_3$) e.g. 200 nM. A 10-point 2-fold serial dilution of ticagrelor was prepared in Falcon 50 ml polypropylene tubes. Equal volumes, e.g. 5 mL plus 5 mL, of diluted antibody and free ticagrelor were then transferred to a second Falcon polypropylene tube. The samples were mixed by pipetting and allowed to equilibrate for 3-5 days at room temperature. Following equilibration the sample tubes were transferred to the KinExA 3200 for analysis.

All assays were performed at room temperature. The antibody/ticagrelor mixtures were sampled and allowed to mix with the bio-ticagrelor beads while the unbound free ticagrelor was washed away. Bound antibody was then detected using DyLight649 labelled mouse anti-human Heavy and Light chain antibody. Sample volume (300-1300 µL) and injection time (90-120 s) varied with concentration, and 2 -3 reads were varied out per sample. The data were analysed using the KinExA n-Curve Analysis software. Using the Constant Partner analysis the equilibrium KD for the anti-ticagrelor Fab antibodies was determined.

As in the prior Example, Fabs were allowed to equilibrate at room temperature in the presence of either unmodified ticagrelor or TAM at concentrations from 20-fold excess. Biotinylated ticagrelor was loaded on to the surface of streptavidin coated beads. Following equilibration, the remaining free antibody was allowed to bind to the biotinylated ticagrelor. Bound antibody was then detected using a DyLight649 labelled mouse anti-human Heavy and Light chain detection antibody. Titrations of free ticagrelor or TAM were prepared with at least three different fixed concentrations of antibody to generate separate titration profiles with at least a 10-fold shift in apparent KD. The data were analysed using the KinExA Pro n-Curve analysis software to determine equilibrium KD for free ticagrelor or TAM. Fab TICA0212 had an affinity for unmodified ticagrelor and TAM of around 20 pM (Table 6). From the equilibrium data TICA0212 demonstrates equivalent high affinity (~20 pM) binding to ticagrelor and TAM.

TABLE 6

Equilibrium affinity analysis for anti-Ticagrelor/TAM Fabs

| Antibody ID | CDR3 Seqs. (SEQ ID NO) | Hapten | Equilibrium KD | 95% C. I. |
|---|---|---|---|---|
| TICA0072 | VH GSHLY$^{99}$ DFW$^{100b}$ SASHPPNDALAI (35) <br> VL GTW$^{91}$ D$^{92}$I$^{93}$S$^{94}$LSAGL (40) | Ticagrelor | 7.4 nM | 1.8-21.5 nM |
| TICA0152 | VH GSHLYDFWSASHPPNDALAI (65) <br> VL GTWLYDRAVGL (70) | Ticagrelor | 43.17 pM | 2.8-119.2 pM |
| TICA0162 | VH GSFDYYFWSASHPPNDALAI (55) <br> VL GTWDISLSAGL (60) | Ticagrelor | 162.48 pM | 125.4-206.3 pM |

TABLE 6-continued

Equilibrium affinity analysis for anti-Ticagrelor/TAM Fabs

| Antibody ID | CDR3 Seqs. (SEQ ID NO) | Hapten | Equilibrium KD | 95% C. I. |
|---|---|---|---|---|
| TICA0212 | VH GSFDYYFWSASHPPNDALAI (75) | Ticagrelor | 19.6 pM | 13.0-28.7 pM |
| (MEDI2452) | VL GTWLYDRAVGL (80) | TAM | 19.7 pM | 4.9-44.7 pM |
|  |  | TIM | ~20 Nm |  |

Changes in sequence residues from parental TICA0072 are bolded, and kabat numbers are identified for certain residues in TICA0072.

Example 7: Specificity of Anti-Ticagrelor/TAM Fab TICA0162 and TICA0212

The specificity of the Fabs, TICA0162 and TICA0212, was tested as in example 3 and normalised against DMSO. A summary table of all available selectivity data for TICA0162 and TICA0212 is included in Table 7. In addition example plotted data from an experiment in which five of the twelve compounds listed in FIG. 4 were tested alongside ticagrelor, TAM, TIM and several adenosine family compounds is shown in FIG. 7A-F.

TABLE 7

Relative IC$_{50}$ values of the twelve structurally related compounds in addition to ticagrelor, TAM, TIM and adenosine family compounds for inhibition of biotinylated ticagrelor binding to TICA0162 and TICA0212 Fab.

| Compound | IC50 (uM) for Various Compounds for lead his-Fabs | |
|---|---|---|
|  | TICA0162 | TICA0212 |
| Fenofibrate | NI | NI |
| Nilvadipine | NI | NI |
| Cilostazol | NI (n = 2) | NI (n = 2) |
| Bucladesine | NI | NI |
| Regadenoson | NI (n = 2) | NI (n = 2) |
| Cyclothiazide | >1000 (n = 2) | NI (n = 2) |
| Cyfluthrin | NI | NI |
| Lovastatin | NI | NI |
| Linezolid | NI | NI |
| Simvastatin | NI (n = 2) | NI (n = 2) |
| Cangrelor | NI | NI |
| Pantoprazole | >1000 (n = 2) | NI (n = 2) |
| Adenosine | NI | NI |
| ADP | NI | NI |
| 2MeS-APD | NI | NI |
| ATP | NI | NI |
| 2MeS-ATP | NI | NI |
| Ticagrelor | 0.023 (n = 2) | 0.035 (n = 2) |
| TAM | 0.032 (n = 2) | 0.031 (n = 2) |
| TIM | 19.8 (n = 2) | 28.8 (n = 2) |

NI is no inhibition.

As illustrated by the data TICA0212 (MEDI2452) has essentially equivalent binding specificity to ticagrelor and TAM, and weaker binding to TIM. In addition MEDI2452/TICA0212 did not show significant binding to any other structurally related drugs or adenosine related compounds.

Example 8: Protein Prystallography

TICA0072 with a C-terminal his-tag was concentrated in PBS to 9 mg/ml. Complex formation was achieved by the addition of 1 mM ticagrelor dissolved in DMSO. The complex was incubated in room temperature for 2 hours before crystallization trials were set up using the vapor diffusion method with sitting drops. Broad screening was performed using 3 commercial screens and several hits were obtained. Best diffracting crystals were obtained from a grid optimization of a Morpheus® (Molecular Dimensions, UK) hit. The crystals used for structure determination was grown at 20° C. by mixing equal volumes of TICA0072-ticagrelor complex and a reservoir solution of 12.8% PEG 3350, 12.8% PEG 1000, 12.8% MPD. 1.7% 1.6-Hexanediol, 1.7% 1-Butanol, 1.7% 1,2-Propanediol, 1.7% 2-Propanol, 1.7% 1,4 butanediol, 1.79% 1.3-Propanediol, 25 mM Imidazole, 25 mM Sodium Cacodylate, 25 mM MES and 25 mM Bis-Tris pH 6.5. Crystals were flash-frozen in liquid nitrogen without the addition of any cryo protectant.

TICA0212/MEDI2452 in PBS at a concentration of around 15 mg/ml was mixed with Ticagrelor to a concentration of 1 mM and incubated 2 hours at room temperature before broad screening was performed. No spontaneous hits were obtained. Seeds from TICA0072-Ticagrelor crystals were prepared by crushing several crystals in 30ul well solution and used in MMS (microseed matrix screening) into broad commercial screens. Several hits were obtained but the crystals used for structure determination was grown at 20° C. from a condition of 20% glycerol, 20% PEG 4000, 10% 2-propanol, 0.1 M NaCl and 0.5 M NaAcetate pH 4.6. The drops were set up with 0.2 ul protein, 0.18 ul well solution and 0.02 ul seed stock. Crystals were flash-frozen in liquid nitrogen without the addition of any cryo protectant.

Data were collected at beam line ID23-1 at the European Synchrotron Radiation Facility, Grenoble, France. The data were processed, scaled and further reduced using the Auto-Proc workflow [Vonrhein, C., et al., Acta Cryst. 2011; D67: 293-302], for statistics see Table 8. For TICA0072 initial phasing was done by molecular replacement using a high resolution Fab structure (PDB id code laqk, [Faber C., et al., Immunotechnology. 1998; 3:253-70]) as a starting model. For TICA0212/MEDI2452, the structure for TICA0072 was used as a starting model. Model rebuilding was performed using Coot [Bricogne G., et al., (2011). BUSTER version 2.11.4. Cambridge, United Kingdom: Global Phasing Ltd] and refinement was performed using autobuster [Emsley, P., et al., Acta Crystallogr., Sect. D: Biol. Crystallogr. 2004, D60, 2126-2132]. For statistics for the final models see Table 8.

TABLE 8

Data collection and refinement statistics from Fab ticagrelor co-crystal structures. Values in parenthesis refer to highest-resolution shell.

| Description | TICA0072 | TICA0212 (MEDI2452) |
|---|---|---|
| PDB accession code |  |  |
| Data collection statistics |  |  |
| Radiation source | ESRF/ID23-1 | ESRF/ID23-1 |
| Radiation detector | Pilatus | Pilatus |
| Space group | P21 | P21212 |

TABLE 8-continued

Data collection and refinement statistics from Fab ticagrelor co-crystal structures. Values in parenthesis refer to highest-resolution shell.

| Description | TICA0072 | TICA0212 (MEDI2452) |
|---|---|---|
| Cell dimensions | a = 41.2, b = 72.6, c = 67.8 β = 98.9 | a = 69, b = 173, c = 42 |
| Resolution (Å) | 49-1.7 (1.87-1.7) | 41-2.16 (2.27-2.16) |
| Observed reflections | 143002 | 232480 |
| Unique reflections | 41888 | 36570 |
| Completeness (%) | 97.0 (95.3) | 99.4 (94.7) |
| Mean I/$\sigma_I$ | 13.6 (1.7) | 10.7 (1.2) |
| $R_{sym}$ %[b] | 4.8 (74.4) | 9.7 (27.7) |
| Refinement statistics | | |
| Resolution (Å) | 49-1.7 | 41-2.16 |
| No. protein + ligand atoms | 3308 | 3371 |
| No. solvent atoms | 142 | 87 |
| R (%), Rfree (%) | 19.8, 23.7 | 21.7, 25.7 |
| Wilson B (Å$^2$), Refined <B> (Å$^2$) | 45.6, 48.5 | 42.1, 44.6 |
| Rmsd ideal bond lengths (Å) | 0.008 | 0.010 |
| Bond angles (°) | 1.10 | 1.25 |

The structure of TICA0072 in complex with ticagrelor was determined to 1.7 Å resolution (FIG. 10). The CDRs form a highly concave surface and ticagrelor is inserted deep into the interface between VH and VL domains. This type of binding is commonly observed for small haptens. All CDRs except VL CDR2 are contributing directly to ticagrelor binding and a large portion of VH CDR3 is disordered. Ticagrelor's difluorophenyl group is located in a cavity lined with hydrophobic residues including vernier residues VH Trp47, VL Phe98 and VH CDR3 residue Leu 100L. A key residue in the interaction with ticagrelor is VL Trp91, which is involved both in a pi-stacking against the adenosine-like core and a hydrogen bond to one of the ribose hydroxyl groups at the cyclopentyl moiety. Additional interactions to the adenosine-like core are provided by VH CDR1 His35 and VH CDR3 Tyr99. The thiopropyl substituent stacks against the main chain of the VH CDR2 loop. The hydroxyethyl substituent on the cyclopentyl moiety is protruding into the solvent and does not make any interactions with the Fab.

In the structure of the affinity improved Fab. TICA0212/MEDI2452, the ticagrelor binding is similar to that of TICA0072 with all the interactions mentioned above retained but with some important differences (FIG. 10B). The combination of the VL CDR3 mutations Asp92Leu and Ser94Asp breaks a hydrogen bond within the VL CDR3 loop to create a more "relaxed" structure. The new conformation is correlated with a 15° tilt of the pyrimidine ring about the attachment of the cyclopropyl-difluorophenyl substituent. The new position of the pyrimidine ring brings it approximately 0.2 Å closer to VH CDR3 Tyr99 in TICA0212/MEDI2452 compared to Fab 72. Moreover, VL Ile93Tyr introduces a hydrogen bond donor which makes interactions with the VH CDR3 loop thus defining the binding site further.

The crystal structure for TICA0212/MEDI2452 shows ticagrelor bound in a deep crevice between the $V_H$ and $V_L$ interface. The design strategy of labelling ticagrelor with biotin via a tri-amide linker to the hydroxyethyl group is substantiated as the crystal structure demonstrates the hydroxyethyl group is not involved in any interaction with TICA0212/MEDI2452. This is further supported by the fact that the Fab also binds TAM with identical affinity, which lacks the hydroxyethyl group. TICA0212/MEDI2452 shows weak binding to TIM which lacks the cyclopropyl-difluorophenyl group. In the TICA0212/MEDI2452-ticagrelor complex the cyclopropyl-difluorophenyl group is buried at the bottom of the hydrophobic pocket and must play a key structural role in aligning the ticagrelor adenosine-like core with the VL CDR3 residue Trp L91. As the chemical starting point for ticagrelor was ATP and it retains an adenosine-like core, a critical attribute for antidote specificity was to demonstrate no binding of adenosine. The lead isolation strategy involved both high throughput and detailed specificity analysis and no binding of adenosine was detected either by competitive or direct binding analyses. From the structural analysis the purine ring and ribose group of adenosine might be expected to mimic the interaction of ticagrelor's adenosine-like core. However, the lack of binding may be explained by the absence of two hydrophobic R groups (cyclopropyl-difluorophenyl and thiopropyl) which significantly reduce both the relative shape complementarity and the hydrophobicity of the binding interaction.

An analysis of the structures of the parental TICA0072 and TICA0212/MEDI2452 shows the significance of some of the changes introduced during the affinity maturation. The mutations in $V_L$ CDR3 appear to have particularly high impact, resulting in a different loop conformation and an additional hydrogen bond in TICA0212/MEDI2452 to define the binding cavity. In contrast, contributions from mutations in the $V_H$ CDR3 are structurally less obvious. These observations from the structure are partly confirmed by data for modified antibodies containing modifications in $V_L$ CDR3 (TICA0152) or $V_H$ CDR3 (TICA0162) only, which resulted in 200-fold and 50-fold improvement over TICA0072, respectively. However, although the $V_L$ CDR3 changes appear to have a greater effect, both sets of mutations add significant improvement. It should be noted that the crystal structure is a static picture of the complex and is not able to capture any of the protein and ligand dynamics involved in binding.

Example 9: TICA0212/MEDI2452 Concentration-Dependently Restored Platelet Aggregation in the Presence of Ticagrelor or TAM, In Vitro The extent and potency of TICA0212/MEDI2452 to reverse ticagrelor or TAM mediated inhibition of ADP-induced platelet aggregation was determined in human platelet rich plasma (PRP) using light transmission aggregometry.

For the in vitro human PRP assay, blood was collected from fasted healthy volunteers by vein puncture of vena cephalica. The first 2 mL of blood was discarded prior to collecting aliquots into tubes containing 0.109 M sodium citrate, 1+9 (citrate+blood), to final concentration 10.9 mM. The anticoagulated human blood was centrifuged at 240× g for 15 min. PRP was carefully removed and transferred to a clean vial. Platelet poor plasma (PPP) was prepared by centrifugation of the PRP at 2000× g for 15 min. Light transmission aggregometry (LTA) was evaluated in PRP by the Platelet Aggregation Profiler (PAP-8E, Bio/Data Corporation, PA, USA.). Zero % aggregation was defined as the light transmission of PRP and 100% aggregation was defined as the light transmission of PPP.

PRP was preincubated with 1 μM ticagrelor or TAM for 1 hour before co-incubating with different concentrations of TICA0212 or an isotype control Fab for 30 minutes. Platelet aggregation was initiated by addition of 20 uM ADP and was continuously recorded for 6 min. Data for final aggregation (FA) extent at 6 min was analysed.

Figure 8A:
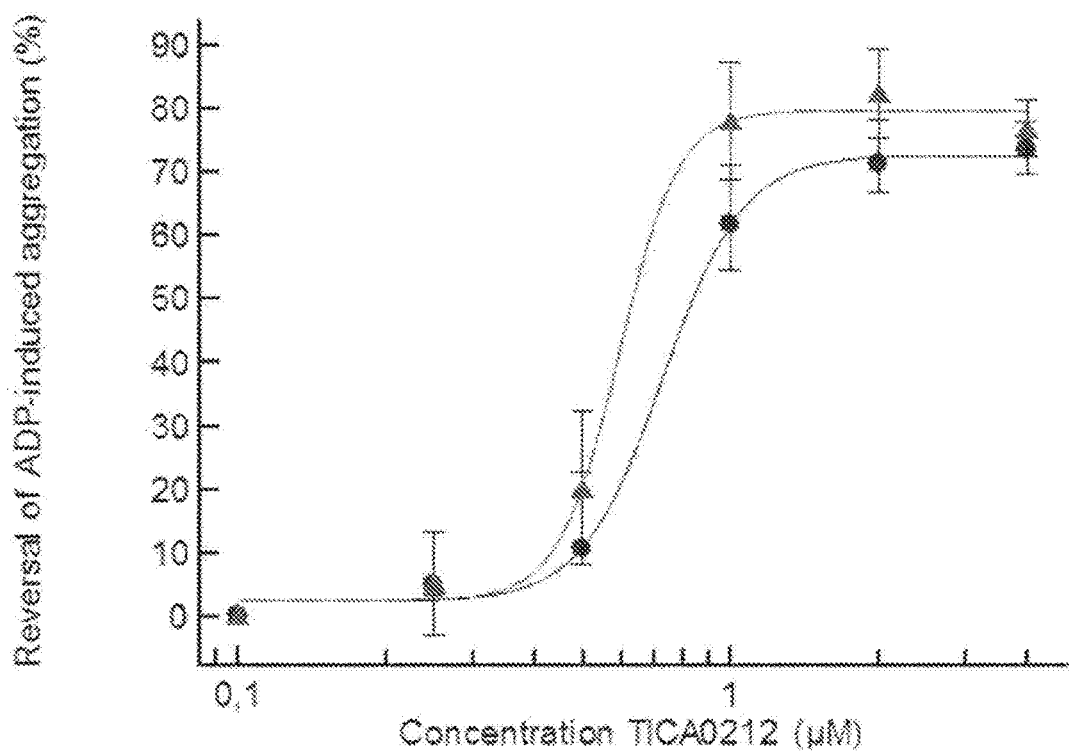
FIG. 8A-C shows the results of TICA0212/MEDI2452 or TICA0072 concentration dependent reversal of ticagrelor.
Figure 8B:
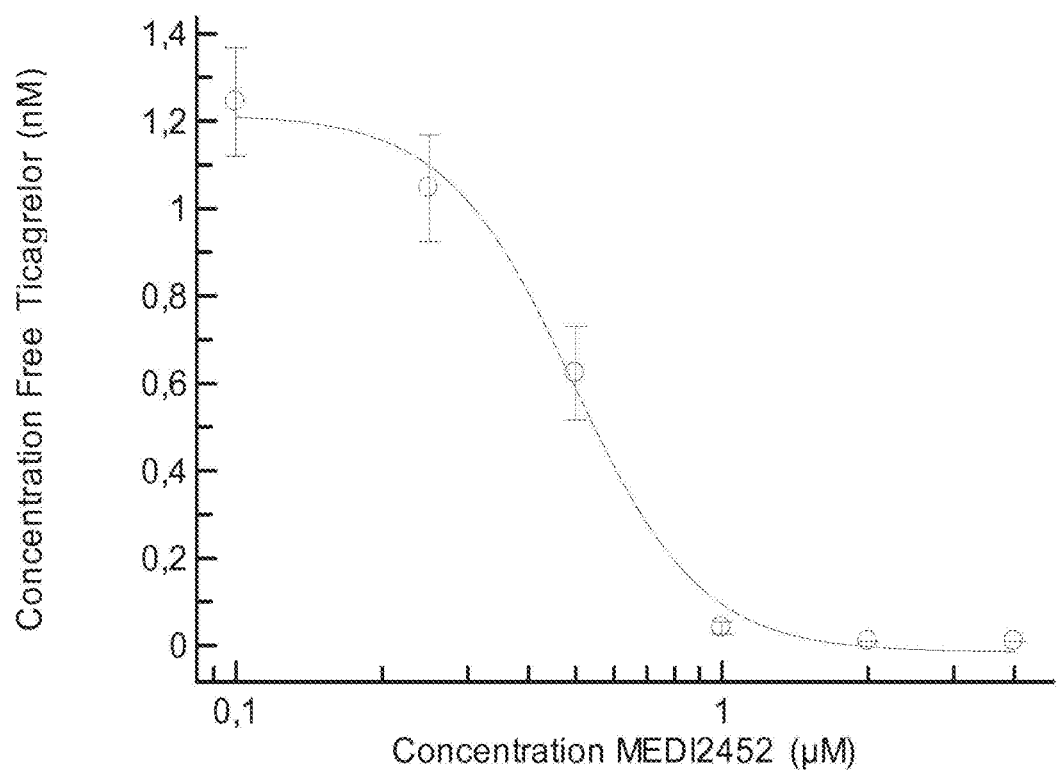
Figure 8C:
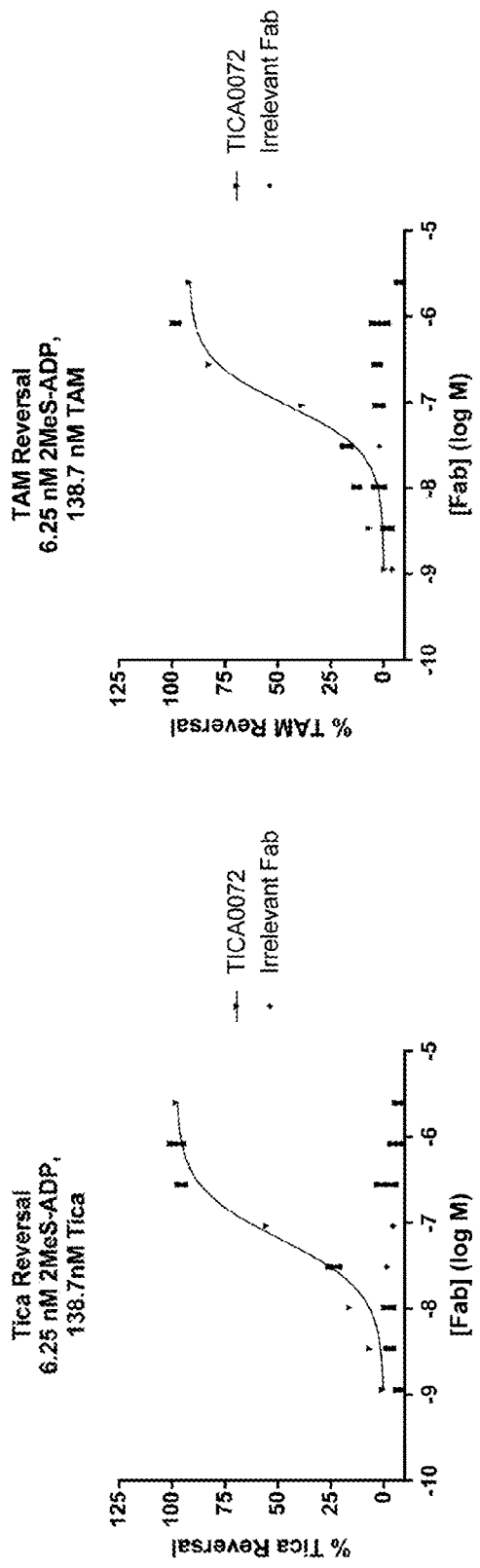

The concentrations of TICA0212/MEDI2452 that gave half-maximum reversal ($IC_{50}$) were calculated. TICA0212/MEDI2452 produced a concentration-dependent reversal of 1 μM ticagrelor and 1 μM TAM mediated inhibition of 20 μM ADP-induced platelet aggregation with calculated mean (n=5) $IC_{50}$ values of 0.64 and 0.78 μM, respectively (FIG. 8A). When evaluated at 1:1 conditions (1 μM TICA0212/MEDI2452: 1 μM ticagrelor or TAM) the mean extent of reversal was 78% and 62%, respectively. Isotype control Fab caused no significant reversal of ticagrelor and TAM ADP-induced platelet aggregation. For example, after 30 min incubation isotype control Fab resulted in −3% and 2% reversal of ticagrelor and TAM, respectively.

From this, the data shows that TICA0212/MEDI2452 can reverse both ticagrelor and TAM mediated inhibition of ADP-induced platelet aggregation in vitro in a concentration dependent manner. Maximal and nearly complete reversal effect was achieved when evaluated in a 1:1 experiment setting, which would be predicted when TICA0212/MEDI2452 binds to ticagrelor or TAM in a 1:1 stoichiometry.

Example 10: TICA0212/MEDI2452 Effectively and Rapidly Restores Platelet Aggregation in the Presence of Ticagrelor or TAM, In Vitro The time of onset of TICA0212/MEDI2452 to reverse ticagrelor or TAM was determined in human platelet rich plasma (PRP) using light transmission aggregometry as in example 8. PRP was preincubated with 1 μM ticagrelor or TAM for 1 hour before adding 1 μM TICA0212/MEDI2452 and co-incubating for 5, 10, 15, 30 and 60 min, or adding an isotype control Fab for 30 min. Platelet aggregation was initiated by addition of 20 μM ADP and was continuously recorded for 6 min. Data for final aggregation (FA) extent at 6 min was analyzed.

TICA0212/MEDI2452 produced similar extent of reversal of ticagrelor mediated inhibition regardless of co-incubation time as mean (n=3) extent of reversal was 85%, 69%, 74%, 80% and 81% after 5, 10, 15, 30 and 60 minutes, respectively. Similarly the mean (n=3) extent of TAM reversal induced by TICA0212/MEDI2452 was 53%, 56%, 58%, 69%, 74% after 5, 10, 15, 30 and 60 minutes, respectively. TICA0212/MEDI2452 rapidly and effectively reversed ticagrelor and mediated inhibition of ADP-induced platelet aggregation. No reversal. mean (n=3)−2%, was present after 30 min co-incubation with the isotype control Fab. From this data. TICA0212/MEDI2452 was shown to rapidly and effectively reverse both ticagrelor and TAM mediated inhibition of ADP-induced aggregation when evaluated in a 1:1 experiment setting.

Example 11: TICA0212/MED12452 Effectively and Rapidly Restored Platelet Aggregation After Dosing to Ticagrelor Treated Mice, In Vivo The speed of onset and the extent of TICA0212/MEDI2452 mediated reversal of ticagrelor mediated inhibition of ADP-induced platelet aggregation in whole blood (impedance aggregometry) was determined ex vivo after intravenous (i.v.) dosing of ticagrelor in mice. Mice were given ticagrelor i.v. as a bolus of 1200 μg/kg. over 5 minutes, followed by a 15 min continuous infusion of 30 μg/kg/min. After termination of the ticagrelor infusion, when ticagrelor plasma exposure was measured to be in average 1.4 μM, mice were given an i.v. bolus of 250 mg/kg TICA0212/MEDI2452. At 5, 30, and 60 min post TICA0212/MEDI2452 administration mice were sacrificed and blood samples were collected. In this study the ADP-induced aggregation response was measured for 6 min and data expressed as the mean area under the curve of aggregation unit (AU) recorded over time (AU*min).

In carrying out the impedance aggregometry assay, mice were sacrificed and blood samples were collected into 7 μM hirudin. Blood (175 μL) was added to pre-heated $NaCl_2$ (37° C., 175 μL) in the Multiplate mini test cells and mixed for 3 min before addition of ADP, 12 μL, to a final concentration of 6.5 μM. The disposable Multiplate mini test cells contain a stir bar and have two separate pair of electrodes that are immersed into the blood sample.

When agonist (ADP) is added and shear is induced by stirring, platelets will start to adhere and aggregate onto the electrodes. This results in increased impedance over the electrodes, which is recorded continuously over time by the Multiplate impedance aggregometer (DynaByte, Munchen, Germany)

Figure 9:
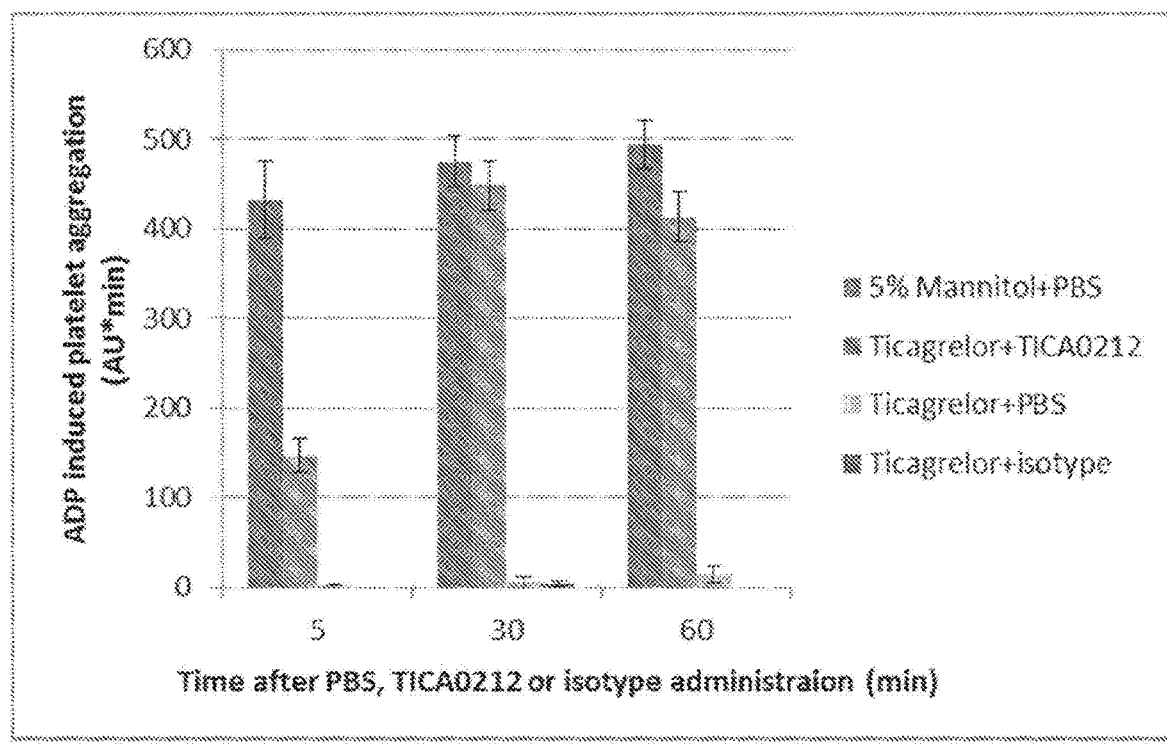
FIG. 9 shows the results of TICA0212, 250mg/kg, mediated reversal of ADP-induced whole blood aggregation ex vivo after dosing to ticagrelor treated mice.
Figure 11A:
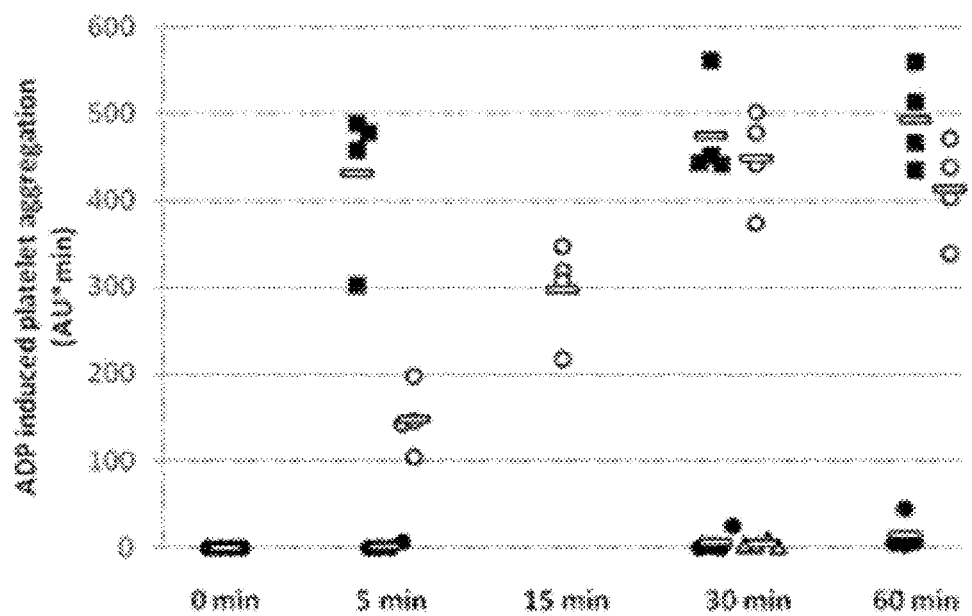
FIG. 11A-B shows reversal of ADP-induced whole blood aggregation ex vivo.
Figure 11B:
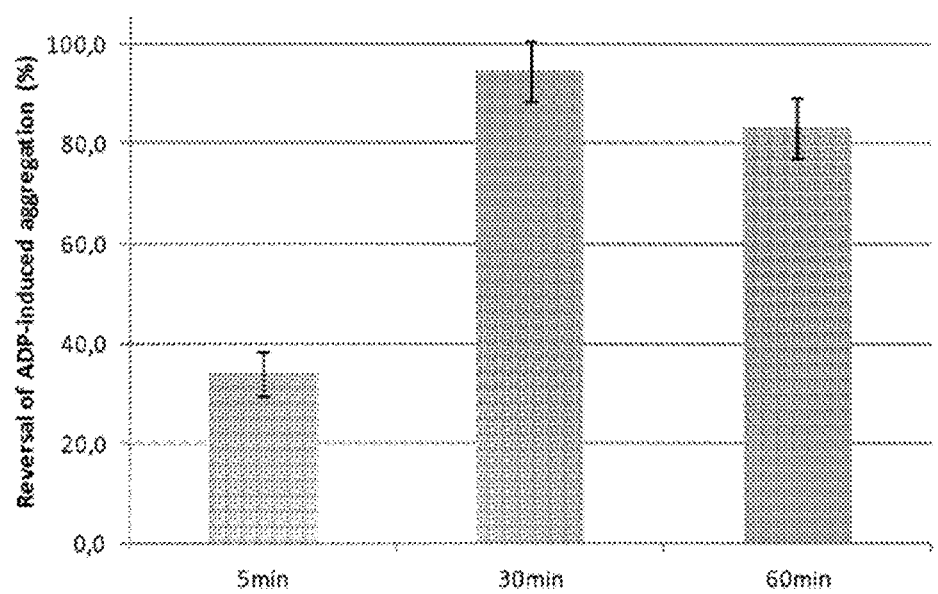

Ticagrelor treatment induced nearly complete inhibition of ADP-induced aggregation as the mean (n=4) aggregation response was reduced from 432 to 2, from 474 to 6 and from 494 to 14 AU*min at 5, 30, and 60 min after ticagrelor infusion and PBS bolus, respectively (FIG. 9). TICA0212/MEDI2452 mediated reversal of in vivo ticagrelor mediated inhibition as the mean (n=4) aggregation response increased from 2 to 147, from 6 to 448 and from 14 to 413 AU*min at 5, 30, and 60 minutes after ticagrelor infusion and TICA0212 bolus, respectively (FIG. 9). No reversal was present 30 minutes post administration of the isotype control as the mean (n=4) aggregation response remained unchanged from 6 to 4 AU*min.

This data shows that TICA0212/MEDI2452 can restore rapidly and effectively ADP-induced platelet aggregation when given as an i.v. bolus to mice dosed to a ticagrelor plasma concentration of 1.4 μM that provided complete inhibition of ADP-induced aggregation.

Example 12: Mouse Bleeding in Ticagrelor-Treated Mice

As one of the intended indications for TICA0212/MEDI2452 is as an antidote for ticagrelor patients requiring urgent surgery, TICA0212/MEDI2452 was evaluated in a mouse bleeding experiment designed to mimic the clinical setting were complete reversal should be achieved before initiation of surgery.

Mice were pre-treated with a continuous infusion of ticagrelor, 300 μg/kg/min or vehicle for 20 minutes. After stop of infusion, t=0, a bolus dose of TICA0212/MEDI2452 (600 mg/kg) or vehicle (histidine sucrose buffer) was given over 45 seconds and at t=30 minutes bleeding was induced by cutting 5mm from the tip of the tail. The tip of the tail was rinsed with water (2 mL/min) and the blood and water mixture was collected in a small chamber, where a stirrer mixed the fluid to enhance haemolysis and establish a homogeneous solution. Light transmission, at 525 nm, was recorded for 30 minutes when terminal blood samples were collected from the abdominal aorta for platelet aggregation. Light transmittance was transformed to absorbance and used to calculate blood loss as area under the absorbance curve (AUC, absorbance*s) and total bleeding time (BT, s) by plotting absorbance over time. All transmittance below 95% was defined as bleeding. Samples for platelet aggregation and total and free plasma exposure were also collected at end of ticagrelor infusion (t=0) and at time of tail cut (t=30 minutes).

Studies were approved by the ethical committee for animal research at the University of Göteborg, Sweden. Mice were anaesthetised with isofluran gas (Forenc®, Abbot Scandinavia AB, Sweden). A catheter was inserted in the left jugular vein for administration of vehicle or drug. The body temperature was maintained at 38° C. by external heating.

Figure 12A:
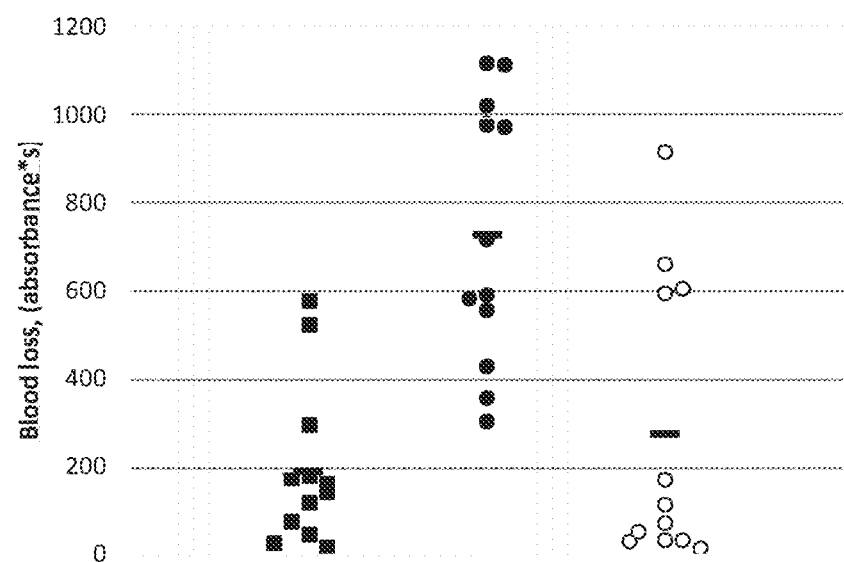
FIG. 12A-B shows the reversal of ticagrelor induced bleeding.
Figure 12B:
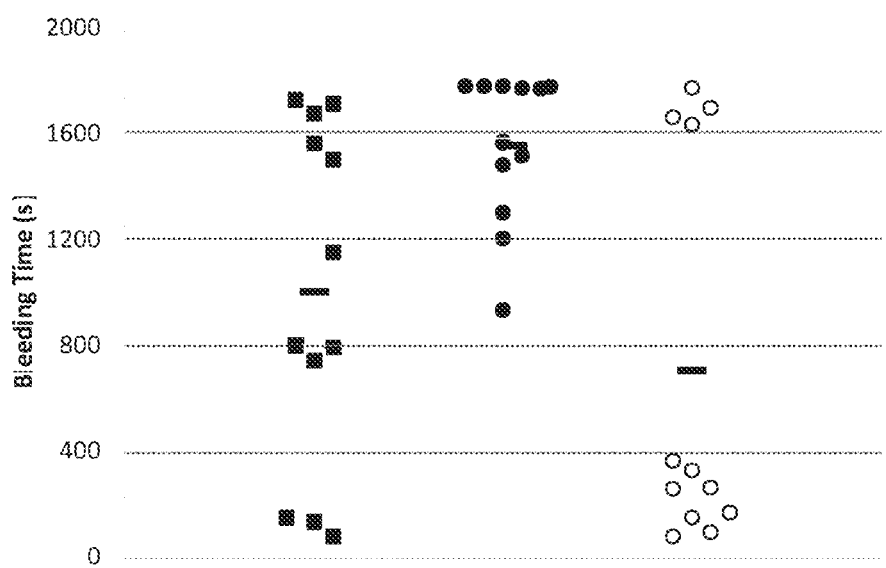

To translate the effect of TICA0212/MEDI2452 on platelet aggregation to a potential effect on bleeding, a prophylactic mouse tail bleeding study was performed. Ticagrelor was infused to a mean total ticagrelor and TAM plasma concentration of 7.6 and 0.3 µM, respectively, to provide a significant drug-dependant bleeding window. Immediately after stopping the ticagrelor infusion TICA0212/MEDI2452 was dosed as a single bolus of 600 mg/kg over 30 seconds. After 30 minutes, ADP-induced aggregation was fully normalized and the mean free plasma concentration of ticagrelor was reduced from 4.7 nM to below 0.03 nM (lower limit of quantification). Bleeding was initiated by a tail cut and monitored for 30 minutes. In vehicle treated mice the mean total ticagrelor and TAM plasma concentration at time of tail cut were 2.4 and 0.6 µM. The total blood loss and bleeding time over 30 minutes was significantly ($p<0.05$) enhanced by ticagrelor by about 3.8-fold and 1.6-fold, respectively. TICA0212/MEDI2452 significantly ($p<0.05$) reversed blood loss and bleeding time relative ticagrelor alone and back to a level not significantly different from mice not treated with ticagrelor (FIG. 12A-B). In this prophylactic setting TICA0212/MEDI2452 normalized ticagrelor dependent bleeding. The onset time of 30 minutes translated from the ex vivo model to this in vivo model demonstrating TICA0212/MEDI2452 can normalise both blood loss and bleeding time to that of mice not treated with ticagrelor.

Example 13: Total Plasma Concentration of Ticagrelor and TAM

Blood samples were collected in tubes with EDTA anticoagulant and centrifuged for 5 min at 10000× g at room temperature to prepare plasma. The plasma concentration of ticagrelor and TAM were determined by protein precipitation and liquid chromatography with tandem mass spectrometry (LC-MS/MS) as described in published method [Sillén H., et al., J Chromatogr B Analyt Technol Biomed Life Sci 2010; 878: 2299-306] with the following deviations. Plasma, 50 µL, was protein precipitated with 180 µl internal standard (D7-ZD6140) in acetonitrile. The liquid chromatographic system and mass spectrometer was an Acquity Ultra Performance LC coupled to a Xevo TQ-S mass spectrometer from Waters. Chromatographic separation was achieved on an Aquity UPLC® BEH C18 column (2.1×50 mm, particle size 1.7 um). Negative electrospray ionization was utilized. Eluent A was water with 10 mmol/L ammonium acetate, pH5 and eluent B was acetonitrile with 10 mmol/L ammonium acetate. Injection volume was 1 to 5 µL and the analytical gradient started with 4% B, increasing to 95% in 1.5 min, remaining until 2.3 min, before returning to initial conditions within 2.4 min followed by 0.3 min re-equilibration. No quality control samples were used in the analysis. The lower limit of quantification (LLOQ) was 0.005 µmol/L and the calibration range was 0.005 to 15.0 µM.

The total plasma concentrations of ticagrelor and TAM in presence of TICA0212/MEDI2452 were determined by adding 1% formic acid (FA: Sample, 1:5) followed by protein precipitation and LC-MS/MS as described above. Formic acid was added to the sample to facilitate dissociation of ticagrelor and TICA0212/MEDI2452.

Example 14: Ticagrelor Free Plasma Concentration

The method was optimized based on a previous published method [Sillen H., et al., J Chromatogr B Analyt Technol Biomed Life Sci. 2011 Aug. 1; 879(23): 2315-22]. Dialysis membranes (Spectrum Laboratories, Inc) which allows molecules with a mass below 6 to 8 kDa to pass through, was soaked in ELGA water for 10 to 15 min and placed between the dialysis plate halves (in house made). Plasma, 130 µL, was added to one side of the dialysis plate and 130 µL phosphate buffer, pH 7.0, was added to the opposite side. The wells on both sides were sealed with lids and aluminum plates were put on top on each side of the plate to avoid leakage. The plate was then placed vertical on an orbital shaker at 100 rpm/min at 37° C. for 24 h. The dialysis was terminated by transferring of 50 µL retentate from plasma side and 75 µL dialysate from buffer side to a protein LoBind PCR clean 96 deep-well plate containing 150 µL respective 75 µL internal standard (D7-ZD6140) in acetonitrile. The plate was mixed for 1 min and then centrifuged for 20 min, 1500× g at 4° C. After centrifugation 50 µL supernatant from the precipitated retentate was transferred and diluted with 50 µL ELGA H$_2$O before LC-MS/MS (Acquity Ultra Performance LC coupled to a Xevo TQ-S mass spectrometer, Waters) analysis. No quality control samples were used in the analysis. Calibration range for retentate was 0.4 to 1000 nmol/L and for dialysate 0.003 to 50 nmol/L. The LLOQ for ticagrelor in dialysate was 0.03 nmol/L.

Table 9 below provides an overview of the exemplary antibodies described in the above Examples and used to illustrate certain embodiments of the technology disclosed herein.

TABLE 9

Summary of Antibody/scFv/Fab Sequences

| Antibody Ref Sequence | Sequence |
|---|---|
| TICA0010 V$_H$ DNA (SEQ ID NO: 1) | GAGGTGCAGC TGTTGGAGTC TGGGGGAGGC TTGGTACAGC CTGGGGGGTC CCTGAGACTC TCCTGTGCAG CCTCTGGATT CACCTTTAGC AGCTATGCCA TGAGCTGGGT CCGCCAGGCT CCAGGGAAGG GGCTGGAGTG GGTCTCAGCT ATTAGTGGTA GTGGTGGTAG CACATACTAC GCAGACTCCG TGAAGGGCCG GTTCACCATC TCCAGAGACA ATTCCAAGAA CACGCTGTAT CTGCAAATGA ACAGCCTGAG AGCCGAGGAC ACGGCCGTGT ATTACTGTGC AACAGAGTAC GACCTGCAAC GGCCTTTCGG GTTTGACTTC TGGGGCAAGG GGACAATGGT CACCGTCTCG AGT |

TABLE 9-continued

Summary of Antibody/scFv/Fab Sequences

| Antibody Ref Sequence | Sequence |
|---|---|
| TICA0010 V$_H$ (SEQ ID NO: 2) | EVQLLESGGGLVQPGGSLRLSCAASGFTFSSYAMSWVRQAPGKGLEWVSAI SGSGGSTYYADSVKGRFTISRDNSKNTLYLQMNSLRAEDTAVYYCATEYDL QRPFGFDFWGKGTMVTVSS |
| TICA0010 V$_H$ CDR1 (SEQ ID NO: 3) | SYAMS |
| TICA0010 V$_H$ CDR2 (SEQ ID NO: 4) | AISGSGGSTYYADSVKG |
| TICA0010 V$_H$ CDR3 (SEQ ID NO: 5) | EYDLQRPFGFDF |
| TICA0010 V$_L$ DNA (SEQ ID NO: 6) | TCCTATGTGC TGACTCAGCC ACCCTCAGCG TCTGGGGCCC CCGGGCAGAG GGCTACCATC TCCTGCTCTG GAAGCAGCTC CAACATCGGA AGTAATCTTG TGAACTGGTA CCAACAATTC CCAGGAGAGG CCCCCAAGCT CCTCATCTTT AGTGACAATC AACGACCCTC AGGGGTCCCT GACCGATTCT CTGGCTCCAG GTCTGGCACC TCAGCCTCCC TGGCCATCAG TGGGCTCCAG TCCGAGGATG AGGCTGATTA TTACTGTGCA ACGTGGGATG ACAGACTGGA TGGTTATGTG GTATTCGGCG GAGGGACCAA GCTGACCGTC CTA |
| TICA0010 V$_L$ (SEQ ID NO: 7) | SYVLTQFPSASGAPGQRATISCSGSSSNIGSNLVNWYQQFPGEAPKLLIFS DNQRPSGVPDRFSGSRSGTSASLAISGLQSEDEADYYCATWDDRLDGYVVF GGGTKLTVL |
| TICA0010 V$_L$ CDR1 (SEQ ID NO: 8) | SGSSSNIGSNLVN |
| TICA0010 V$_L$ CDR2 (SEQ ID NO: 9) | SDNQRPS |
| TICA0010 V$_L$ CDR3 (SEQ ID NO: 10) | ATWDDRLDGYVV |
| TICA0049 V$_H$ DNA (SEQ ID NO: 11) | CAGGTACAGC TGCAGCAGTC AGGGGCTGAG GTGAAGAAGC CTGGGGCCTC AGTGAAGGTT TCCTGCAAGG CTTCTGGATA CACCTTCATT ACCTATGGTA TTCACTGGGT GCGCCAGGCC CCCGGACAAG GGCTTGAGTG GATGGGATGG ATCGACCCCG GGCATGGTTA CACAAAATAT TCACAGAAGT TCCAGGGCAG AGTCACCATT ACCAGGGACA CATCCGCGAG CACAGCCTAC ATGGAGATGA GCAGCCTCAG ATCTGAAGAC ACGGCTGTGT ATTACTGTGC GAGAGCGGAC CTGGGTGACT ACTGGGGCCG GGGAACCCTG GTCACCGTCT CGAGT |
| TICA0049 V$_H$ (SEQ ID NO: 12) | QVQLQQSGAEVKKPGASVKVSCKASGYTFITYGIHWVRQAPGQGLEWMGWI DPGHGYTKYSQKFQGRVTITRDTSASTAYMEMSSLRSEDTAVYYCARADLG DYWGRGTLVTVSS |
| TICA0049 V$_H$ CDR1 (SEQ ID NO: 13) | TYGIH |
| TICA0049 V$_H$ CDR2 (SEQ ID NO: 14) | WIDPGHGYTKYSQKFQG |
| TICA0049 V$_H$ CDR3 (SEQ ID NO: 15) | ADLGDY |
| TICA0049 V$_L$ DNA (SEQ ID NO: 16) | CAGTCTGTCG TGACGCAGCC GCCCTCAGTG TCTGCGGCCC CAGGACAGAA GGTCACCATC TCCTGCTCTG GAAGCAGCTC CAACATTGGG AAGAATTATG TTTCCTGGTT CCAGCAGCTC CCAGGTACAG CCCCCAAACT CCTCATTTAT GACAATCATA AGCGACCCTC AGGGATTCCT GACCGATTCT CTGCCTCCAA GTCTGGCACG TCAGCCACCC TGGTCATCTC CGGTCTCCAG ACTGGGGACG AGGCCCATTA TTACTGCGGA ACATGGGATA CCAGACTGAG TGCTGGGGTG TTCGGCGGAG GGACCAAGGT CACCGTCCTA |
| TICA0049 V$_L$ (SEQ ID NO: 17) | QSVVTQPPSVSAAPGQKVTISCSGSSSNIGKNYVSWFQQLPGTAPKLLIYD NHKRPSGIPDRFSASKSGTSATLVISGLQTGDEAHYYCGTWDTRLSAGVFG GGTKVTVL |
| TICA0049 V$_L$ CDR1 (SEQ ID NO: 18) | SGSSSNIGKNYVS |

TABLE 9-continued

Summary of Antibody/scFv/Fab Sequences

| Antibody Ref Sequence | Sequence |
|---|---|
| TICA0049 $V_L$ CDR2 (SEQ ID NO: 19) | DNHKRPS |
| TICA0049 $V_L$ CDR3 (SEQ ID NO: 20) | GTWDTRLSAGV |
| TICA0053 $V_H$ DNA (SEQ ID NO: 21) | GAGGTGCAGC TGTTGGAGTC TGGGGGAGGC TTGGTACAGC CTGGGGGGTC CCTGAGACTC TCCTGTGCAG CCTCTGGATT CACCTTTAGC AGCTATGCCA TGAGCTGGGT CCGCCAGGCT CCAGGGAAGG GGCTGGAGTG GGTCTCAGCT ATTAGTGGTA GTGGTGGTAG CACATACTAC GCAGACTCCG TGAAGGGCCG GTTCACCATC TCCAGAGACA ATTCCAAGAA CACGCTGTAT CTGCAAATGA ACAGCCTGAG AGCCGAGGAC ACGGCCGTGT ATTACTGTGG CCATGATAGT AGTGGTTACT CCTACTCCTT TGACTTCTGG GGGCGGGGGA CCACGGTCAC CGTCTCGAGT |
| TICA0053 $V_H$ (SEQ ID NO: 22) | EVQLLESGGGLVQPGSSLRLSCAASGFTFSSYAMSWVRQAPGKGLEWVSAI SGSGGSTYYADSVKGRFTISRDNSKNTLYLQMNSLRAEDTAVYYCGHDSSG YSYSFDFWGRGTTVTVSS |
| TICA0053 $V_H$ CDR1 (SEQ ID NO: 23) | SYAMS |
| TICA0053 $V_H$ CDR2 (SEQ ID NO: 24) | AISGSGGSTYYADSVKG |
| TICA0053 $V_H$ CDR3 (SEQ ID NO: 25) | DSSGYGYSFDF |
| TICA0053 $V_L$ DNA (SEQ ID NO: 26) | CAGTCTGTGT TGACGCAGCC GCCCTCAGCG TCTGGGACCC CCGGGCAGAG GGTCACCATC TCTTGTTCTG GCAACATCTC CAACATCGGA AGTAACACTG TCAACTGGTA TCAACACGTC CCAGGAGCGG CCCCCAGACT CCTCATCTAT GTTAATGATC AGCGGCCGTC AGGGGTCCCT GACCGATTCT CTGGCTCCAA GTCTGGCACC TCAGCCTCCC TGGCCATCAG TGGGCTCCAG TCTGAAGATG AGGCTGATTA TTACTGTGCA ACGTGGGATG ACACCCTGAA TGGAGGGGTC TTCGGCGGAG GGACCAAGCT GACCGTCCTA |
| TICA0053 $V_L$ (SEQ ID NO: 27) | QSVLTQPPSASGTPGQRVTISCSGNISNIGSNTVNWYQHVPGAAPRLLIYV NDQRPSGVPDRFSGSKSGTSASLAISGLQSEDEADYYCATWDDTLNGGVFG GGTKLTVL |
| TICA0053 $V_L$ CDR1 (SEQ ID NO: 28) | SGNISNIGSNTVN |
| TICA0053 $V_L$ CDR2 (SEQ ID NO: 29) | VNDQRPS |
| TICA0053 $V_L$ CDR3 (SEQ ID NO: 30) | ATWDDTLNGGV |
| TICA0072 $V_H$ DNA (SEQ ID NO: 31) | CAGGTGCAGC TGCAGGAGTC CGGGGCTGAG GTGAAGAAGC CTGGGTCCTC GGTGAGGGTC TCCTGCAAGG CTTCTGGAGG CACCTTCGAC AGTTATAGTA TCCATTGGGT GCGCCAGGCC CCTGGACAAG GGCTTGAGTG GATGGGAGGG ATCATCCCTG CCTTTGGGAC ATTAAGCAGC GCACAGGACT TCCAGGCCAG AGTCACCATT AGCGCGGACA AGTCCACGAG CACAGCCTAT ATGGAGCTGA GCGGCCTGAG ATCTGAGGAC ACGGCCGTAT ATTACTGTGC GAGAGGGTCC CATCTTTACG ATTTTTGGAG TGCTTCTCAT CCCCCCAATG ATGCTCTTGC TATTTGGGGC CAAGGAACCC TGGTCACCGT CTCGAGT |
| TICA0072 $V_H$ (SEQ ID NO: 32) | QVQLQESGAEVKKPGSSVRVSCKASGGTFDSYSIHWVRQAPGQGLEWMGGI IPAFGTLSSAQDFQARVTISADKSTSTAYMELSGLRSEDTAVYYCARGSHL YDFWSASHPPNDALAIWGQGTLVTVSS |
| TICA0072 $V_H$ CDR1 (SEQ ID NO: 33) | SYSIH |
| TICA0072 $V_H$ CDR2 (SEQ ID NO: 34) | GIIPAFGTLSSAQDFQA |
| TICA0072 $V_H$ CDR3 (SEQ ID NO: 35) | GSHLYDFWSASHPPNDALAI |

TABLE 9-continued

Summary of Antibody/scFv/Fab Sequences

| Antibody Ref Sequence | Sequence |
|---|---|
| TICA0072 $V_L$ DNA (SEQ ID NO: 36) | CAGTCTGTCG TGACGCAGCC GCCCTCAGTG TCTGCGGCCC CAGGACAGAA GGTCACCATC TCCTGCTCTG GAAGCAACTC CGACATTGGC AACAATTATG TGTCGTGGTA CCAACAGCTC CCAGGAACAG CCCCCAAACT CCTCATTTAT GACAATAATA AACGACCCTC AGGGATTCCT GACCGATTCT CTGGCTCCAA GTCTGGCACG TCAGCCACCC TGGCCATCAC CGGACTCCAG GCTGGGGACG AGGCCGATTA TTACTGCGGG ACATGGGATA TCAGCCTGAG CGCTGGCTTG TTCGGCGGAG GGACCAAGGT CACCGTCCTA |
| TICA0072 $V_L$ (SEQ ID NO: 37) | QSVVTQPPSVSAAPGQKVTISC<u>SGSNSDIGNNYVS</u>WYQQLPGTAPKLLIY<u>D</u><u>NNKRPS</u>GIPDRFSGSKSGTSATLAITGLQAGDEADYYC<u>GTWDISLSAGL</u>FG GGTKVTVL |
| TICA0072 $V_L$ CDR1 (SEQ ID NO: 38) | SGSNSDIGNNYVS |
| TICA0072 $V_L$ CDR2 (SEQ ID NO: 39) | DNNKRPS |
| TICA0072 $V_L$ CDR3 (SEQ ID NO: 40) | GTWDISLSAGL |
| TICA0159 $V_H$ DNA (SEQ ID NO: 41) | CAGGTGCAGC TGCAGGAGTC CGGGGCTGAG GTGAAGAAGC CTGGGTCCTC GGTGAGGGTC TCCTGCAAGG CTTCTGGAGG CACCTTCGAC AGTTATAGTA TCCATTGGGT GCGCCAGGCC CCTGGACAAG GGCTTGAGTG GATGGGAGGG ATCATCCCTG CCTTTGGGAC ATTAAGCAGC GCACAGGACT TCCAGGCCAG AGTCACCATT AGCGCGGACA AGTCCACGAG CACAGCCTAT ATGGAGCTGA GCGGCCTGAG ATCTGAGGAC ACCGCCGTAT ATTACTGTGC GAGAGGGAGC TTCGACTACA GGTTTTGGAG TGCTTCTCAT CCCCCCAATG ATGCTCTTGC TATTTGGGGC CAAGGAACCC TGGTCACCGT CTCGAGT |
| TICA0159 $V_H$ (SEQ ID NO: 42) | QVQLQESGAEVKKPGSSVRVSCKASGGTFD<u>SYSIH</u>WVRQAPGQGLEWMGG<u>I</u><u>IPAFGTLSSAQDFQA</u>RVTISADKSTSTAYMELSGLRSEDTAVYYCAR<u>GSFD</u><u>YRFWSASHPPNDALAI</u>WGQGTLVTVSS |
| TICA0159 $V_H$ CDR1 (SEQ ID NO: 43) | SYSIH |
| TICA0159 $V_H$ CDR2 (SEQ ID NO: 44) | GIIPAFGTLSSAQDFQA |
| TICA0159 $V_H$ CDR3 (SEQ ID NO: 45) | GSFDYRFWSASHPPNDALAI |
| TICA0159 $V_L$ DNA (SEQ ID NO: 46) | CAGTCTGTCG TGACGCAGCC GCCCTCAGTG TCTGCGGCCC CAGGACAGAA GGTCACCATC TCCTGCTCTG GAAGCAACTC CGACATTGGC AACAATTATG TGTCGTGGTA CCAACAGCTC CCAGGAACAG CCCCCAAACT CCTCATTTAT GACAATAATA AACGACCCTC AGGGATTCCT GACCGATTCT CTGGCTCCAA GTCTGGCACG TCAGCCACCC TGGCCATCAC CGGACTCCAG GCTGGGGACG AGGCCGATTA TTACTGCGGG ACATGGGATA TCAGCCTGAG CGCTGGCTTG TTCGGCGGAG GGACCAAGGT CACCGTCCTA |
| TICA0159 $V_L$ (SEQ ID NO: 47) | QSVVTQPPSVSAAPGQKVTISC<u>SGSNSDIGNNYVS</u>WYQQLPGTAPKLLIY<u>D</u><u>NNKRPS</u>GIPDRFSGSKSGTSATLAITGLQAGDEADYYC<u>GTWDISLSAGL</u>FG GGTKVTVL |
| TICA0159 $V_L$ CDR1 (SEQ ID NO: 48) | SGSNSDIGNNYVS |
| TICA0159 $V_L$ CDR2 (SEQ ID NO: 49) | DNNKRPS |
| TICA0159 $V_L$ CDR3 (SEQ ID NO: 50) | GTWDISLSAGL |
| TICA0162 $V_H$ DNA (SEQ ID NO: 51) | CAGGTGCAGC TGCAGGAGTC CGGGGCTGAG GTGAAGAAGC CTGGGTCCTC GGTGAGGGTC TCCTGCAAGG CTTCTGGAGG CACCTTCGAC AGTTATAGTA TCCATTGGGT GCGCCAGGCC CCTGGACAAG GGCTTGAGTG GATGGGAGGG ATCATCCCTG CCTTTGGGAC ATTAAGCAGC GCACAGGACT TCCAGGCCAG |

TABLE 9-continued

Summary of Antibody/scFv/Fab Sequences

| Antibody Ref Sequence | Sequence |
|---|---|
| | AGTCACCATT AGCGCGGACA AGTCCACGAG CACAGCCTAT<br>ATGGAGCTGA GCGGCCTGAG ATCTGAGGAC ACGGCCGTAT<br>ATTACTGTGC GAGAGGCTCC TTCGACTACT ACTTTTGGAG<br>TGCTTCTCAT CCCCCCAATG ATGCTCTTGC TATTTGGGGC<br>CAAGGAACCC TGGTCACCGT CTCGAGT |
| TICA0162 $V_H$<br>(SEQ ID NO: 52) | QVQLQESGAEVKKPGSSVRVSCKASGGTFDSYSIHWVRQAPGQGLEWMGGI<br>IPAFGTLSSAQDFQARVTISADKSTSTAYMELSGLRSEDTAVYYCARGSFD<br>YYFWSASHPPNDALAIWGQGTLVTVSS |
| TICA0162 $V_H$ CDR1<br>(SEQ ID NO: 53) | SYSIH |
| TICA0162 $V_H$ CDR2<br>(SEQ ID NO: 54) | GIIPAFGTLSSAQDFQA |
| TICA0162 $V_H$ CDR3<br>(SEQ ID NO: 55) | GSFDYYFWSASHPPNDALAI |
| TICA0162 $V_L$ DNA<br>(SEQ ID NO: 56) | CAGTCTGTCG TGACGCAGCC GCCCTCAGTG TCTGCGGCCC<br>CAGGACAGAA GGTCACCATC TCCTGCTCTG GAAGCAACTC<br>CGACATTGGC AACAATTATG TGTCGTGGTA CCAACAGCTC<br>CCAGGAACAG CCCCCAAACT CCTCATTTAT GACAATAATA<br>AACGACCCTC AGGGATTCCT GACCGATTCT CTGGCTCCAA<br>GTCTGGCACG TCAGCCACCC TGGCCATCAC CGGACTCCAG<br>GCTGGGGACG AGGCCGATTA TTACTGCGGG ACATGGGATA<br>TCAGCCTGAG CGCTGGCTTG TTCGGCGGAG GGACCAAGGT<br>CACCGTCCTA |
| TICA0162 $V_L$<br>(SEQ ID NO: 57) | QSVVTQPPSVSAAPGQKVTISCSGSNSDIGNNYVSWYQQLPGTAPKLLIYD<br>NNKRPSGIPDRFSGSKSGTSATLAITGLQAGDEADYYCGTWDISLSAGLFG<br>GGTKVTVL |
| TICA0162 $V_L$ CDR1<br>(SEQ ID NO: 58) | SGSNSDIGNNYVS |
| TICA0162 $V_L$ CDR2<br>(SEQ ID NO: 59) | DNNKRPS |
| TICA0162 $V_L$ CDR3<br>(SEQ ID NO: 60) | GTWDISLSAGL |
| TICA0152 $V_H$ DNA<br>(SEQ ID NO: 61) | CAGGTGCAGC TGCAGGAGTC CGGGGCTGAG GTGAAGAAGC<br>CTGGGTCCTC GGTGAGGGTC TCCTGCAAGG CTTCTGGAGG<br>CACCTTCGAC AGTTATAGTA TCCATTGGGT GCGCCAGGCC<br>CCTGGACAAG GGCTTGAGTG GATGGGAGGG ATCATCCCTG<br>CCTTTGGGAC ATTAAGCAGC GCACAGGACT TCCAGGCCAG<br>AGTCACCATT AGCGCGGACA AGTCCACGAG CACAGCCTAT<br>ATGGAGCTGA GCGGCCTGAG ATCTGAGGAC ACGGCCGTAT<br>ATTACTGTGC GAGAGGGTCC CATCTTTACG ATTTTTGGAG<br>TGCTTCTCAT CCCCCCAATG ATGCTCTTGC TATTTGGGGC<br>CAAGGAACCC TGGTCACCGT CTCGAGT |
| TICA0152 $V_H$<br>(SEQ ID NO: 62) | QVQLQESGAEVKKPGSSVRVSCKASGGTFDSYSIHWVRQAPGQGLEWMGGI<br>IPAFGTLSSAQDFQARVTISADKSTSTAYMELSGLRSEDTAVYYCARGSHL<br>YDFWSASHPPNDALAIWGQGTLVTVSS |
| TICA0152 $V_H$ CDR1<br>(SEQ ID NO: 63) | SYSIH |
| TICA0152 $V_H$ CDR2<br>(SEQ ID NO: 64) | GIIPAFGTLSSAQDFQA |
| TICA0152 $V_H$ CDR3<br>(SEQ ID NO: 65) | GSHLYDFWSASHPPNDALAI |
| TICA0152 $V_L$ DNA<br>(SEQ ID NO: 66) | CAGTCTGTCG TGACGCAGCC GCCCTCAGTG TCTGCGGCCC<br>CAGGACAGAA GGTCACCATC TCCTGCTCTG GAAGCAACTC<br>CGACATTGGC AACAATTATG TGTCGTGGTA CCAACAGCTC<br>CCAGGAACAG CCCCCAAACT CCTCATTTAT GACAATAATA<br>AACGACCCTC AGGGATTCCT GACCGATTCT CTGGCTCCAA<br>GTCTGGCACG TCAGCCACCC TGGCCATCAC CGGACTCCAG<br>GCTGGGGACG AGGCCGATTA TTACTGCGGG ACATGGCTGT<br>ACGACCGGGC CGTCGGCTTG TTCGGCGGAG GGACCAAGGT<br>CACCGTCCTA |

TABLE 9-continued

Summary of Antibody/scFv/Fab Sequences

| Antibody Ref Sequence | Sequence |
|---|---|
| TICA0152 V<sub>L</sub><br>(SEQ ID NO: 67) | QSVVTQPPSVSAAPGQKVTISC<u>SGSNSDIGNNYVS</u>WYQQLPGTAPKLLIY<u>D</u><br><u>NNKRPS</u>GIPDRFSGSKSGTSATLAITGLQAGDEADYYC<u>GTWLYDRAVGL</u>FG<br>GGTKVTVL |
| TICA0152 V<sub>L</sub> CDR1<br>(SEQ ID NO: 68) | SGSNSDIGNNYVS |
| TICA0152 V<sub>L</sub> CDR2<br>(SEQ ID NO: 69) | DNNKRPS |
| TICA0152 V<sub>L</sub> CDR3<br>(SEQ ID NO: 70) | GTWLYDRAVGL |
| TICA0212/MEDI2452<br>V<sub>H</sub> DNA<br>(SEQ ID NO: 71) | CAGGTGCAGC TGCAGGAGTC CGGGGCTGAG GTGAAGAAGC<br>CTGGGTCCTC GGTGAGGGTC TCCTGCAAGG CTTCTGGAGG<br>CACCTTCGAC AGTTATAGTA TCCATTGGGT GCGCCAGGCC<br>CCTGGACAAG GCTTGAGTG GATGGGAGGG ATCATCCCTG<br>CCTTTGGGAC ATTAAGCAGC GCACAGGACT TCCAGGCCAG<br>AGTCACCATT AGCGCGGACA AGTCCACGAG CACAGCCTAT<br>ATGGAGCTGA GCGGCCTGAG ATCTGAGGAC ACGGCCGTAT<br>ATTACTGTGC GAGAGGCTCC TTCGACTACT ACTTTTGGAG<br>TGCTTCTCAT CCCCCCAATG ATGCTCTTGC TATTTGGGGC<br>CAAGGAACCC TGGTCACCGT CTCGAGT |
| TICA0212/MEDI2452<br>V<sub>H</sub><br>(SEQ ID NO: 72) | QVQLQESGAEVKKPGSSVRVSCKASGGTFD<u>SYSIH</u>WVRQAPGQGLEWMG<u>GI</u><br><u>IPAFGTLSSAQDFQA</u>RVTISADKSTSTAYMELSGLRSEDTAVYYCAR<u>GSFD</u><br><u>YYFWSASHPPNDALAI</u>WGQGTLVTVSS |
| TICA0212/MEDI2452<br>V<sub>H</sub> CDR1<br>(SEQ ID NO: 73) | SYSIH |
| TICA0212/MEDI2452<br>V<sub>H</sub> CDR2<br>(SEQ ID NO: 74) | GIIPAFGTLSSAQDFQA |
| TICA0212/MEDI2452<br>V<sub>H</sub> CDR3<br>(SEQ ID NO: 75) | GSFDYYFWSASHPPNDALAI |
| TICA0212/MEDI2452<br>V<sub>L</sub> DNA<br>(SEQ ID NO: 76) | CAGTCTGTCG TGACGCAGCC GCCCTCAGTG TCTGCGGCCC<br>CAGGACAGAA GGTCACCATC TCCTGCTCTG GAAGCAACTC<br>CGACATTGGC AACAATTATG TGTCGTGGTA CCAACAGCTC<br>CCAGGAACAG CCCCCAAACT CCTCATTTAT GACAATAATA<br>AACGACCCTC AGGGATTCCT GACCGATTCT CTGGCTCCAA<br>GTCTGGCACG TCAGCCACCC TGGCCATCAC CGGACTCCAG<br>GCTGGGGACG AGGCCGATTA TTACTGCGGG ACATGGCTGT<br>ACGACCGGGC CGTCGGCTTG TTCGGCGGAG GGACCAAGGT<br>CACCGTCCTA |
| TICA0212/MEDI2452<br>V<sub>L</sub><br>(SEQ ID NO: 77) | QSVVTQPPSVSAAPGQKVTISC<u>SGSNSDIGNNYVS</u>WYQQLPGTAPKLLIY<u>D</u><br><u>NNKRPS</u>GIPDRFSGSKSGTSATLAITGLQAGDEADYYC<u>GTWLYDRAVGL</u>FG<br>GGTKVTVL |
| TICA0212/MEDI2452<br>V<sub>L</sub> CDR1<br>(SEQ ID NO: 78) | SGSNSDIGNNYVS |
| TICA0212/MEDI2452<br>V<sub>L</sub> CDR2<br>(SEQ ID NO: 79) | DNNKRPS |
| TICA0212/MEDI2452<br>V<sub>L</sub> CDR3<br>(SEQ ID NO: 80) | GTWLYDRAVGL |

REFERENCES AND INCORPORATION BY REFERENCE

1. Van Giezen J J, Nilsson L, Berntsson P, et al. Ticagrelor binds to human P2Y(12) independently from ADP but antagonizes ADP-induced receptor signalling and platelet aggregation. *J Thromb Haemost.* 2009; 7(9): 1556-1565
2. Wallentin L, Becker R C, Budaj A, et al. Ticagrelor versus clopidogrel in patients with acute coronary syndromes. *N Engl J Med.* 2009; 361: 1045-1057.
3. Amsterdam E A, Wenger N K, Brindis R G, et al. 2014 ACC/AHA guideline for the management of patients with non-ST-elevation acute coronary syndromes: a report of the American College of Cardiology/American Heart Association Task Force on Practice Guidelines. *Circulation.* 2014; 000: 000-000
4. Storey R F, Angiolillo D J, Patil S B, et al. Inhibitory effects of ticagrelor compared with clopidogrel on platelet function in patients with acute coronary syndromes: the PLATO (PLATelet inhibition and patient Outcomes) PLATELET substudy. *J Am Coll Cardiol.* 2010; 56(18): 1456-1462.
5. Taylor G, Osinski D. Thevenin A, et al. Is platelet transfusion efficient to restore platelet reactivity in patients who are responders to aspirin and/or clopidogrel before emergency surgery? *J Trauma Acute Care Surg.* 2013; 74: 1367-1369.
6. Prüller F, Drexler C. Archan S. Macher S, Raggam R B. Mahla E. Low platelet reactivity is recovered by transfusion of stored platelets: a healthy volunteer in vivo study. *J Thromb Haemost.* 2011: 9(8): 1670-1673.
7. Hansson E C, Shams Hakimi C, Åström-Olsson K, et al. Effects of ex vivo platelet supplementation on platelet aggregability in blood samples from patients treated with acetylsalicylic acid, clopidogrel, or ticagrelor. *Br J Andesth.* 2014; 112(3): 570-575.
8. Thiele T. Sümnig A, Hron G. Platelet transfusion for reversal of dual antiplatelet therapy in patients requiring urgent surgery: a pilot study. *J Thromb Haemost.* 2012; 10: 968-971.
9. Pehrsson S, Hansson K, Nylander S. Ticagrelor-induced bleeding in mice can be reversed by FVIIa (NovoSeven®) and FII. *J Am Coll Cardiol.* 2013; 61(10S): E212.
10. Dolgin E. Antidotes edge closer to reversing effects of new blood thinners. *Nat Med.* 2013: 19(3): 251.
11. Crowther M A, Ageno W, Garcia D, et al. Oral vitamin K versus placebo to correct excessive anticoagulation in patients receiving warfarin: a randomized trial. *Ann Intern Med.* 2009; 150: 293-300.
12. Schiele F, van Ryn J, Canada K, et al. A specific antidote for dabigatran: functional and structural characterization. *Blood.* 2013; 121: 3554-3562.
13. Lu G, DeGuzman F R, Hollenbach S J, et al. A specific antidote for reversal of anticoagulation by direct and indirect inhibitors of coagulation factor Xa. *Nat Med.* 2013; 19: 446-451.
14. Storey R F, Husted S, Harrington R A, et al. Inhibition of platelet aggregation by AZD6140, a reversible oral $P2Y_{12}$ receptor antagonist, compared with clopidogrel in patients with acute coronary syndromes. *J Am Coll Cardiol.* 2007: 50: 1852-1856.
15. Husted S E, Storey R F, Bliden K, et al. Pharmacokinetics and pharmacodynamics of ticagrelor in patients with stable coronary artery disease: results from the ONSET-OFFSET and RESPOND studies. *Clin Pharmacokinet.* 2012; 51(6): 397-409.
16. Teng R. Oliver S, Hayes M A, Butler K. Absorption, distribution, metabolism, and excretion of ticagrelor in healthy subjects. *Drug Metab Dispos.* 2010: 38(9): 1514-1521.
17. Daramola O, Stevenson J, Dean G, et al. A high-yielding CHO transient system: coexpression of genes encoding EBNA-1 and GS enhances transient protein expression. *Biotechnol Prog.* 2014; 30(1): 132-141.
18. Oprea T I, Nielsen S K, Ursu O, et al. Associating Drugs, Targets and Clinical Outcomes into an Integrated Network Affords a New Platform for Computer-Aided Drug Repurposing. *Mol Inform.* 2011; 30: 100-111.
19. Springthorpe B, Bailey A, Barton P, et al. From ATP to AZD6140: the discovery of an orally active reversible $P2Y_{12}$ receptor antagonist for the prevention of thrombosis. *Bioorg Med Chem Lett.* 2007: 17: 6013-6018.
20. Fanning S W1, Horn J R. An anti-hapten camelid antibody reveals a cryptic binding site with significant energetic contributions from a nonhypervariable loop. *Protein Sci.* 2011; 20: 1196-1207.
21. Zhang K, Zhang J, Gao Z G, et al. Structure of the human $P2Y_{12}$ receptor in complex with an antithrombotic drug. *Nature.* 2014: 509: 115-118.
22. Cattaneo M, Schulz R, Nylander S. Adenosine-mediated effects of ticagrelor: evidence and potential clinical relevance. *J Am Coll Cardiol.* 2014; 63: 2503-2509.
23. Sillén H, Cook M, Davis P. Determination of unbound ticagrelor and its active metabolite (AR-C124910XX) in human plasma by equilibrium dialysis and LC-MS/MS. *J Chromatogr B Analyt Technol Biomed Life Sci.* 2011; 879 (23): 2315-2322.

All publications and patents mentioned herein are hereby incorporated by reference in their entirety as if each individual publication or patent was specifically and individually indicated to be incorporated by reference.

While specific aspects of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. Nucleic acid encoding an antibody or a fragment thereof comprising complementarity-determining region (CDR) combinations selected from the group consisting of:
   SEQ ID NO:53 (VH CDR1), SEQ ID NO:54 (VH CDR2), SEQ ID NO:55 (VH CDR3), SEQ ID NO:58 (VL CDR1), SEQ ID NO:59 (VL CDR2), and SEQ ID NO:60 (VL CDR3);
   SEQ ID NO:63 (VH CDR1), SEQ ID NO:64 (VH CDR2), SEQ ID NO:65 (VH CDR3), SEQ ID NO:68 (VL CDR1), SEQ ID NO:69 (VL CDR2), and SEQ ID NO:70 (VL CDR3); and
   SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3);
   wherein the antibody or fragment thereof binds to ticagrelor ((1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclopentane-1,2-diol) or a metabolite or derivative thereof.

2. The nucleic acid of claim 1, wherein the antibody or fragment thereof comprises CDRs comprising: SEQ ID NO:73 (VH CDR1), SEQ ID NO:74 (VH CDR2), SEQ ID NO: 75 (VH CDR3), SEQ ID NO:78 (VL CDR1), SEQ ID NO:79 (VL CDR2), and SEQ ID NO: 80 (VL CDR3).

3. The nucleic acid of claim 1, wherein the antibody or fragment thereof comprises a variable heavy chain (VH) region and a variable light chain (VL) region, wherein:
   the VH has an amino acid sequence according to SEQ ID NO: 52 and the VL has an amino acid sequence according to SEQ ID NO: 57; or
   the VH has an amino acid sequence according to SEQ ID NO: 62 and the VL has an amino acid sequence according to SEQ ID NO: 67; or
   the VH has an amino acid sequence according to SEQ ID NO: 72 and the VL has an amino acid sequence according to SEQ ID NO: 77.

4. The nucleic acid of claim 1, wherein the antibody or fragment thereof comprises a VH region and a VL region, wherein the VH has an amino acid sequence according to SEQ ID NO: 72 and the VL has an amino acid sequence according to SEQ ID NO: 77.

5. The nucleic acid of claim 2, wherein the antibody or fragment thereof comprises a VH region and a VL region, wherein the VH has an amino acid sequence according to SEQ ID NO: 72 and the VL has an amino acid sequence according to SEQ ID NO: 77.

6. The nucleic acid of claim 1, wherein the antibody or fragment thereof is selected from the group consisting of a monoclonal antibody, a humanized antibody, and a human antibody.

7. The nucleic acid of claim 1, wherein the antibody fragment is a Fab or a F(ab')2.

8. The nucleic acid of claim 1, wherein the antibody fragment is a Fab.

9. The nucleic acid of claim 8, wherein the Fab is humanized.

10. The nucleic acid of claim 2, wherein the antibody fragment is a Fab.

11. The nucleic acid of claim 10, wherein the Fab is humanized.

12. One or more vectors comprising the nucleic acid of claim 1.

13. One or more vectors comprising the nucleic acid of claim 2.

14. A host cell comprising the one or more vectors of claim 12.

15. A host cell comprising the one or more vectors of claim 13.

16. A method of producing an antibody or a fragment thereof that binds to ticagrelor, comprising culturing the host cell of claim 14 under conditions for expression of the antibody or fragment thereof.

17. A method of producing an antibody or a fragment thereof that binds to ticagrelor, comprising culturing the host cell of claim 15 under conditions for expression of the antibody or fragment thereof.

\* \* \* \* \*

SEQUENCE LISTING

```
Sequence total quantity: 80
SEQ ID NO: 1            moltype = DNA  length = 363
FEATURE                 Location/Qualifiers
source                  1..363
                        mol_type = unassigned DNA
                        organism = Homo sapiens
```

```
SEQUENCE: 1
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc aacagagtac   300
gacctgcaac ggccttttcgg gtttgacttc tggggcaagg ggacaatggt caccgtctcg   360
agt                                                                363

SEQ ID NO: 2             moltype = AA   length = 121
FEATURE                  Location/Qualifiers
source                   1..121
                         mol_type = protein
                         organism = Homo sapiens
SEQUENCE: 2
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCATEY DLQRPFGFDF WGKGTMVTVS   120
S                                                                  121

SEQ ID NO: 3             moltype = AA   length = 5
FEATURE                  Location/Qualifiers
source                   1..5
                         mol_type = protein
                         organism = Homo sapiens
SEQUENCE: 3
SYAMS                                                                5

SEQ ID NO: 4             moltype = AA   length = 17
FEATURE                  Location/Qualifiers
source                   1..17
                         mol_type = protein
                         organism = Homo sapiens
SEQUENCE: 4
AISGSGGSTY YADSVKG                                                  17

SEQ ID NO: 5             moltype = AA   length = 12
FEATURE                  Location/Qualifiers
source                   1..12
                         mol_type = protein
                         organism = Homo sapiens
SEQUENCE: 5
EYDLQRPFGF DF                                                       12

SEQ ID NO: 6             moltype = DNA   length = 333
FEATURE                  Location/Qualifiers
source                   1..333
                         mol_type = unassigned DNA
                         organism = Homo sapiens
SEQUENCE: 6
tcctatgtgc tgactcagcc accctcagcg tctggggccc ccgggcagag ggctaccatc    60
tcctgtctctg gaagcagctc caacatcgga agtaatcttg tgaactggta ccaacaattc   120
ccaggagagg ccccccaagct cctcatcttt agtgacaatc aacgaccctc aggggtccct   180
gaccgattct ctggctccag gtctggcacc tcagcctccc tggccatcag tgggctccag   240
tccgaggatg aggctgatta ttactgtgca acgtgggatg acagactgga tggttatgtg   300
gtattcggcg gagggaccaa gctgaccgtc cta                                333

SEQ ID NO: 7             moltype = AA   length = 111
FEATURE                  Location/Qualifiers
source                   1..111
                         mol_type = protein
                         organism = Homo sapiens
SEQUENCE: 7
SYVLTQPPSA SGAPGQRATI SCSGSSSNIG SNLVNWYQQF PGEAPKLLIF SDNQRPSGVP    60
DRFSGSRSGT SASLAISGLQ SEDEADYYCA TWDDRLDGYV VFGGGTKLTV L            111

SEQ ID NO: 8             moltype = AA   length = 13
FEATURE                  Location/Qualifiers
source                   1..13
                         mol_type = protein
                         organism = Homo sapiens
SEQUENCE: 8
SGSSSNIGSN LVN                                                      13

SEQ ID NO: 9             moltype = AA   length = 7
FEATURE                  Location/Qualifiers
source                   1..7
                         mol_type = protein
                         organism = Homo sapiens
SEQUENCE: 9
```

```
SDNQRPS                                                                         7

SEQ ID NO: 10           moltype = AA  length = 12
FEATURE                 Location/Qualifiers
source                  1..12
                        mol_type = protein
                        organism = Homo sapiens
SEQUENCE: 10
ATWDDRLDGY VV                                                                  12

SEQ ID NO: 11           moltype = DNA  length = 345
FEATURE                 Location/Qualifiers
source                  1..345
                        mol_type = unassigned DNA
                        organism = Homo sapiens
SEQUENCE: 11
caggtacagc tgcagcagtc aggggctgag gtgaagaagc tggggcctca gtgaaggtt    60
tcctgcaagg cttctggata cacctttcat ttacctatgg ttcactgggt gcgccaggcc  120
cccggacaag gcttgagtg atgggatgg atcgaccccg gcatggtta cacaaaatat    180
tcacagaagt tccagggcag agtcaccatt accaggaca catccgcgag cacagcctac  240
atggagatga gcagcctcag atctgaagac acggctgtgt attactgtgc gagagcggac  300
ctgggtgact actggggccg gggaaccctg gtcaccgtc cgagt                   345

SEQ ID NO: 12           moltype = AA  length = 115
FEATURE                 Location/Qualifiers
source                  1..115
                        mol_type = protein
                        organism = Homo sapiens
SEQUENCE: 12
QVQLQQSGAE VKKPGASVKV SCKASGYTFI TYGIHWVRQA PGQGLEWMGW IDPGHGYTKY   60
SQKFQGRVTI TRDTSASTAY MEMSSLRSED TAVYYCARAD LGDYWGRGTL VTVSS       115

SEQ ID NO: 13           moltype = AA  length = 5
FEATURE                 Location/Qualifiers
source                  1..5
                        mol_type = protein
                        organism = Homo sapiens
SEQUENCE: 13
TYGIH                                                                           5

SEQ ID NO: 14           moltype = AA  length = 17
FEATURE                 Location/Qualifiers
source                  1..17
                        mol_type = protein
                        organism = Homo sapiens
SEQUENCE: 14
WIDPGHGYTK YSQKFQG                                                             17

SEQ ID NO: 15           moltype = AA  length = 6
FEATURE                 Location/Qualifiers
source                  1..6
                        mol_type = protein
                        organism = Homo sapiens
SEQUENCE: 15
ADLGDY                                                                          6

SEQ ID NO: 16           moltype = DNA  length = 330
FEATURE                 Location/Qualifiers
source                  1..330
                        mol_type = unassigned DNA
                        organism = Homo sapiens
SEQUENCE: 16
cagtctgtcg tgacgcagcc gccctcagtg tctgcggccc caggacagaa ggtcaccatc   60
tcctgctctg gaagcagctc aacattggg aagaattatg tttcctggtt ccagcagctc  120
ccaggtacag ccccaaaact cctcatttat gacaatcata gcgaccctc agggattcct  180
gaccgattct ctgcctccaa gtctggcacg tcagccaccc tggtcatctc cggtctccag  240
actggggacg aggcccatta ttactgcgga acatgggata ccagactgag tgctggggtg  300
ttcggcggag ggaccaaggt caccgtccta                                    330

SEQ ID NO: 17           moltype = AA  length = 110
FEATURE                 Location/Qualifiers
source                  1..110
                        mol_type = protein
                        organism = Homo sapiens
SEQUENCE: 17
QSVVTQPPSV SAAPGQKVTI SCSGSSSNIG KNYVSWFQQL PGTAPKLLIY DNHKRPSGIP   60
DRFSASKSGT SATLVISGLQ TGDEAHYYCG TWDTRLSAGV FGGGTKVTVL             110

SEQ ID NO: 18           moltype = AA  length = 13
```

```
FEATURE                 Location/Qualifiers
source                  1..13
                        mol_type = protein
                        organism = Homo sapiens
SEQUENCE: 18
SGSSSNIGKN YVS                                                          13

SEQ ID NO: 19           moltype = AA   length = 7
FEATURE                 Location/Qualifiers
source                  1..7
                        mol_type = protein
                        organism = Homo sapiens
SEQUENCE: 19
DNHKRPS                                                                 7

SEQ ID NO: 20           moltype = AA   length = 11
FEATURE                 Location/Qualifiers
source                  1..11
                        mol_type = protein
                        organism = Homo sapiens
SEQUENCE: 20
GTWDTRLSAG V                                                            11

SEQ ID NO: 21           moltype = DNA   length = 360
FEATURE                 Location/Qualifiers
source                  1..360
                        mol_type = unassigned DNA
                        organism = Homo sapiens
SEQUENCE: 21
gaggtgcagc tgttggagtc tgggggaggc ttggtacagc ctgggggtc cctgagactc         60
tcctgtgcag cctctggatt cacctttagc agctatgcca tgagctgggt ccgccaggct       120
ccagggaagg ggctggagtg ggtctcagct attagtggta gtggtggtag cacatactac       180
gcagactccg tgaagggccg gttcaccatc tccagagaca attccaagaa cacgctgtat       240
ctgcaaatga acagcctgag agccgaggac acggccgtgt attactgtgg ccatgatagt       300
agtggttact cctactcctt tgacttctgg ggccggggga ccacggtcac cgtctcgagt       360

SEQ ID NO: 22           moltype = AA   length = 120
FEATURE                 Location/Qualifiers
source                  1..120
                        mol_type = protein
                        organism = Homo sapiens
SEQUENCE: 22
EVQLLESGGG LVQPGGSLRL SCAASGFTFS SYAMSWVRQA PGKGLEWVSA ISGSGGSTYY        60
ADSVKGRFTI SRDNSKNTLY LQMNSLRAED TAVYYCGHDS SGYSYSFDFW GRGTTVTVSS       120

SEQ ID NO: 23           moltype = AA   length = 5
FEATURE                 Location/Qualifiers
source                  1..5
                        mol_type = protein
                        organism = Homo sapiens
SEQUENCE: 23
SYAMS                                                                   5

SEQ ID NO: 24           moltype = AA   length = 17
FEATURE                 Location/Qualifiers
source                  1..17
                        mol_type = protein
                        organism = Homo sapiens
SEQUENCE: 24
AISGSGGSTY YADSVKG                                                      17

SEQ ID NO: 25           moltype = AA   length = 11
FEATURE                 Location/Qualifiers
source                  1..11
                        mol_type = protein
                        organism = Homo sapiens
SEQUENCE: 25
DSSGYSYSFD F                                                            11

SEQ ID NO: 26           moltype = DNA   length = 330
FEATURE                 Location/Qualifiers
source                  1..330
                        mol_type = unassigned DNA
                        organism = Homo sapiens
SEQUENCE: 26
cagtctgtgt tgacgcagcc gccctcagcg tctgggaccc ccgggcagag ggtcaccatc        60
tcttgttctg gaacatctc caacatcgga agtaacactg tcaactggta tcaacacgtc       120
ccaggagcgc cccccagact cctcatctat gttaatgatc agcggccgtc aggggtccct       180
gaccgattct ctgctccaa gtctggcacc tcagcctccc tggccatcag tgggctccag       240
```

```
tctgaagatg aggctgatta ttactgtgca acgtgggatg acaccctgaa tggagggggtc    300
ttcggcggag ggaccaagct gaccgtccta                                      330
```

SEQ ID NO: 27          moltype = AA  length = 110
FEATURE              Location/Qualifiers
source               1..110
                      mol_type = protein
                      organism = Homo sapiens
SEQUENCE: 27
```
QSVLTQPPSA SGTPGQRVTI SCSGNISNIG SNTVNWYQHV PGAAPRLLIY VNDQRPSGVP    60
DRFSGSKSGT SASLAISGLQ SEDEADYYCA TWDDTLNGGV FGGGTKLTVL              110
```

SEQ ID NO: 28          moltype = AA  length = 13
FEATURE              Location/Qualifiers
source               1..13
                      mol_type = protein
                      organism = Homo sapiens
SEQUENCE: 28
```
SGNISNIGSN TVN                                                      13
```

SEQ ID NO: 29          moltype = AA  length = 7
FEATURE              Location/Qualifiers
source               1..7
                      mol_type = protein
                      organism = Homo sapiens
SEQUENCE: 29
```
VNDQRPS                                                              7
```

SEQ ID NO: 30          moltype = AA  length = 11
FEATURE              Location/Qualifiers
source               1..11
                      mol_type = protein
                      organism = Homo sapiens
SEQUENCE: 30
```
ATWDDTLNGG V                                                        11
```

SEQ ID NO: 31          moltype = DNA  length = 387
FEATURE              Location/Qualifiers
source               1..387
                      mol_type = unassigned DNA
                      organism = Homo sapiens
SEQUENCE: 31
```
caggtgcagc tgcaggagtc cggggctgag gtgaagaagc ctgggtcctc ggtgagggtc    60
tcctgcaagg cttctggagg cacccttcgac agttatagta tccattgggt gcgccaggcc   120
cctggacaag gccttgagtg gatgggaggg atcatccctg cctttgggac attaagcagc   180
gcacaggact tccaggccag agtcaccatt agcgcggaca gtccacgag cacagcctat    240
atgctgagctga gcggcctgag atctgaggac acggccgtat attactgtgc gagagggtcc   300
catctttacg attttggag tgcttctcat ccccccaatg atgctcttgc tatttgggggc    360
caaggaaccc tggtcaccgt ctcgagt                                        387
```

SEQ ID NO: 32          moltype = AA  length = 129
FEATURE              Location/Qualifiers
source               1..129
                      mol_type = protein
                      organism = Homo sapiens
SEQUENCE: 32
```
QVQLQESGAE VKKPGSSVRV SCKASGGTFD SYSIHWVRQA PGQGLEWMGG IIPAFGTLSS    60
AQDFQARVTI SADKSTSTAY MELSGLRSED TAVYYCARGS HLYDFWSASH PPNDALAIWG   120
QGTLVTVSS                                                          129
```

SEQ ID NO: 33          moltype = AA  length = 5
FEATURE              Location/Qualifiers
source               1..5
                      mol_type = protein
                      organism = Homo sapiens
SEQUENCE: 33
```
SYSIH                                                                5
```

SEQ ID NO: 34          moltype = AA  length = 17
FEATURE              Location/Qualifiers
source               1..17
                      mol_type = protein
                      organism = Homo sapiens
SEQUENCE: 34
```
GIIPAFGTLS SAQDFQA                                                  17
```

SEQ ID NO: 35          moltype = AA  length = 20
FEATURE              Location/Qualifiers
source               1..20

```
                            mol_type = protein
                            organism = Homo sapiens
SEQUENCE: 35
GSHLYDFWSA SHPPNDALAI                                              20

SEQ ID NO: 36               moltype = DNA   length = 330
FEATURE                     Location/Qualifiers
source                      1..330
                            mol_type = unassigned DNA
                            organism = Homo sapiens
SEQUENCE: 36
cagtctgtcg tgacgcagcc gccctcagtg tctgcggccc caggacagaa ggtcaccatc   60
tcctgctctg gaagcaactc cgacattggc aacaattatg tgtcgtggta ccaacagctc  120
ccaggaacag ccccccaaact cctcatttat gacaataata aacgaccctc agggattcct  180
gaccgattct ctggctccaa gtctggcacg tcagccaccc tggccatcac cggactccag  240
gctgggacg aggccgatta ttactgcggg acatgggata tcagcctgag cgctggcttg   300
ttcggcggag ggaccaaggt caccgtccta                                   330

SEQ ID NO: 37               moltype = AA   length = 110
FEATURE                     Location/Qualifiers
source                      1..110
                            mol_type = protein
                            organism = Homo sapiens
SEQUENCE: 37
QSVVTQPPSV SAAPGQKVTI SCSGSNSDIG NNYVSWYQQL PGTAPKLLIY DNNKRPSGIP   60
DRFSGSKSGT SATLAITGLQ AGDEADYYCG TWDISLSAGL FGGGTKVTVL             110

SEQ ID NO: 38               moltype = AA   length = 13
FEATURE                     Location/Qualifiers
source                      1..13
                            mol_type = protein
                            organism = Homo sapiens
SEQUENCE: 38
SGSNSDIGNN YVS                                                     13

SEQ ID NO: 39               moltype = AA   length = 7
FEATURE                     Location/Qualifiers
source                      1..7
                            mol_type = protein
                            organism = Homo sapiens
SEQUENCE: 39
DNNKRPS                                                             7

SEQ ID NO: 40               moltype = AA   length = 11
FEATURE                     Location/Qualifiers
source                      1..11
                            mol_type = protein
                            organism = Homo sapiens
SEQUENCE: 40
GTWDISLSAG L                                                       11

SEQ ID NO: 41               moltype = DNA   length = 387
FEATURE                     Location/Qualifiers
source                      1..387
                            mol_type = unassigned DNA
                            organism = Homo sapiens
SEQUENCE: 41
caggtgcagc tgcaggagtc cggggctgag gtgaagaagc ctgggtcctc ggtgagggtc   60
tcctgcaagg cttctggagg caccttcgac agttatagta tccattgggt gcgccaggcc  120
cctggacaag ggcttgagtg gatgggaggg atcatccctg cctttgggac attaagcagc  180
gcacaggact ccaggccag agtcaccatt agcgcggaca gtccacgag cacagcctat    240
atggagctga gcggcctgag atctgaggac acggccgtat attactgtgc gagagggagc  300
ttcgactaca ggttttggag tgcttctcat ccccccaatg atgctcttgc tatttgggc   360
caaggaaccc tggtcaccgt ctcgagt                                      387

SEQ ID NO: 42               moltype = AA   length = 129
FEATURE                     Location/Qualifiers
source                      1..129
                            mol_type = protein
                            organism = Homo sapiens
SEQUENCE: 42
QVQLQESGAE VKKPGSSVRV SCKASGGTFD SYSIHWVRQA PGQGLEWMGG IIPAFGTLSS   60
AQDFQARVTI SADKSTSTAY MELSGLRSED TAVYYCARGS FDYRFWSASH PPNDALAIWG  120
QGTLVTVSS                                                          129

SEQ ID NO: 43               moltype = AA   length = 5
FEATURE                     Location/Qualifiers
source                      1..5
                            mol_type = protein
```

```
SEQUENCE: 43
SYSIH                                                              5

SEQ ID NO: 44           moltype = AA   length = 17
FEATURE                 Location/Qualifiers
source                  1..17
                        mol_type = protein
                        organism = Homo sapiens
SEQUENCE: 44
GIIPAFGTLS SAQDFQA                                                 17

SEQ ID NO: 45           moltype = AA   length = 20
FEATURE                 Location/Qualifiers
source                  1..20
                        mol_type = protein
                        organism = Homo sapiens
SEQUENCE: 45
GSFDYRFWSA SHPPNDALAI                                              20

SEQ ID NO: 46           moltype = DNA   length = 330
FEATURE                 Location/Qualifiers
source                  1..330
                        mol_type = unassigned DNA
                        organism = Homo sapiens
SEQUENCE: 46
cagtctgtcg tgacgcagcc gccctcagtg tctgcggccc caggacagaa ggtcaccatc   60
tcctgctctg gaagcaactc cgacattggc aacaattatg tgtcgtggta ccaacagctc  120
ccaggaacag cccccaaact cctcatttat gacaataata aacgaccctc agggattcct  180
gaccgattct ctggctccaa gtctggcacg tcagccaccc tggccatcac cggactccag  240
gctggggacg aggccgatta ttactgcggg acatgggata tcagcctgag cgctggcttg  300
ttcggcggag ggaccaaggt caccgtccta                                   330

SEQ ID NO: 47           moltype = AA   length = 110
FEATURE                 Location/Qualifiers
source                  1..110
                        mol_type = protein
                        organism = Homo sapiens
SEQUENCE: 47
QSVVTQPPSV SAAPGQKVTI SCSGSNSDIG NNYVSWYQQL PGTAPKLLIY DNNKRPSGIP   60
DRFSGSKSGT SATLAITGLQ AGDEADYYCG TWDISLSAGL FGGGTKVTVL             110

SEQ ID NO: 48           moltype = AA   length = 13
FEATURE                 Location/Qualifiers
source                  1..13
                        mol_type = protein
                        organism = Homo sapiens
SEQUENCE: 48
SGSNSDIGNN YVS                                                     13

SEQ ID NO: 49           moltype = AA   length = 7
FEATURE                 Location/Qualifiers
source                  1..7
                        mol_type = protein
                        organism = Homo sapiens
SEQUENCE: 49
DNNKRPS                                                            7

SEQ ID NO: 50           moltype = AA   length = 11
FEATURE                 Location/Qualifiers
source                  1..11
                        mol_type = protein
                        organism = Homo sapiens
SEQUENCE: 50
GTWDISLSAG L                                                       11

SEQ ID NO: 51           moltype = DNA   length = 387
FEATURE                 Location/Qualifiers
source                  1..387
                        mol_type = unassigned DNA
                        organism = Homo sapiens
SEQUENCE: 51
caggtgcagc tgcaggagtc cggggctgag gtgaagaagc ctgggtcctc ggtgagggtc   60
tcctgcaagg cttctggagg caccttcgac agttatagta tccattgggt gcgccaggcc  120
cctggacaag gccttgagtg gatgggaggg atcatccctg cctttgggac attaagcagc  180
gcacaggact ccaggccag agtcaccatt agcgcggaca gtccacgag cacagcctat  240
atggagctga gcgcctgag atctgaggac acggccgtat attactgtgc gagaggctcc  300
ttcgactact acttttggag tgcttctcat ccccccaatg atgctcttgc tatttgggc  360
caaggaaccc tggtcaccgt ctcgagt                                      387
```

```
SEQ ID NO: 52           moltype = AA  length = 129
FEATURE                 Location/Qualifiers
source                  1..129
                        mol_type = protein
                        organism = Homo sapiens
SEQUENCE: 52
QVQLQESGAE VKKPGSSVRV SCKASGGTFD SYSIHWVRQA PGQGLEWMGG IIPAFGTLSS    60
AQDFQARVTI SADKSTSTAY MELSGLRSED TAVYYCARGS FDYYFWSASH PPNDALAIWG  120
QGTLVTVSS                                                          129

SEQ ID NO: 53           moltype = AA  length = 5
FEATURE                 Location/Qualifiers
source                  1..5
                        mol_type = protein
                        organism = Homo sapiens
SEQUENCE: 53
SYSIH                                                                5

SEQ ID NO: 54           moltype = AA  length = 17
FEATURE                 Location/Qualifiers
source                  1..17
                        mol_type = protein
                        organism = Homo sapiens
SEQUENCE: 54
GIIPAFGTLS SAQDFQA                                                  17

SEQ ID NO: 55           moltype = AA  length = 20
FEATURE                 Location/Qualifiers
source                  1..20
                        mol_type = protein
                        organism = Homo sapiens
SEQUENCE: 55
GSFDYYFWSA SHPPNDALAI                                               20

SEQ ID NO: 56           moltype = DNA  length = 330
FEATURE                 Location/Qualifiers
source                  1..330
                        mol_type = unassigned DNA
                        organism = Homo sapiens
SEQUENCE: 56
cagtctgtcg tgacgcagcc gccctcagtg tctgcggccc caggacagaa ggtcaccatc   60
tcctgctctg gaagcaactc cgacattggc aacaattatg tgtcgtggta ccaacagctc  120
ccaggaacag ccccccaaact cctcatttat gacaataata acgaccctc agggattcct  180
gaccgattct ctggctccaa gtctggcacg tcagccaccc tggccatcac cggactccag  240
gctgggacg aggccgatta ttactgcggg acatgggata tcagcctgag cgctggcttg  300
ttcggcggag ggaccaaggt caccgtccta                                   330

SEQ ID NO: 57           moltype = AA  length = 110
FEATURE                 Location/Qualifiers
source                  1..110
                        mol_type = protein
                        organism = Homo sapiens
SEQUENCE: 57
QSVVTQPPSV SAAPGQKVTI SCSGSNSDIG NNYVSWYQQL PGTAPKLLIY DNNKRPSGIP   60
DRFSGSKSGT SATLAITGLQ AGDEADYYCG TWDISLSAGL FGGGTKVTVL             110

SEQ ID NO: 58           moltype = AA  length = 13
FEATURE                 Location/Qualifiers
source                  1..13
                        mol_type = protein
                        organism = Homo sapiens
SEQUENCE: 58
SGSNSDIGNN YVS                                                      13

SEQ ID NO: 59           moltype = AA  length = 7
FEATURE                 Location/Qualifiers
source                  1..7
                        mol_type = protein
                        organism = Homo sapiens
SEQUENCE: 59
DNNKRPS                                                              7

SEQ ID NO: 60           moltype = AA  length = 11
FEATURE                 Location/Qualifiers
source                  1..11
                        mol_type = protein
                        organism = Homo sapiens
SEQUENCE: 60
```

```
GTWDISLSAG L                                                              11

SEQ ID NO: 61            moltype = DNA   length = 387
FEATURE                  Location/Qualifiers
source                   1..387
                         mol_type = unassigned DNA
                         organism = Homo sapiens
SEQUENCE: 61
caggtgcagc tgcaggagtc cggggctgag gtgaagaagc ctgggtcctc ggtgagggtc    60
tcctgcaagg cttctggagg caccttcgac agttatagta tccattgggt gcgccaggcc   120
cctggacaag ggcttgagtg gatgggaggg atcatccctg cctttgggac attaagcagc   180
gcacaggact tccaggccag agtcaccatt agcgcggaca gtccacgag cacagcctat    240
atggagctga gcgcctgag atctgaggac acggccgtat attactgtgc gagagggtcc    300
catctttacg attttggag tgcttctcat cccccaatg atgcttgc tatttggggc       360
caaggaaccc tggtcaccgt ctcgagt                                        387

SEQ ID NO: 62            moltype = AA   length = 129
FEATURE                  Location/Qualifiers
source                   1..129
                         mol_type = protein
                         organism = Homo sapiens
SEQUENCE: 62
QVQLQESGAE VKKPGSSVRV SCKASGGTFD SYSIHWVRQA PGQGLEWMGG IIPAFGTLSS     60
AQDFQARVTI SADKSTSTAY MELSGLRSED TAVYYCARGS HLYDFWSASH PPNDALAIWG   120
QGTLVTVSS                                                           129

SEQ ID NO: 63            moltype = AA   length = 5
FEATURE                  Location/Qualifiers
source                   1..5
                         mol_type = protein
                         organism = Homo sapiens
SEQUENCE: 63
SYSIH                                                                 5

SEQ ID NO: 64            moltype = AA   length = 17
FEATURE                  Location/Qualifiers
source                   1..17
                         mol_type = protein
                         organism = Homo sapiens
SEQUENCE: 64
GIIPAFGTLS SAQDFQA                                                   17

SEQ ID NO: 65            moltype = AA   length = 20
FEATURE                  Location/Qualifiers
source                   1..20
                         mol_type = protein
                         organism = Homo sapiens
SEQUENCE: 65
GSHLYDFWSA SHPPNDALAI                                                20

SEQ ID NO: 66            moltype = DNA   length = 330
FEATURE                  Location/Qualifiers
source                   1..330
                         mol_type = unassigned DNA
                         organism = Homo sapiens
SEQUENCE: 66
cagtctgtcg tgacgcagcc gccctcagtg tctgcggccc caggacagaa ggtcaccatc    60
tcctgctctg gaagcaactc cgacattggc aacaattatg tgtcgtggta ccaacagctc   120
ccaggaacag cccccaaact cctcatttat gacaataata aacgaccctc agggattcct   180
gaccgattct ctggctccaa gtctggcacg tcagccaccc tggccatcac cggactcag    240
gctggggacg aggccgatta ttactgcggg acatggctgt acgaccgggc cgtcggcttg   300
ttcggcggag ggaccaaggt caccgtccta                                    330

SEQ ID NO: 67            moltype = AA   length = 110
FEATURE                  Location/Qualifiers
source                   1..110
                         mol_type = protein
                         organism = Homo sapiens
SEQUENCE: 67
QSVVTQPPSV SAAPGQKVTI SCSGSNSDIG NNYVSWYQQL PGTAPKLLIY DNNKRPSGIP    60
DRFSGSKSGT SATLAITGLQ AGDEADYYCG TWLYDRAVGL FGGGTKVTVL              110

SEQ ID NO: 68            moltype = AA   length = 13
FEATURE                  Location/Qualifiers
source                   1..13
                         mol_type = protein
                         organism = Homo sapiens
SEQUENCE: 68
SGSNSDIGNN YVS                                                       13
```

```
SEQ ID NO: 69           moltype = AA   length = 7
FEATURE                 Location/Qualifiers
source                  1..7
                        mol_type = protein
                        organism = Homo sapiens
SEQUENCE: 69
DNNKRPS                                                                  7

SEQ ID NO: 70           moltype = AA   length = 11
FEATURE                 Location/Qualifiers
source                  1..11
                        mol_type = protein
                        organism = Homo sapiens
SEQUENCE: 70
GTWLYDRAVG L                                                            11

SEQ ID NO: 71           moltype = DNA  length = 387
FEATURE                 Location/Qualifiers
source                  1..387
                        mol_type = unassigned DNA
                        organism = Homo sapiens
SEQUENCE: 71
caggtgcagc tgcaggagtc cggggctgag gtgaagaagc ctgggtcctc ggtgagggtc        60
tcctgcaagg cttctggagg cacctttgac agttatagta tccattgggt gcgccaggcc      120
cctggacaag ggcttgagtg gatgggaggg atcatccctg cctttgggac attaagcagc      180
gcacaggact tccaggccag agtcaccatt agcgcggaca gtccacgag cacagcctat       240
atggagctga cgcctgag atctgaggac acggccgtat attactgtgc gagaggctcc         300
ttcgactact actttggag tgcttctcat ccccccaatg atgctcttgc tatttggggc        360
caaggaaccc tggtcaccgt ctcgagt                                           387

SEQ ID NO: 72           moltype = AA   length = 129
FEATURE                 Location/Qualifiers
source                  1..129
                        mol_type = protein
                        organism = Homo sapiens
SEQUENCE: 72
QVQLQESGAE VKKPGSSVRV SCKASGGTFD SYSIHWVRQA PGQGLEWMGG IIPAFGTLSS        60
AQDFQARVTI SADKSTSTAY MELSGLRSED TAVYYCARGS FDYYFWSASH PPNDALAIWG      120
QGTLVTVSS                                                              129

SEQ ID NO: 73           moltype = AA   length = 5
FEATURE                 Location/Qualifiers
source                  1..5
                        mol_type = protein
                        organism = Homo sapiens
SEQUENCE: 73
SYSIH                                                                    5

SEQ ID NO: 74           moltype = AA   length = 17
FEATURE                 Location/Qualifiers
source                  1..17
                        mol_type = protein
                        organism = Homo sapiens
SEQUENCE: 74
GIIPAFGTLS SAQDFQA                                                      17

SEQ ID NO: 75           moltype = AA   length = 20
FEATURE                 Location/Qualifiers
source                  1..20
                        mol_type = protein
                        organism = Homo sapiens
SEQUENCE: 75
GSFDYYFWSA SHPPNDALAI                                                   20

SEQ ID NO: 76           moltype = DNA  length = 330
FEATURE                 Location/Qualifiers
source                  1..330
                        mol_type = unassigned DNA
                        organism = Homo sapiens
SEQUENCE: 76
cagtctgtcg tgacgcagcc gccctcagtg tctgcggccc caggacagaa ggtcaccatc        60
tcctgctctg gaagcaactc cgacattggc aacaattatg tgtcgtggta ccaacagctc      120
ccaggaacag ccccccaaaact cctcatttat gacaataata aacgaccctc agggattcct    180
gaccgattct ctggctccaa gtctggcacg tcagccaccc tggccatcac cggactccag      240
gctgggacg aggccgatta ttactgcgg acatggctgt acgaccgggc cgtcggcttg        300
ttcggcggag ggaccaaggt caccgtccta                                        330

SEQ ID NO: 77           moltype = AA   length = 110
```

```
FEATURE              Location/Qualifiers
source               1..110
                     mol_type = protein
                     organism = Homo sapiens
SEQUENCE: 77
QSVVTQPPSV SAAPGQKVTI SCSGSNSDIG NNYVSWYQQL PGTAPKLLIY DNNKRPSGIP    60
DRFSGSKSGT SATLAITGLQ AGDEADYYCG TWLYDRAVGL FGGGTKVTVL              110

SEQ ID NO: 78        moltype = AA  length = 13
FEATURE              Location/Qualifiers
source               1..13
                     mol_type = protein
                     organism = Homo sapiens
SEQUENCE: 78
SGSNSDIGNN YVS                                                      13

SEQ ID NO: 79        moltype = AA  length = 7
FEATURE              Location/Qualifiers
source               1..7
                     mol_type = protein
                     organism = Homo sapiens
SEQUENCE: 79
DNNKRPS                                                              7

SEQ ID NO: 80        moltype = AA  length = 11
FEATURE              Location/Qualifiers
source               1..11
                     mol_type = protein
                     organism = Homo sapiens
SEQUENCE: 80
GTWLYDRAVG L                                                        11
```